(12) United States Patent
Hartdegen et al.

(10) Patent No.: US 11,202,626 B2
(45) Date of Patent: Dec. 21, 2021

(54) BONE IMPLANT WITH MEANS FOR MULTI DIRECTIONAL FORCE AND MEANS OF INSERTION

(71) Applicant: CROSSROADS EXTREMITY SYSTEMS, LLC, Memphis, TN (US)

(72) Inventors: Vernon R. Hartdegen, Collierville, TN (US); Michael Chad Hollis, Collierville, TN (US); Glen Coleman, Cordova, TN (US); Daniel Sayger, Southaven, MS (US)

(73) Assignee: CROSSROADS EXTREMITY SYSTEMS, LLC, Memphis, TN (US)

( * ) Notice: Subject to any disclaimer, the term of this patent is extended or adjusted under 35 U.S.C. 154(b) by 561 days.

(21) Appl. No.: 15/623,284

(22) Filed: Jun. 14, 2017

(65) Prior Publication Data
US 2017/0281157 A1    Oct. 5, 2017

Related U.S. Application Data

(63) Continuation-in-part of application No. 15/430,442, filed on Feb. 10, 2017, now abandoned, which is a
(Continued)

(51) Int. Cl.
*A61B 17/064* (2006.01)
*A61B 17/84* (2006.01)
(Continued)

(52) U.S. Cl.
CPC ...... *A61B 17/0642* (2013.01); *A61B 17/0682* (2013.01); *A61B 17/1728* (2013.01);
(Continued)

(58) Field of Classification Search
CPC ............ A61B 17/0642; A61B 17/0682; A61B 17/1728; A61B 17/1775; A61B 17/846;
(Continued)

(56) References Cited

U.S. PATENT DOCUMENTS

| | | |
|---|---|---|
| 2,010,913 A | 8/1935 | Bruce |
| 2,133,859 A | 10/1938 | Hawley |

(Continued)

FOREIGN PATENT DOCUMENTS

| | | |
|---|---|---|
| AU | 2002322567 | 9/2007 |
| CA | 2063484 | 9/1993 |

(Continued)

*Primary Examiner* — Marcela I. Shirsat
(74) *Attorney, Agent, or Firm* — Knobbe Martens Olson & Bear, LLP

(57) ABSTRACT

An assembly used in osteosynthesis comprising a delivery instrument in combination with an implant wherein the delivery instrument releasably holds the implant in a first configuration prior to attachment of the implant to bone. The delivery instrument allows the implant to be affixed to bone before the implant is released from the instrument. And the instrument may comprise guide means for drills, depth gauges, screws, pins, pegs, blades and or drivers which are used or implanted when the implant is releasably attached to the instrument. After the implant is affixed to bone and released from the delivery instrument, the implant assumes at least a second configuration which provides compression and or distraction and or control of spatial orientation.

12 Claims, 66 Drawing Sheets

Related U.S. Application Data continuation-in-part of application No. 15/324,393, filed as application No. PCT/US2015/039551 on Jul. 8, 2015, now Pat. No. 10,492,841, said application No. 15/430,442 is a continuation-in-part of application No. PCT/US2015/042390, filed on Jul. 28, 2015.

(60) Provisional application No. 62/349,991, filed on Jun. 14, 2016, provisional application No. 62/036,235, filed on Aug. 12, 2014, provisional application No. 62/022,811, filed on Jul. 10, 2014.

(51) Int. Cl.

| | | |
|---|---|---|
| *A61B 17/068* | (2006.01) | |
| *A61B 17/86* | (2006.01) | |
| *A61B 17/80* | (2006.01) | |
| *A61B 17/88* | (2006.01) | |
| *A61B 17/17* | (2006.01) | |
| *A61B 17/00* | (2006.01) | |
| *A61F 2/08* | (2006.01) | |

(52) U.S. Cl.
CPC ...... *A61B 17/1775* (2016.11); *A61B 17/8004* (2013.01); *A61B 17/808* (2013.01); *A61B 17/809* (2013.01); *A61B 17/8019* (2013.01); *A61B 17/8052* (2013.01); *A61B 17/8061* (2013.01); *A61B 17/846* (2013.01); *A61B 17/86* (2013.01); *A61B 17/8863* (2013.01); *A61B 2017/00867* (2013.01); *A61B 2017/0645* (2013.01); *A61F 2/0811* (2013.01)

(58) Field of Classification Search
CPC .............. A61B 17/808; A61B 17/1682; A61B 2017/00867; A61B 2017/0645; A61F 2/0811
USPC ............................................ 606/151, 75, 82
See application file for complete search history.

(56) References Cited

U.S. PATENT DOCUMENTS

| | | |
|---|---|---|
| 2,544,492 A | 3/1951 | Downing |
| 2,811,073 A | 10/1957 | Klopstock |
| 3,741,205 A | 6/1973 | Markolf |
| 4,263,903 A | 4/1981 | Griggs |
| 4,278,091 A | 7/1981 | Borzone |
| 4,415,111 A | 11/1983 | McHarrie |
| 4,438,769 A | 3/1984 | Pratt |
| 4,454,875 A | 6/1984 | Pratt |
| 4,484,570 A | 11/1984 | Sutter |
| 4,655,222 A | 4/1987 | Florez |
| 4,805,617 A | 2/1989 | Bedi |
| 4,848,328 A | 7/1989 | Laboureau |
| 4,852,558 A | 8/1989 | Outerbridge |
| 5,013,315 A | 5/1991 | Barrows |
| 5,044,540 A | 9/1991 | Dulebohn |
| 5,209,756 A | 5/1993 | Seedhom |
| 5,246,443 A | 9/1993 | Mai |
| 5,258,012 A | 11/1993 | Luscombe |
| 5,352,229 A | 10/1994 | Goble |
| 5,395,372 A | 3/1995 | Holt |
| 5,449,359 A | 9/1995 | Groiso |
| 5,454,814 A | 10/1995 | Comte |
| 5,456,400 A | 10/1995 | Shichman |
| 5,490,409 A | 2/1996 | Weber |
| 5,498,749 A | 3/1996 | Heise |
| 5,520,700 A | 5/1996 | Beyar |
| 5,578,034 A | 11/1996 | Estes |
| 5,607,425 A | 3/1997 | Rogozinski |
| 5,628,740 A | 5/1997 | Mullane |
| 5,634,926 A | 6/1997 | Jobe |
| 5,660,188 A | 8/1997 | Groiso |
| 5,662,655 A | 9/1997 | Laboureau |
| 5,716,357 A | 2/1998 | Rogozinski |
| 5,749,564 A | 5/1998 | Malek |
| 5,779,707 A | 7/1998 | Bertholet |
| 5,785,713 A | 7/1998 | Jobe |
| 5,788,698 A | 8/1998 | Savornin |
| 5,807,403 A | 9/1998 | Beyar |
| 5,853,414 A | 12/1998 | Groiso |
| 5,904,682 A | 5/1999 | Rogozinski |
| 5,931,839 A | 8/1999 | Medoff |
| 5,947,968 A | 9/1999 | Rogozinski |
| 5,947,999 A | 9/1999 | Groiso |
| 5,972,000 A | 10/1999 | Beyar |
| 5,993,476 A | 11/1999 | Groiso |
| 6,010,504 A | 1/2000 | Rogozinski |
| 6,017,343 A | 1/2000 | Rogozinski |
| 6,019,759 A | 2/2000 | Rogozinski |
| 6,059,787 A | 5/2000 | Allen |
| 6,089,435 A | 7/2000 | Malek |
| 6,105,936 A | 8/2000 | Malek |
| 6,179,840 B1 | 1/2001 | Bowman |
| 6,187,009 B1 | 2/2001 | Herzog |
| 6,281,262 B1 | 8/2001 | Shikinami |
| 6,322,562 B1 | 11/2001 | Wolter |
| 6,334,446 B1 | 1/2002 | Beyar |
| 6,336,927 B2 | 1/2002 | Rogozinski |
| 6,348,054 B1 | 2/2002 | Allen |
| 6,364,884 B1 | 4/2002 | Bowman |
| 6,379,354 B1 | 4/2002 | Rogozinski |
| 6,387,041 B1 | 5/2002 | Harari |
| 6,402,765 B1 | 6/2002 | Monassevitch |
| 6,402,766 B2 | 6/2002 | Bowman |
| 6,406,480 B1 | 6/2002 | Beyar |
| 6,423,073 B2 | 7/2002 | Bowman |
| 6,436,110 B2 | 8/2002 | Bowman |
| 6,447,517 B1 | 9/2002 | Bowman |
| 6,497,707 B1 | 12/2002 | Bowman |
| 6,544,273 B1 | 4/2003 | Harari |
| 6,575,984 B2 | 6/2003 | Beyar |
| 6,575,998 B2 | 6/2003 | Beyar |
| 6,582,435 B2 | 6/2003 | Wellisz |
| 6,592,610 B2 | 7/2003 | Beyar |
| 6,635,058 B2 | 10/2003 | Beyar |
| 6,652,531 B2 | 11/2003 | Wellisz |
| 6,663,642 B2 | 12/2003 | Beyar |
| 6,679,885 B2 | 1/2004 | Wellisz |
| 6,709,437 B2 | 3/2004 | Wellisz |
| 6,730,110 B1 | 5/2004 | Harari |
| 6,746,455 B2 | 6/2004 | Beyar |
| 6,783,531 B2 | 8/2004 | Allen |
| 6,896,684 B2 | 5/2005 | Monassevitch |
| 6,966,911 B2 | 11/2005 | Groiso |
| 6,974,461 B1 | 12/2005 | Wolter |
| 7,044,951 B2 | 5/2006 | Medoff |
| 7,090,676 B2 | 8/2006 | Huebner |
| 7,147,640 B2 | 12/2006 | Huebner |
| 7,153,309 B2 | 12/2006 | Huebner |
| 7,179,260 B2 | 2/2007 | Gerlach |
| 7,189,237 B2 | 3/2007 | Huebner |
| 7,214,232 B2 | 5/2007 | Bowman |
| 7,226,408 B2 | 6/2007 | Harai |
| 7,229,452 B2 | 6/2007 | Kayan |
| 7,235,079 B2 | 6/2007 | Jensen |
| 7,250,054 B2 | 7/2007 | Allen |
| 7,255,701 B2 | 8/2007 | Allen |
| 7,311,712 B2 | 12/2007 | Dalton |
| 7,326,212 B2 | 2/2008 | Huebner |
| 7,438,209 B1 | 10/2008 | Hess |
| 7,473,255 B2 | 1/2009 | McGarity |
| 7,473,257 B2 | 1/2009 | Knöpfle |
| 7,500,979 B2 | 3/2009 | Hueil |
| 7,506,791 B2 | 3/2009 | Omaits |
| 7,537,596 B2 | 5/2009 | Jensen |
| 7,537,603 B2 | 5/2009 | Huebner |
| 7,537,604 B2 | 5/2009 | Huebner |
| 7,556,647 B2 | 7/2009 | Drews |
| 7,578,825 B2 | 8/2009 | Huebner |
| 7,604,151 B2 | 10/2009 | Hess |
| 7,618,441 B2 | 11/2009 | Groiso |

(56) References Cited

U.S. PATENT DOCUMENTS

| | | |
|---|---|---|
| 7,651,498 B2 | 1/2010 | Shifrin |
| 7,665,647 B2 | 2/2010 | Shelton, IV |
| 7,669,746 B2 | 3/2010 | Shelton, IV |
| 7,669,747 B2 | 3/2010 | Weisenburgh, II |
| 7,673,781 B2 | 3/2010 | Swayze |
| 7,673,782 B2 | 3/2010 | Hess |
| 7,704,251 B2 | 4/2010 | Huebner |
| 7,704,279 B2 | 4/2010 | Moskowitz |
| 7,717,945 B2 | 5/2010 | Jensen |
| 7,735,703 B2 | 6/2010 | Morgan |
| 7,740,634 B2 | 6/2010 | Orbay |
| 7,766,209 B2 | 8/2010 | Baxter, III |
| 7,766,948 B1 | 8/2010 | Leung |
| 7,771,433 B2 | 8/2010 | Orbay |
| 7,794,475 B2 | 9/2010 | Hess |
| 7,832,612 B2 | 11/2010 | Baxter, III |
| 7,846,188 B2 | 12/2010 | Moskowitz |
| 7,857,186 B2 | 12/2010 | Baxter, III |
| 7,857,836 B2 | 12/2010 | Huebner |
| 7,867,265 B2 | 1/2011 | Beutter |
| 7,905,381 B2 | 3/2011 | Baxter, III |
| 7,905,910 B2 | 3/2011 | Gerlach |
| 7,909,858 B2 | 3/2011 | Gerlach |
| 7,914,532 B2 | 3/2011 | Shaver |
| 7,918,879 B2 | 4/2011 | Yeung |
| 7,927,332 B2 | 4/2011 | Huebner |
| 7,934,630 B2 | 5/2011 | Shelton, IV |
| 7,935,126 B2 | 5/2011 | Orbay |
| 7,942,903 B2 | 5/2011 | Moskowitz |
| 7,951,180 B2 | 5/2011 | Moskowitz |
| 7,954,686 B2 | 6/2011 | Baxter, III |
| 7,955,388 B2 | 6/2011 | Jensen |
| 7,963,982 B2 | 6/2011 | Kirschman |
| 7,966,799 B2 | 6/2011 | Morgan |
| 7,972,363 B2 | 7/2011 | Moskowitz |
| 8,016,867 B2 | 9/2011 | Bowman |
| 8,043,346 B2 | 10/2011 | Markworth |
| 8,100,953 B2 | 1/2012 | White |
| 8,105,367 B2 | 1/2012 | Austin |
| 8,114,139 B2 | 2/2012 | Sournac |
| 8,137,351 B2 | 3/2012 | Prandi |
| 8,141,762 B2 | 3/2012 | Bedi |
| 8,172,886 B2 | 5/2012 | Castaneda |
| 8,177,819 B2 | 5/2012 | Huebner |
| 8,182,518 B2 | 5/2012 | Butler |
| 8,186,560 B2 | 5/2012 | Hess |
| 8,205,781 B2 | 6/2012 | Baxter, III |
| 8,220,690 B2 | 7/2012 | Hess |
| 8,231,627 B2 | 7/2012 | Huebner |
| 8,231,662 B2 | 7/2012 | Huebner |
| 8,241,326 B2 | 8/2012 | Harari |
| 8,241,338 B2 | 8/2012 | Castaneda |
| 8,252,032 B2 | 8/2012 | White |
| 8,257,370 B2 | 9/2012 | Moskowitz |
| 8,262,711 B2 | 9/2012 | Hess |
| 8,317,070 B2 | 11/2012 | Hueil |
| 8,348,129 B2 | 1/2013 | Bedi |
| 8,348,131 B2 | 1/2013 | Omaits |
| 8,353,913 B2 | 1/2013 | Moskowitz |
| 8,360,297 B2 | 1/2013 | Shelton, IV |
| 8,365,976 B2 | 2/2013 | Hess |
| 8,382,807 B2 | 2/2013 | Austin |
| 8,393,517 B2 | 3/2013 | Milo |
| 8,398,717 B2 | 3/2013 | Kleinman |
| 8,413,872 B2 | 4/2013 | Patel |
| 8,425,574 B2 | 4/2013 | Huebner |
| 8,425,575 B2 | 4/2013 | Huebner |
| 8,425,576 B2 | 4/2013 | Anderson |
| 8,430,292 B2 | 4/2013 | Patel |
| 8,449,561 B2 | 5/2013 | Bowman |
| 8,453,908 B2 | 6/2013 | Bedi |
| 8,464,923 B2 | 6/2013 | Shelton, IV |
| 8,475,504 B2 | 7/2013 | Gillard |
| 8,485,412 B2 | 7/2013 | Shelton, IV |
| 8,486,116 B2 | 7/2013 | Heilman |
| 8,496,693 B2 | 7/2013 | Robinson |
| 8,499,993 B2 | 8/2013 | Shelton, IV |
| 8,518,090 B2 | 8/2013 | Huebner |
| 8,523,919 B2 | 9/2013 | Huebner |
| 8,540,129 B2 | 9/2013 | Baxter, III |
| 8,540,133 B2 | 9/2013 | Bedi |
| 8,545,540 B2 | 10/2013 | Castaneda |
| 8,561,870 B2 | 10/2013 | Baxter, III |
| 8,567,656 B2 | 10/2013 | Shelton, IV |
| 8,574,270 B2 | 11/2013 | Hess |
| 8,584,853 B2 | 11/2013 | Knight |
| 8,585,743 B2 | 11/2013 | Ampuero |
| 8,590,762 B2 | 11/2013 | Hess |
| 8,596,514 B2 | 12/2013 | Miller |
| 8,603,161 B2 | 12/2013 | Drews |
| 8,636,187 B2 | 1/2014 | Hueil |
| 8,652,142 B2 | 2/2014 | Geissler |
| 8,652,180 B2 | 2/2014 | Federspiel |
| 8,668,130 B2 | 3/2014 | Hess |
| 8,672,208 B2 | 3/2014 | Hess |
| 8,672,828 B2 | 3/2014 | Harari |
| 8,679,123 B2 | 3/2014 | Kinmon |
| 8,720,766 B2 | 5/2014 | Hess |
| 8,727,197 B2 | 5/2014 | Hess |
| 8,728,128 B2 | 5/2014 | Hawkes |
| 8,728,129 B2 | 5/2014 | Fritzinger |
| 8,734,516 B2 | 5/2014 | Moskowitz |
| 8,740,915 B2 | 6/2014 | Niederberger |
| 8,747,444 B2 | 6/2014 | Moskowitz |
| 8,763,875 B2 | 7/2014 | Morgan |
| 8,777,969 B2 | 7/2014 | Kayan |
| 8,779,927 B2 | 7/2014 | Bell |
| 8,784,450 B2 | 7/2014 | Moskowitz |
| 8,800,838 B2 | 8/2014 | Shelton, IV |
| 8,808,325 B2 | 8/2014 | Hess |
| 8,808,335 B2 | 8/2014 | Biedermann |
| 8,814,915 B2 | 8/2014 | Hess |
| 8,834,537 B2 | 9/2014 | Castaneda |
| 8,858,562 B2 | 10/2014 | Orbay |
| 8,870,882 B2 | 10/2014 | Kleiner |
| 8,882,812 B2 | 11/2014 | Hess |
| 8,888,824 B2 | 11/2014 | Austin |
| 8,888,826 B2 | 11/2014 | Kinmon |
| 8,894,651 B2 | 11/2014 | Aflatoon |
| 8,899,465 B2 | 12/2014 | Shelton, IV |
| 8,906,046 B2 | 12/2014 | Anderson |
| 8,925,788 B2 | 1/2015 | Hess |
| 8,940,028 B2 | 1/2015 | Austin |
| 8,973,804 B2 | 3/2015 | Hess |
| 8,974,504 B2 | 3/2015 | Hess |
| 8,986,305 B2 | 3/2015 | Aflatoon |
| 8,991,676 B2 | 3/2015 | Hess |
| 8,992,581 B2 | 3/2015 | Austin |
| 9,005,206 B2 | 4/2015 | Ampuero |
| 9,005,293 B2 | 4/2015 | Moskowitz |
| 9,017,331 B2 | 4/2015 | Fox |
| 9,017,380 B2 | 4/2015 | Mayer |
| 9,034,037 B2 | 5/2015 | Fiere |
| 9,072,554 B2 | 7/2015 | Reynolds |
| 9,078,757 B2 | 7/2015 | Kleinman |
| 9,095,338 B2 | 8/2015 | Taylor |
| 9,095,388 B2 | 8/2015 | Hess |
| 9,101,349 B2 | 8/2015 | Knight |
| 9,107,661 B2 | 8/2015 | Euteneuer |
| 9,125,650 B2 | 9/2015 | Euteneuer |
| 9,138,233 B2 | 9/2015 | Anderson |
| 9,179,911 B2 | 11/2015 | Morgan |
| 9,180,022 B2 | 11/2015 | Georges |
| 9,204,932 B2 | 12/2015 | Knight |
| 9,220,515 B2 | 12/2015 | Castaneda |
| 9,237,891 B2 | 1/2016 | Shelton, IV |
| 9,247,978 B2 | 2/2016 | Euteneuer |
| 9,265,649 B2 | 2/2016 | Pflueger |
| D752,219 S | 3/2016 | Peterson |
| 9,271,726 B2 | 3/2016 | Euteneuer |
| 9,283,006 B2 | 3/2016 | Fonte |
| 9,289,206 B2 | 3/2016 | Hess |
| 9,289,210 B2 | 3/2016 | Baxter, III |
| 9,301,854 B2 | 4/2016 | Moskowitz |

(56) References Cited

U.S. PATENT DOCUMENTS

| | | |
|---|---|---|
| 9,307,988 B2 | 4/2016 | Shelton, IV |
| 9,308,033 B2 | 4/2016 | Huebner |
| 9,326,768 B2 | 5/2016 | Shelton, IV |
| 9,326,771 B2 | 5/2016 | Baxter, III |
| 9,339,268 B2 | 5/2016 | Fox |
| 9,370,355 B2 | 6/2016 | Anderson |
| 9,370,356 B2 | 6/2016 | Euteneuer |
| 9,370,376 B2 | 6/2016 | Castaneda |
| 9,387,116 B2 | 7/2016 | Pflueger |
| 9,402,623 B2 | 8/2016 | Kayan |
| 9,402,624 B1 | 8/2016 | Scott |
| 9,408,603 B2 | 8/2016 | Patel |
| 9,408,604 B2 | 8/2016 | Shelton, IV |
| 9,408,647 B2 | 8/2016 | Cheney |
| 9,414,841 B2 | 8/2016 | Euteneuer |
| 9,414,871 B2 | 8/2016 | Huebner |
| 9,421,013 B2 | 8/2016 | Patel |
| 9,445,808 B2 | 9/2016 | Woodard, Jr. |
| 9,451,957 B2 | 9/2016 | Fox |
| 9,463,015 B2 | 10/2016 | Hausen |
| 9,486,212 B2 | 11/2016 | Miller |
| 9,532,821 B2 | 1/2017 | Moskowitz |
| 9,539,023 B2 | 1/2017 | Marotte |
| 9,549,735 B2 | 1/2017 | Shelton, IV |
| 9,561,032 B2 | 2/2017 | Shelton, IV |
| 9,566,063 B2 | 2/2017 | Euteneuer |
| 9,603,641 B2 | 3/2017 | Hulliger |
| 9,615,856 B2 | 4/2017 | Arnett |
| 9,763,715 B2 | 9/2017 | Mather |
| 9,839,458 B2 | 12/2017 | Bouduban |
| 9,861,404 B2 | 1/2018 | Reiley |
| 9,918,762 B2 | 3/2018 | Federspiel |
| 9,955,964 B2 | 5/2018 | Mayer |
| 10,166,022 B2 | 1/2019 | Early |
| 10,186,402 B2 | 1/2019 | Kamata |
| 10,292,743 B2 | 5/2019 | Taylor |
| 10,299,842 B2 | 5/2019 | Hollis |
| 2001/0028148 A1 | 10/2001 | White |
| 2002/0095181 A1 | 7/2002 | Beyar |
| 2002/0111641 A1 | 8/2002 | Peterson |
| 2003/0083663 A1 | 5/2003 | Goldhahn |
| 2003/0158553 A1 | 8/2003 | Michelson |
| 2003/0225409 A1 | 12/2003 | Freid |
| 2004/0073222 A1 | 4/2004 | Koseki |
| 2004/0127896 A1 | 7/2004 | Lombardo |
| 2004/0172040 A1 | 9/2004 | Heggeness |
| 2004/0220570 A1 | 11/2004 | Frigg |
| 2005/0021032 A1 | 1/2005 | Koo |
| 2005/0021035 A1 | 1/2005 | Groiso |
| 2005/0043757 A1 | 2/2005 | Arad |
| 2005/0049600 A1 | 3/2005 | Groiso |
| 2005/0085818 A1 | 4/2005 | Huebner |
| 2005/0096660 A1 | 5/2005 | Allen |
| 2005/0101961 A1 | 5/2005 | Huebner |
| 2005/0107796 A1 | 5/2005 | Gerlach |
| 2005/0119667 A1 | 6/2005 | Leport |
| 2005/0165400 A1 | 7/2005 | Fernandez |
| 2005/0171544 A1 | 8/2005 | Falkner |
| 2005/0234458 A1 | 10/2005 | Huebner |
| 2005/0240187 A1 | 10/2005 | Huebner |
| 2006/0058796 A1 | 3/2006 | Hartdegen |
| 2006/0058802 A1 | 3/2006 | Kofoed |
| 2006/0106391 A1 | 5/2006 | Huebner |
| 2006/0122604 A1 | 6/2006 | Gorhan |
| 2006/0122605 A1 | 6/2006 | Suh |
| 2006/0129151 A1 | 6/2006 | Allen |
| 2006/0200147 A1 | 9/2006 | Ensign |
| 2006/0241612 A1 | 10/2006 | Medoff |
| 2006/0241618 A1 | 10/2006 | Gasser |
| 2006/0264936 A1 | 11/2006 | Partin |
| 2007/0055249 A1 | 3/2007 | Jensen |
| 2007/0173840 A1 | 7/2007 | Huebner |
| 2007/0208358 A1 | 9/2007 | Kayan |
| 2007/0233116 A1 | 10/2007 | Olerud |
| 2008/0147125 A1 | 6/2008 | Colleran |
| 2008/0195099 A1 | 8/2008 | Minas |
| 2008/0200955 A1 | 8/2008 | Tepic |
| 2008/0255620 A1 | 10/2008 | Strauss |
| 2008/0275510 A1 | 11/2008 | Schonhardt |
| 2008/0288000 A1 | 11/2008 | Cawley |
| 2008/0319443 A1 | 12/2008 | Focht |
| 2009/0054930 A1 | 2/2009 | Aflatoon |
| 2009/0138082 A1 | 5/2009 | Reah |
| 2009/0177203 A1 | 7/2009 | Reiley |
| 2009/0182383 A1 | 7/2009 | Prybyla |
| 2009/0254090 A1 | 10/2009 | Lizee |
| 2009/0254126 A1 | 10/2009 | Orbay |
| 2009/0281543 A1 | 11/2009 | Orbay |
| 2010/0036430 A1 | 2/2010 | Hartdegen |
| 2010/0076448 A1 | 3/2010 | Abdou |
| 2010/0082065 A1 | 4/2010 | Butler |
| 2010/0100138 A1 | 4/2010 | Reynolds |
| 2010/0106196 A1 | 4/2010 | Erickson |
| 2010/0133316 A1 | 6/2010 | Lizee |
| 2010/0211116 A1 | 8/2010 | Suh |
| 2010/0256765 A1 | 10/2010 | Butler |
| 2010/0292715 A1* | 11/2010 | Nering ............... A61B 17/064 606/151 |
| 2010/0312275 A1* | 12/2010 | Euteneuer .......... A61B 17/0682 606/219 |
| 2010/0312280 A1 | 12/2010 | Overes |
| 2011/0022049 A1 | 1/2011 | Huebner |
| 2011/0022099 A1 | 1/2011 | Ashman |
| 2011/0029016 A1 | 2/2011 | Yeung |
| 2011/0029023 A1 | 2/2011 | Tornier |
| 2011/0029025 A1 | 2/2011 | Medoff |
| 2011/0054542 A1 | 3/2011 | Kevin |
| 2011/0092981 A1 | 4/2011 | Ng |
| 2011/0098754 A1 | 4/2011 | Hulliger |
| 2011/0118796 A1 | 5/2011 | Reiley |
| 2011/0118840 A1 | 5/2011 | Huntsman |
| 2011/0202092 A1 | 8/2011 | Frigg |
| 2011/0270326 A1 | 11/2011 | Black |
| 2011/0282393 A1 | 11/2011 | Gerlach |
| 2011/0295324 A1 | 12/2011 | Donley |
| 2011/0313421 A1 | 12/2011 | Sidebotham |
| 2011/0319942 A1 | 12/2011 | Bottlang |
| 2012/0022600 A1 | 1/2012 | Overes |
| 2012/0024937 A1 | 2/2012 | Allen |
| 2012/0053638 A1 | 3/2012 | Rusch |
| 2012/0059425 A1 | 3/2012 | Biedermann |
| 2012/0065690 A1 | 3/2012 | Perrow |
| 2012/0078371 A1 | 3/2012 | Gamache |
| 2012/0095513 A1 | 4/2012 | Humphreys |
| 2012/0130374 A1 | 5/2012 | Bouduban |
| 2012/0136396 A1 | 5/2012 | Baker |
| 2012/0143193 A1 | 6/2012 | Hulliger |
| 2012/0150240 A1 | 6/2012 | Medoff |
| 2012/0179207 A1 | 7/2012 | Mekhail |
| 2012/0191141 A1 | 7/2012 | Costabile |
| 2012/0323284 A1 | 12/2012 | Baker |
| 2013/0006247 A1 | 1/2013 | Weiner |
| 2013/0023938 A1 | 1/2013 | Huebner |
| 2013/0023940 A1 | 1/2013 | Hansell |
| 2013/0026206 A1 | 1/2013 | Fox |
| 2013/0030437 A1 | 1/2013 | Fox |
| 2013/0030438 A1* | 1/2013 | Fox ............... A61B 17/0682 606/75 |
| 2013/0046346 A1 | 2/2013 | Thorwarth |
| 2013/0109910 A1 | 5/2013 | Alexander |
| 2013/0138154 A1 | 5/2013 | Reiley |
| 2013/0150900 A1 | 6/2013 | Haddad |
| 2013/0153627 A1* | 6/2013 | Euteneuer ............ A61F 2/0811 227/175.1 |
| 2013/0218285 A1 | 8/2013 | Kleinman |
| 2013/0231667 A1 | 9/2013 | Taylor |
| 2013/0238035 A1 | 9/2013 | Medoff |
| 2013/0267956 A1 | 10/2013 | Terrill |
| 2013/0303071 A1 | 11/2013 | Seki |
| 2013/0325074 A1 | 12/2013 | Ziolo |
| 2013/0345752 A1 | 12/2013 | Hendren |
| 2014/0014553 A1 | 1/2014 | Knight |
| 2014/0018809 A1 | 1/2014 | Allen |
| 2014/0018862 A1 | 1/2014 | Koay |

(56) References Cited

U.S. PATENT DOCUMENTS

| | | |
|---|---|---|
| 2014/0020333 A1 | 1/2014 | Knight |
| 2014/0024002 A1 | 1/2014 | Knight |
| 2014/0034702 A1 | 2/2014 | Miller |
| 2014/0058461 A1 | 2/2014 | Black |
| 2014/0100652 A1 | 4/2014 | Drews |
| 2014/0142628 A1 | 5/2014 | Traynelis |
| 2014/0163621 A1 | 6/2014 | Huebner |
| 2014/0163682 A1 | 6/2014 | Iott |
| 2014/0163683 A1 | 6/2014 | Seifert |
| 2014/0172026 A1 | 6/2014 | Biedermann |
| 2014/0200670 A1 | 7/2014 | Chin |
| 2014/0207195 A1 | 7/2014 | Appenzeller |
| 2014/0222086 A1 | 8/2014 | Kuster |
| 2014/0257420 A1 | 9/2014 | Fox |
| 2014/0276830 A1 | 9/2014 | Cheney |
| 2014/0277516 A1* | 9/2014 | Miller ............... A61B 17/0642 623/18.11 |
| 2014/0296925 A1 | 10/2014 | Lawson |
| 2014/0316470 A1 | 10/2014 | Hartdegen |
| 2014/0358187 A1 | 12/2014 | Taber |
| 2015/0012003 A1 | 1/2015 | Ryan |
| 2015/0045804 A1 | 2/2015 | Orbay |
| 2015/0066095 A1 | 3/2015 | Austin |
| 2015/0080914 A1 | 3/2015 | Roundy |
| 2015/0080969 A1 | 3/2015 | Holly |
| 2015/0133940 A1 | 5/2015 | Palmer |
| 2015/0142063 A1 | 5/2015 | Austin |
| 2015/0148850 A1 | 5/2015 | Orbay |
| 2015/0164564 A1 | 6/2015 | Reiley |
| 2015/0173749 A1 | 6/2015 | Shelton, IV |
| 2015/0173750 A1 | 6/2015 | Shelton, IV |
| 2015/0173751 A1 | 6/2015 | Shelton, IV |
| 2015/0173756 A1 | 6/2015 | Baxter, III |
| 2015/0196333 A1 | 7/2015 | Austin |
| 2015/0216570 A1 | 8/2015 | Hess |
| 2015/0216573 A1 | 8/2015 | Chin |
| 2015/0238191 A1 | 8/2015 | Schellin |
| 2015/0238238 A1 | 8/2015 | Cheney |
| 2015/0282819 A1 | 10/2015 | Austin |
| 2015/0313592 A1* | 11/2015 | Coillard-Lavirotte ..................... A61B 17/0642 606/75 |
| 2015/0320462 A1 | 11/2015 | Biedermann |
| 2015/0351762 A1 | 12/2015 | Vendely |
| 2015/0351763 A1 | 12/2015 | Shelton, IV |
| 2015/0351764 A1 | 12/2015 | Shelton, IV |
| 2016/0015384 A1 | 1/2016 | Roedl |
| 2016/0066907 A1 | 3/2016 | Cheney |
| 2016/0074037 A1 | 3/2016 | Cheney |
| 2016/0089191 A1 | 3/2016 | Pak |
| 2016/0100835 A1 | 4/2016 | Linder |
| 2016/0157906 A1 | 6/2016 | Hollis |
| 2016/0199060 A1 | 7/2016 | Morgan |
| 2016/0235460 A1 | 8/2016 | Wahl |
| 2016/0242771 A1 | 8/2016 | Weinstein |
| 2016/0242927 A1 | 8/2016 | Seifert |
| 2016/0317199 A1 | 11/2016 | Hartdegen |
| 2016/0338697 A1 | 11/2016 | Biedermann |
| 2016/0354117 A1 | 12/2016 | Nakaji |
| 2017/0000533 A1 | 1/2017 | Fallin |
| 2017/0007305 A1 | 1/2017 | Hollis |
| 2017/0065312 A1 | 3/2017 | Lauf |
| 2017/0112553 A1 | 4/2017 | Hansell |
| 2017/0119443 A1 | 5/2017 | Cawley |
| 2017/0156776 A1 | 6/2017 | Weiman |
| 2017/0181779 A1 | 6/2017 | Leither |
| 2017/0196604 A1 | 7/2017 | Hartdegen |
| 2017/0196606 A1 | 7/2017 | Cianfrani |
| 2017/0202552 A1 | 7/2017 | Coleman |
| 2017/0202585 A1 | 7/2017 | Leak |
| 2017/0209193 A1 | 7/2017 | Hartdegen |
| 2017/0238974 A1 | 8/2017 | Konieczynski |
| 2017/0245901 A1 | 8/2017 | Grigorian |
| 2017/0354509 A1 | 12/2017 | Finley |
| 2018/0000592 A1 | 1/2018 | Mayer |
| 2018/0206892 A1 | 7/2018 | Hartdegen |
| 2018/0296257 A1 | 10/2018 | Penzimer |
| 2018/0317906 A1 | 11/2018 | Hollis |
| 2018/0353172 A1 | 12/2018 | Hartdegen |

FOREIGN PATENT DOCUMENTS

| | | |
|---|---|---|
| CN | 2404495 | 11/2000 |
| DE | 3119550 | 12/1982 |
| DE | 29721858 | 3/1998 |
| DE | 19821680 | 8/1999 |
| DE | 20001879 | 5/2000 |
| DE | 102004015223 | 10/2005 |
| EP | 0092383 | 11/1987 |
| EP | 0253629 | 9/1994 |
| EP | 509513 | 7/1996 |
| EP | 0768062 | 4/1997 |
| EP | 0826340 | 3/1998 |
| EP | 0857462 | 8/1998 |
| EP | 0682920 | 5/2000 |
| EP | 0867149 | 9/2000 |
| EP | 1870042 | 7/2009 |
| EP | 2231044 | 3/2012 |
| EP | 3082632 | 10/2016 |
| EP | 3166505 | 5/2017 |
| EP | 3166522 | 5/2017 |
| EP | 3179939 | 6/2017 |
| FR | 2694696 | 11/1994 |
| FR | 2725126 | 4/1997 |
| FR | 2758252 | 4/1999 |
| FR | 2874316 | 10/2006 |
| FR | 2927527 | 8/2009 |
| FR | 2874166 | 3/2012 |
| FR | 2935256 | 3/2012 |
| FR | 2980966 | 11/2013 |
| GB | 2118474 | 10/1985 |
| GB | 2471648 | 1/2012 |
| WO | WO1992017122 | 10/1992 |
| WO | WO2001056489 | 8/2001 |
| WO | WO2003068081 | 8/2003 |
| WO | WO2003071962 | 9/2003 |
| WO | WO2005055027 | 6/2005 |
| WO | WO2008007196 | 1/2008 |
| WO | WO2008129061 | 10/2008 |
| WO | WO2010004602 | 1/2010 |
| WO | WO2011014547 | 2/2011 |
| WO | WO2011110916 | 9/2011 |
| WO | WO2012071129 | 5/2012 |
| WO | WO2013006833 | 1/2013 |
| WO | WO2013010282 | 1/2013 |
| WO | WO2013055824 | 4/2013 |
| WO | WO2013130978 | 9/2013 |
| WO | WO2013186205 | 12/2013 |
| WO | WO2014014453 | 1/2014 |
| WO | WO2015004391 | 1/2015 |
| WO | WO2015095126 | 6/2015 |
| WO | WO2015107311 | 7/2015 |
| WO | WO2015130609 | 9/2015 |
| WO | WO2016007624 | 1/2016 |
| WO | WO2016007626 | 1/2016 |
| WO | WO2016025162 | 2/2016 |
| WO | WO2016033426 | 3/2016 |
| WO | WO2016110760 | 7/2016 |
| WO | WO2017011589 | 1/2017 |
| WO | WO2017139315 | 8/2017 |
| WO | WO2017139328 | 8/2017 |
| WO | WO2018145064 | 8/2018 |
| WO | WO2018148284 | 8/2018 |

* cited by examiner

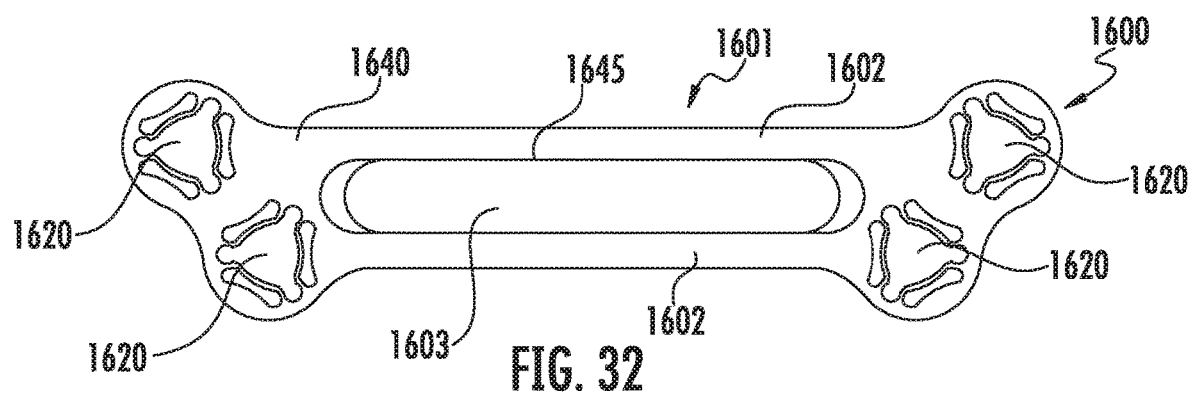
FIG. 32
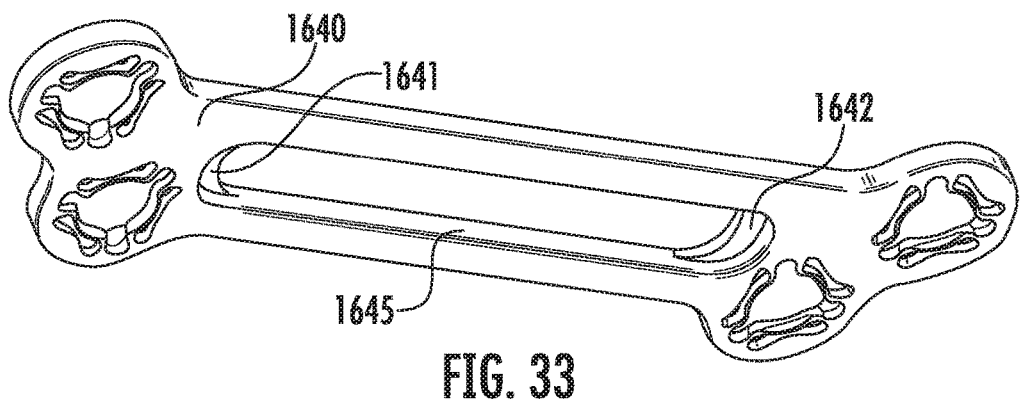
FIG. 33
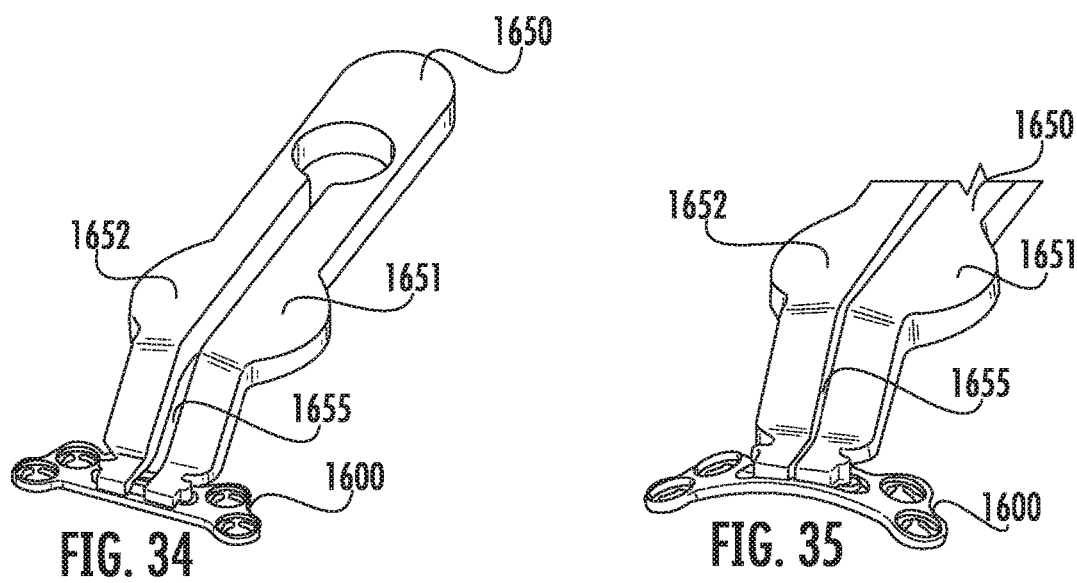
FIG. 34
FIG. 35

SECTION A-A

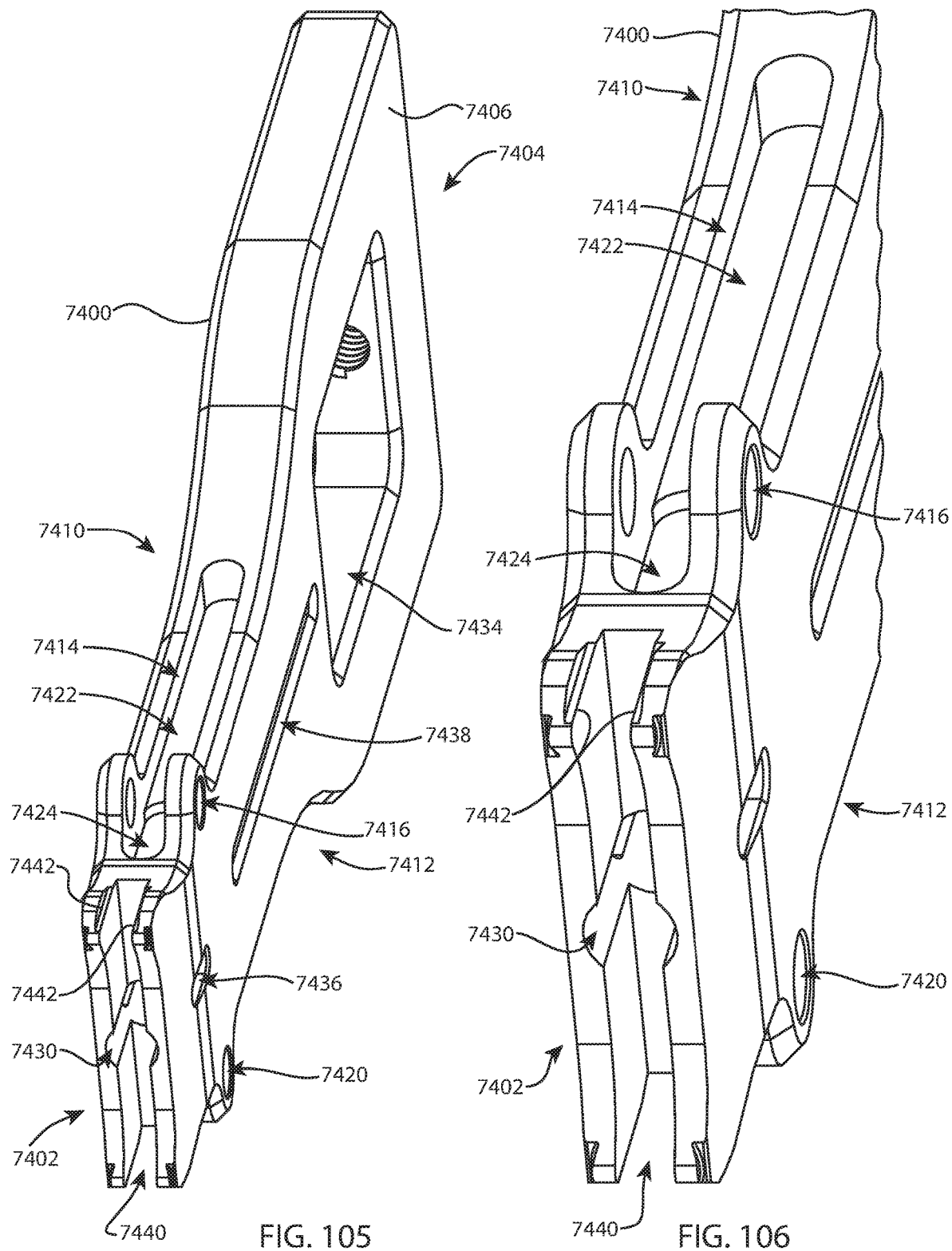

BONE IMPLANT WITH MEANS FOR MULTI DIRECTIONAL FORCE AND MEANS OF INSERTION

CROSS-REFERENCE TO RELATED APPLICATIONS

The present application claims priority to:

U.S. Provisional Patent Application No. 62/349,991, entitled IMPLANT INSERTER, which was filed on Jun. 14, 2016.

The present application is also a continuation-in-part of:

U.S. patent application Ser. No. 15/430,442, entitled BONE IMPLANT WITH MEANS FOR MULTI DIRECTIONAL FORCE AND MEANS OF INSERTION, which was filed on Feb. 10, 2017.

U.S. patent application Ser. No. 15/430,442 is a continuation-in-part of:

U.S. patent application Ser. No. 15/324,393, entitled BONE IMPLANT AND MEANS OF INSERTION, which has a 371(c) date of Jan. 6, 2017 and a filing date of Jul. 8, 2015.

U.S. patent application Ser. No. 15/324,393 is a 371 national stage application of:

P.C.T. Patent Application No. PCT/US2015/039551, entitled BONE IMPLANT AND MEANS OF INSERTION, which was filed on Jul. 8, 2015.

P.C.T. Patent Application No. PCT/US2015/039551 claims priority to:

U.S. Provisional Patent Application No. 62/022,811, entitled BONE IMPLANT AND MEANS OF INSERTION, which was filed on Jul. 10, 2014.

U.S. patent application Ser. No. 15/430,442 is also a continuation-in-part of:

P.C.T. Patent Application No. PCT/US2015/042390, entitled BONE IMPLANT WITH MEANS FOR MULTI DIRECTIONAL FORCE, which was filed on Jul. 28, 2015.

P.C.T. Patent Application No. PCT/US2015/042390 claims priority to:

U.S. Provisional Patent Application No. 62/036,235, entitled BONE IMPLANT WITH MEANS FOR MULTI DIRECTIONAL FORCE, which was filed on Aug. 12, 2014.

The foregoing are incorporated by reference as though set forth herein in their entirety.

TECHNICAL FIELD

The present disclosure is in the technical field of medical devices. More particularly, the present disclosure is in the technical field of bone fixation or arthrodesis or deformity correction. The technology relates to a fixation system for bones of all types with an assembly comprised of an inserter and implant. Such systems are used in osteosynthesis (bone fusion), wherein the implant bridges the fracture generating compression (or distraction) across the bone members. The compression (or distraction) is generated by the properties of the implant and the different configurations of the implant. For example, the implant may have a first configuration when in freestate and a second configuration required for insertion. It is desirable for optimal implant placement and function to be able to pre-assemble or attach the implant to an inserter to facilitate placement of the implant on or in the bone. The implant may be indicated for the various bones of the entire skeleton. A "bone fixation device" or implant may include any of a variety of devices that secure an object to a bone, including but not limited to staples, bone plates, modular staples, bone screws, pins, blades, suture anchors, and the like.

The present disclosure relates to an implant and a corresponding inserter. More specifically, the present disclosure is made in the context of a bone staple and a corresponding inserter. However, the disclosed technology is broadly applicable outside this context, as will be apparent to one of skill in the art.

The staple has a free state, or relaxed state, which is its shape when no external forces are acting upon the staple, other than gravity; in the free state, the staple legs converge at their tips. The staple is made from high elasticity materials such as nitinol and/or polyetheretherketone (PEEK) so that the staple may be elastically deformed by an external force, and then resume the free state when the external force is removed.

The inserter securely and releasably couples to the staple. When actuated, the inserter urges the staple out of the free state into a continuum of elastically deformed states in which the staple legs a) progressively approach a parallel condition, b) achieve a parallel condition, or c) progressively diverge at their free ends. When the inserter is uncoupled from the bone staple, the bone staple resumes the free state, or attempts to do so. When the bone staple is implanted in bone, then the staple may only be able to partially relax toward the free state due to the resistance of the bone.

BACKGROUND

The present technology is in the technical field of medical devices. More particularly, the present technology is in the technical field of bone fixation or arthrodesis or deformity correction. The technology relates to a fixation system for bones of all types. Such systems are used in osteosynthesis (bone fusion), wherein the implant bridges the fracture generating a force across the bone members. The force (e.g. compression or distraction) is generated by the properties of the implant and the different configurations/geometries of the implant. For example, the implant may have a first configuration for insertion/implantation and a second or third configuration required for generating/creating a particular force magnitude and vector. It may be desirable for improved fusion to provide a force across a majority of the bone surfaces to be fused, not just a particular region. The implant may be indicated for the various bones of the entire skeleton. A "bone fixation device" or "implant" may include any of a variety of devices that secure an object to a bone, including but not limited to staples, bone plates, modular staples, bone screws, pins, blades, suture anchors, and the like.

The present technology seeks to remedy the problems of the prior art. The technology produces a system that allows placement of an implant in its final required position with or without additional manipulation. In addition, the present technology will maintain an implant in a first configuration allowing the implant to assume at least a second configuration once placed in its final position. The current technology may not require additional implant positioning manipulation once the inserter is removed or it may be manipulated after insertion. Also, the current technology may incorporate other necessary features into the inserter and implant that are required for final placement. For example the inserter may allow preparation for drill holes, bone screws, etc. and or act to position to the implant in a particular location or position.

The present technology also produces a system that allows use of an implant that may provide a force (e.g. a compressive force) uniformly across bones to be fused. In addition, the present technology includes instrumentation necessary for proper placement and function of the implant. The technology includes an implant that provides a means for generating a force in more than one direction. Also, the technology incorporates other necessary features into the inserter and implant that are required for final placement. For example the inserter may allow preparation for drill holes, bone screws, etc. and or act to position to the implant in a particular location or position.

SUMMARY

The present technology includes a fastening device or implant and a means of insertion and or manipulation. The fastening device may be a bone staple, bone plate, modular staple, or the like. The fastening device has elastic properties or other material properties that allow the device to have at least two configurations or configurable to various positions placed on the bone. The free-state or implanted-state of the device may provide compression and or distraction across two or more bone members. The inserter may hold the fastening device (or implant) in a configuration that is different than the free-state or implanted-state configuration. This first configuration may be useful in placement of the implant onto or into bone members. Fastening device and implant are used interchangeably in this application and are not intended to be limiting in nature. And the means of insertion or manipulation may be referred to herein as the inserter and or the delivery instrument.

The present technology may have the inserter pre-assembled to the implant or affixed to the implant at the time of use. The inserter may be temporarily attached to the implant to facilitate the final implantation of the implant device. The inserter may have features that engage the implant to facilitate the inserter maintaining the first implant configuration. Similarly, the implant may have features for engaging the inserter. The inserter is attached to or engaged with the implant in such a way that allows removal of the inserter once the implant is in its final position on or in the bone. Once the inserter is removed, additional manipulation may not be needed to position the implant in its final placement. Alternatively, the implant may be manipulated to achieve final orientation (e.g. compression). The inserter preferably engages the implant such that it does not interfere with final implant placement.

The present technology has an implant or portion of an implant that is made of an elastic material or a material that allows the implant to have multiple configurations. The ability of the implant to have multiple configurations may be a result of the material properties that have shape memory or super elastic properties or it may be a result of manipulation (mechanical, physical, chemical or otherwise) of the implant to create a second configuration. The implant may be held in one configuration during insertion or removal and returns to or is placed in another configuration in its free-state or implanted-state. The implant may have features for engaging the bone. These features may include bone screws, leg members, or other features for attaching the implant to bone. The implant may have features for engaging the inserter. The engagement between the implant and inserter may allow the implant to be placed in its final position without the inserter interfering with this final positioning. The implant may be placed in its final position while the inserter is still engaged to the implant eliminating the need for final/secondary seating. The inserter is preferably removed from the implant in a direction or manner that is conducive to the surgical procedure. For example, this removal may be from the top, side or any other direction or motion. Once the inserter is removed, the implant may take on the free-state or implanted-state configuration. The engaging features of the inserter and or implant may also be used to remove or revise the implant should such a need arise. While the implant is in its implanted position, the inserter may be re-engaged to the implant. The inserter device normally engages the implant in such a way that it maintains the implant in a first configuration. The implant may have at least a second configuration after the inserter is removed, which is different from the first configuration either via material properties or deformation to a final shape. The inserter may have a feature or features such as guide means that allow use of drills, screws, drivers, depth gages, etc. while the inserter is still attached to the implant. The inserter may have a feature or features that allow for preparation of the bone for the implant while the implant is attached to the inserter. The inserter may have features and/or mechanisms that allow manipulation of the implant to achieve at least a second configuration. The inserter may also have members or features that engage some aspect of the implant for maintaining a first configuration. The members may be stationary, non-stationary or movable (retractable, etc.). The inserter is preferably attached to the implant in such a way that it does not interfere with the final placement or seating of the implant. For example, the inserter may not be attached in such a way that it will inhibit the final positioning or placement of the implant on or into the bone. For example, the inserter may be "top loading" or able to be removed in a direction away from the bone. The inserter may allow for a change in the relative position of for example the fastening member(s) or leg or legs to the bridge member to achieve a desired effect such as compression. This relative change or changes in position should not interfere with the final seating of the bridge member or legs on or into the bone.

The inserter may be a one piece construct, two piece construct, etc. or an assembly. The construct may separate into multiple pieces to facilitate attachment to or removal from the implant. The implant and inserter may be assembled to each other by the manufacturer or may be assembled at the time of use.

The implant may have multiple configurations, for example one for inserting into the bone and at least a second configuration for compressing, distracting, controlling spatial orientation or the like of one or more bone segments. The implant may have one or more bridge members. The implant may have leg members for engaging the bone. The implant may have modular members for engaging bone, such as bone screws, pins or pegs. To those skilled in the art, it will be evident that multiple options exist for connecting an implant to bone. The connecting members or features may not necessarily be of the same material as the bridge component. The deformability aspect of the current technology may be in the bridge member(s), the connecting member(s) or another member(s) of the implant or fixation device. The material properties of the current technology may be appropriate for allowing manipulation other than shape memory of the implant features to generate the desired outcome or final configuration of the implant. The leg member(s) may be configured to receive members from the inserter to hold the implant in its first configuration or to allow manipulation of the implant to another configuration. The first configuration may hold the implant in such a way to facilitate final seating of the implant in its final position against the bone. The inserter/implant assembly preferably is such that there is no interference of the inserter features between the implant and the bone. Removal of the inserter may allow the implant to take on a second or third or additional configuration. Alternatively, the inserter may be used to manipulate the implant into a second or third or additional configuration.

The present technology includes an implant and a means of insertion and or manipulation. The implant may be a bone staple, bone plate, modular staple, or the like. The implant may have elastic properties or other material properties or geometries that allow the device to have more than one configuration or configurable to various positions when placed on or in the bone. The implant provides a force or forces (e.g. compression or distraction) across two or more bone segments. The inserter or delivery device holds the implant in a configuration that is different from the implanted or final configuration. The terms "fastening device" and "implant" may be used interchangeably in this application and are not intended to be limiting in nature, and the terms "inserter," "inserting apparatus" and "delivery device" are also used interchangeably in this application and are not intended to be limiting in nature.

The implant of the present technology may be constructed of an elastic material or a material that allows the implant to have multiple configurations, such as nitinol. The ability of the implant to have multiple configurations may be a result of the material properties that have shape memory or elastic properties or it may be a result of manipulation (rnechani<.; al, µhysical, chemical, temperature, electrical or otherwise) of the implant to create multiple configurations. The implant has features for engaging the bone. These features may include bone screws, leg members, or other features for attaching the implant to bone. The implant may have features for engaging with an inserter or delivery device as instruments for implantation. The implant has a first configuration for insertion, a second configuration for generating a force magnitude and vector in one direction, and a third configuration for generating a force magnitude and vector in the same or a second direction while maintaining the first force generated by the second configuration. The implant may also have a second configuration that generates a force or compression in one or more directions simultaneously. The implant may be attached to the inserting apparatus in such a way to allow the user to determine the order and or timing of providing force in one or more directions. The insertion apparatus may have a feature or features that allow use of drills, screws, drivers, depth gages, etc. while being attached to the implant. The inserter may have a feature or features that allow for preparation of the bone for the implant while the implant is attached to the inserter. The inserting apparatus has features for engaging the implant that may maintain the implant in multiple configurations. For example the inserting apparatus may maintain the implant in a first configuration, second configuration, or third configuration or a combination of configurations. When the inserting apparatus is removed, the implant is allowed to take on a second, third or additional configuration(s). The inserter may be used to manipulate the implant into a second or third or additional configuration. The implant may take on a second or third or additional configuration(s) while still attached to an inserting apparatus.

The implant may have multiple configurations, for example one for inserting into the bone and at least a second configuration for compressing, distracting, controlling spatial orientation or the like of one or more bone segments and a third configuration that may generate a force in the same or different direction than the second configuration. The force generated may be used for compressing, distracting, controlling spatial orientation or the like of one or more bone segments. For the exemplary embodiment described herein, a compressive force may be used for discussion, but should not be considered limiting. Other applications for the current technology exist that may require a force other than a compressive force. The implant may have one or more bridge members of varying configurations. The implant may have protruding members for engaging the bone. The implant may have modular members for engaging bone, such as bone screws or pegs. Based on the description of the technology herein, to those skilled in the art it will be evident that multiple options exist for connecting an implant to bone. The connecting members or features may not necessarily be of the same material as the bridge component. The ability of the current technology to generate a force or forces in the same or different directions may result from movement of the bridge member(s), the connecting member(s) or other member(s) of the implant or fixation device or a combination of different member(s) or feature(s) of the implant.

The foregoing summary of the current technology discusses the merits of the current technology in terms of an implantable device. The merits of the current technology may also apply to an embodiment of the technology in an external or nonimplantable embodiment. The use of the current technology is not limited to just implantable embodiments.

The summary of the current technology discusses the merits of the current technology in terms of an implantable device for generating compression, distraction, controlling spacial orientation or the like. The merits of the current technology may also apply to an embodiment of the technology in an external or non-implantable embodiment. The use of the current technology is not limited to just implantable embodiments.

BRIEF DESCRIPTION OF THE DRAWINGS

Exemplary embodiments of the technology will become more fully apparent from the following description and appended claims, taken in conjunction with the accompanying drawings. Understanding that these drawings depict only exemplary embodiments and are, therefore, not to be considered limiting of the scope of the technology, the exemplary embodiments will be described with additional specificity and detail through use of the accompanying drawings in which:

FIG. 32 is a bottom view of an implant of the ninth embodiment of the current technology depicting an implant with a means for connection to bone engaging features and a means for engaging an inserter;

FIG. 33 is a bottom perspective view of the embodiment shown in FIG. 32;

FIG. 34 is a perspective view of the ninth embodiment depicting the implant depicted in FIG. 32 assembled to an inserter of the current technology. The implant is held in a first configuration;

FIG. 35 is a perspective view of the ninth embodiment depicting of the implant depicted in FIG. 32 assembled to an inserter of the current technology. The implant is shown in a second configuration;

FIG. 105 is yet another isometric view of the body of FIG. 103 from another different direction;

FIG. 106 is a detail view of a portion of the body of FIG. 105;

FIG. 119 is a cross sectional view of the implant and inserter of FIG. 117, taken along section line 119-119 of FIG. 117; and FIG. 120 is a cross sectional view of the implant and inserter of FIG. 118, taken along section line 120-120 of FIG. 118.

DETAILED DESCRIPTION

Exemplary embodiments of the technology will be best understood by reference to the drawings, wherein like parts are designated by like numerals throughout. It will be readily understood that the components of the technology, as generally described and illustrated in the figures herein, could be arranged and designed in a wide variety of different configurations. Thus, the following more detailed description of the embodiments of the apparatus, system, and method is not intended to limit the scope of the invention, as claimed, but is merely representative of exemplary embodiments of the technology.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Figure 3:
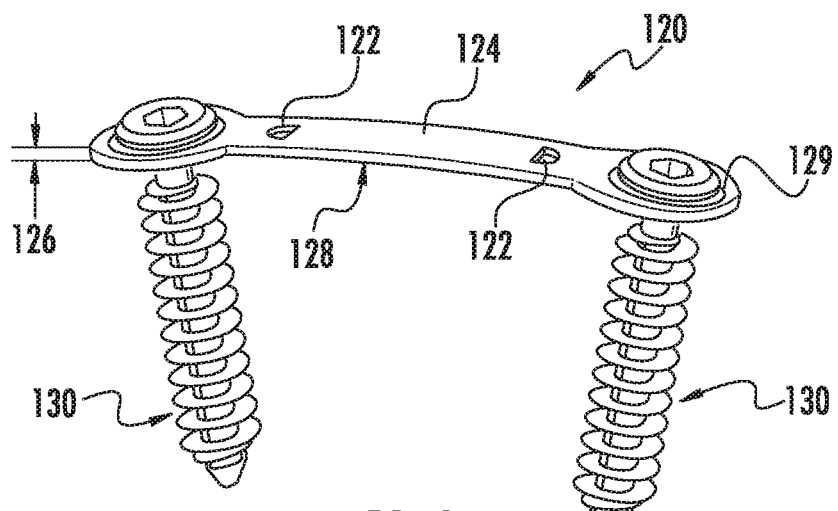
FIG. 3 is a perspective view of the implant of the first embodiment in a second configuration with bone screws assembled.
Figure 11:
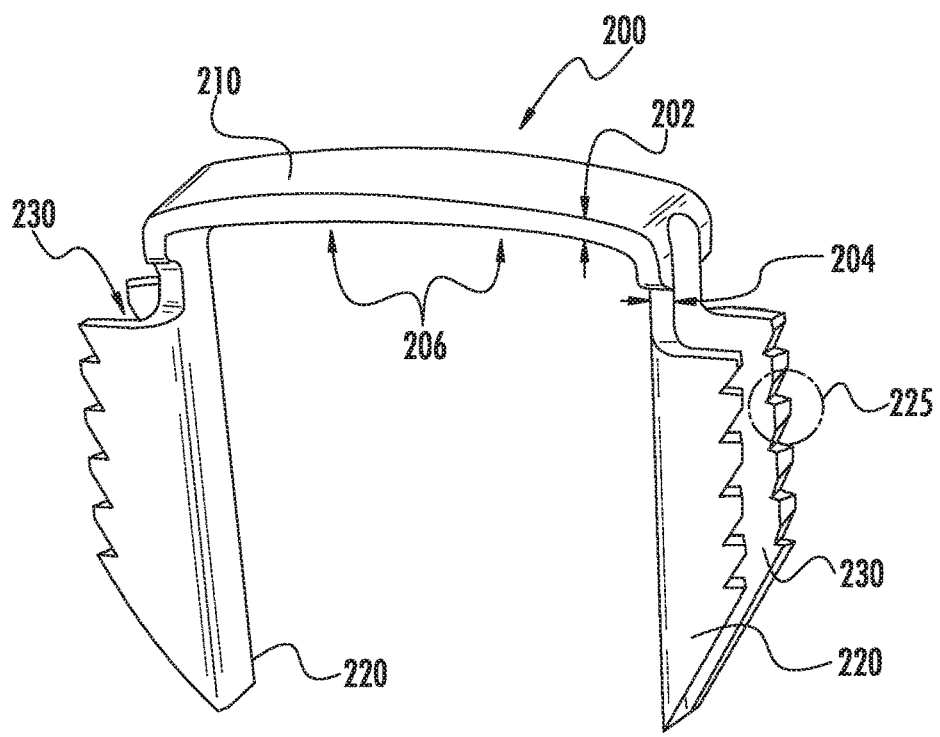
FIG. 11 is a perspective view of second embodiment of an implant or fixation device shown in a first configuration with parallel leg members.
Figure 12:
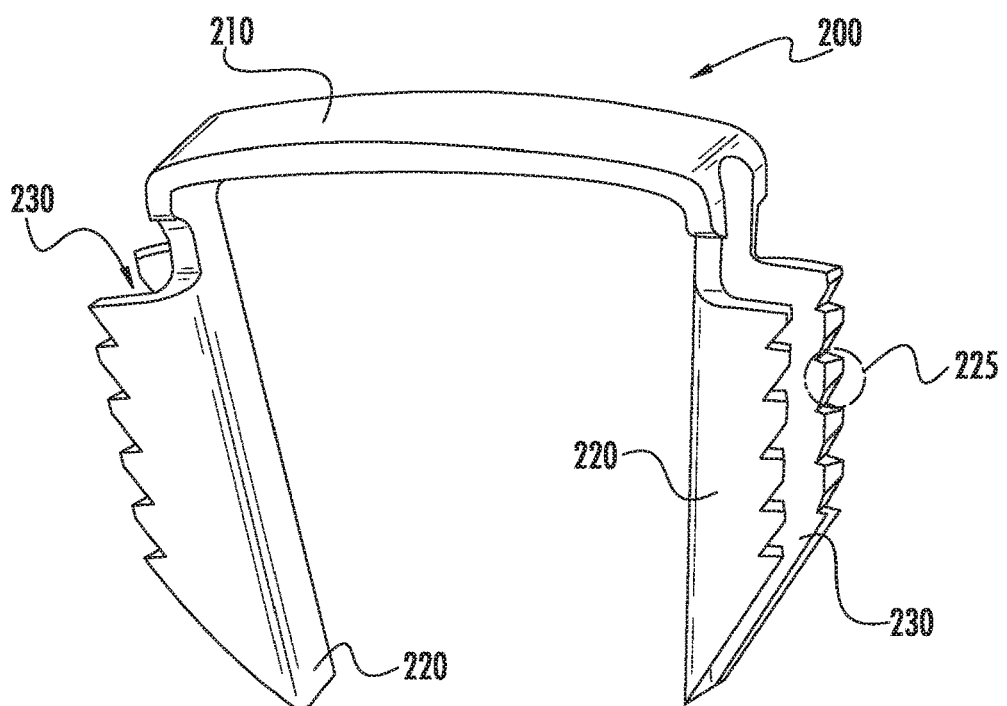
FIG. 12 is a perspective view of the second implant embodiment of FIG. 11 shown in a second configuration with the legs converging.
Figure 14:
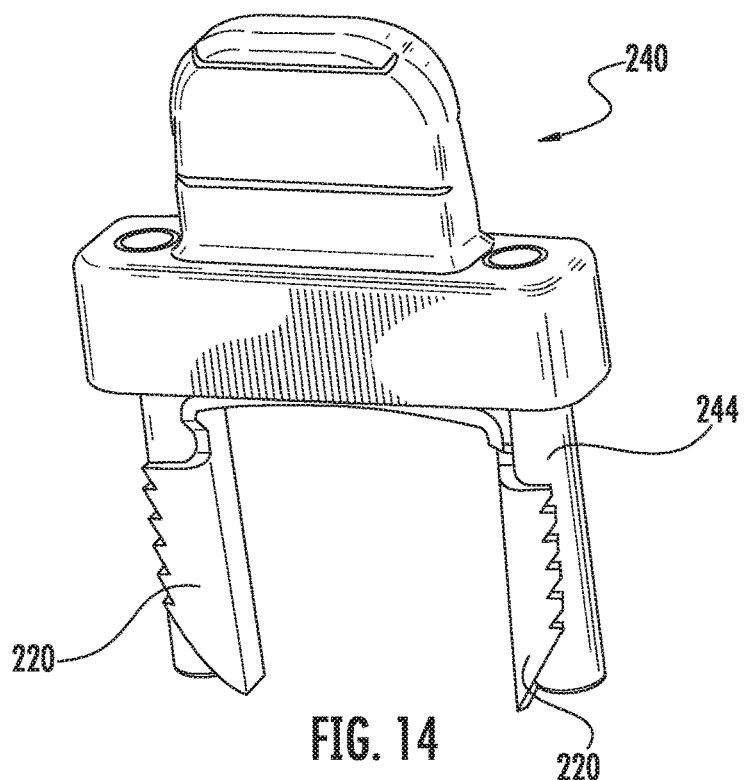
FIG. 14 is a perspective view of a second embodiment of an implant or fixation device shown in a first configuration with parallel leg members on the inserter of FIG. 13.
Figure 19:
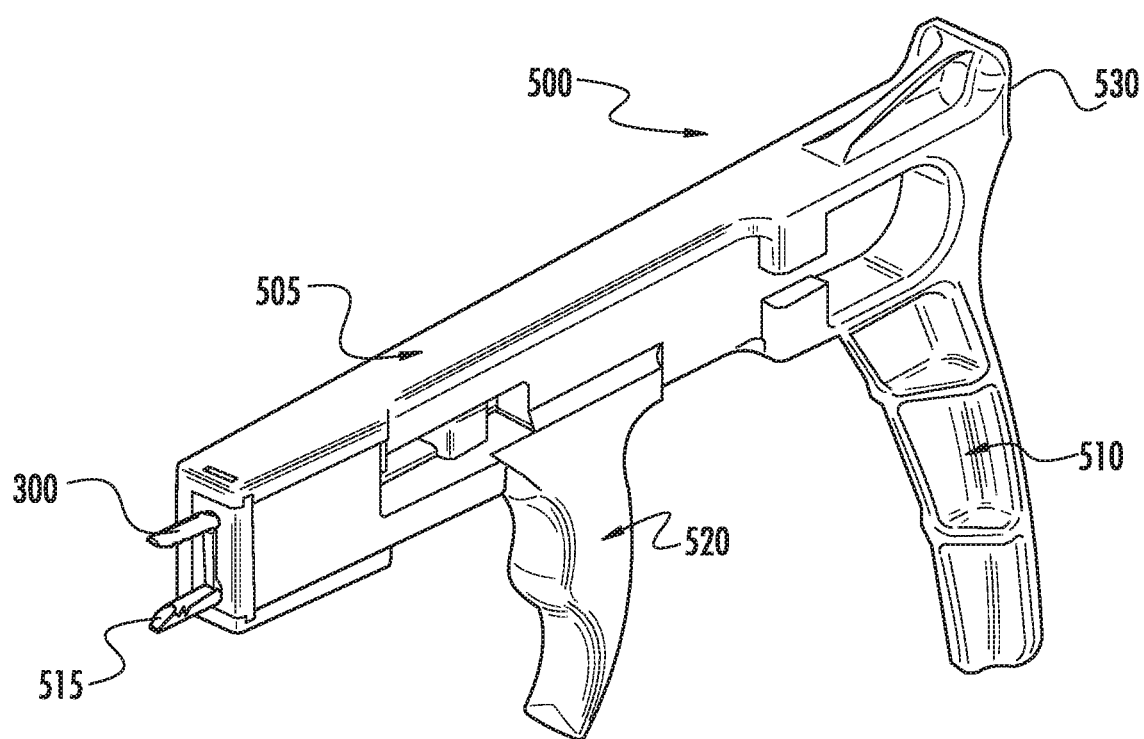
FIG. 19 is a perspective view of a fourth embodiment of the current technology depicting an implant preassembled to an inserter with retractable engagement pins.

The present technology may include a fastening device and an inserter. Exemplary embodiments of the fastening device and inserter are shown in FIGS. 1, 14 and 19. The fastening device may be of a configuration similar to a modular staple or bone plate as shown in FIG. 3. The fastening device may also have a configuration resembling a bone staple as shown in FIGS. 11, 12, 15 and 16. The present technology may have the inserter pre-assembled or affixed to the implant as shown in FIGS. 1 and 14. The implant or implants may not be pre-assembled to the inserter. The implant or implants could be held in a particular configuration in the packaging that facilitates engagement with the inserter. FIGS. 11 and 12 depict an embodiment of the fastening device or implant that shows one possible combination of implant configurations. FIGS. 11 and 14 show this embodiment maintained in a first configuration for insertion. FIG. 12 shows this embodiment in its free-state or implanted-state configuration.

The embodiments described herein may be used in connection with any type of inserter or fixation device, including but not limited to various bone staples, bone plates, etc. that have more than one implant configuration where the insertion device does not interfere with the final placement of the implant.

Figure 1A:
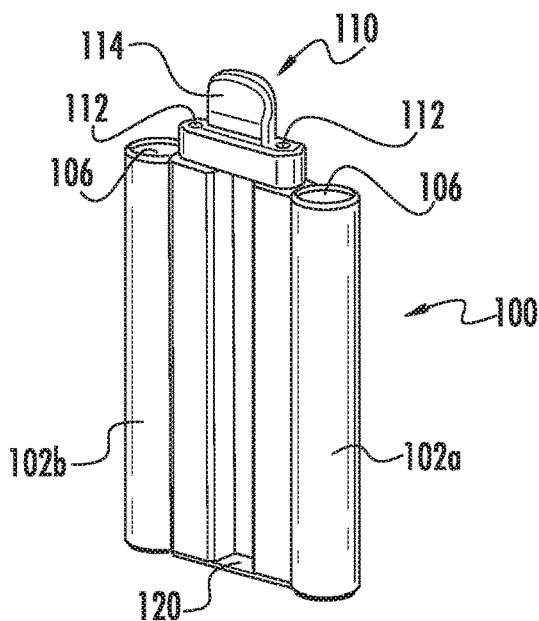
FIG. 1A is a perspective view of a first embodiment of the current technology depicting a multiple component inserter attached to a modular implant or fixation device.
Figure 1B:
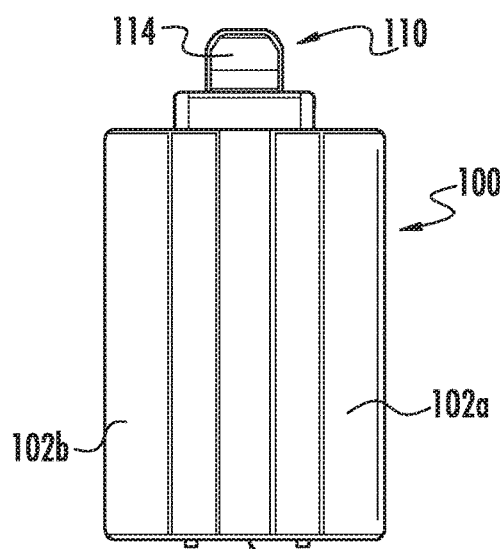
FIG. 1B is a frontal view of the first embodiment shown in FIG. 1A.
Figure 1C:
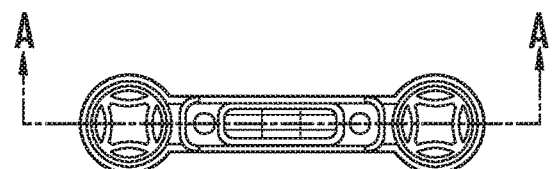
FIG. 1C is a top view of the first embodiment showing a section line A-A.
Figure 1D:
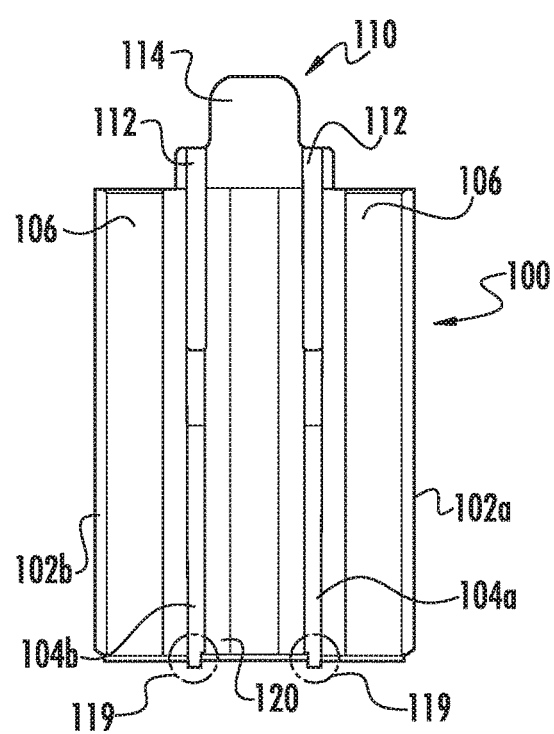
FIG. 1D is the section view A-A shown in FIG. 1C.
Figure 1E:
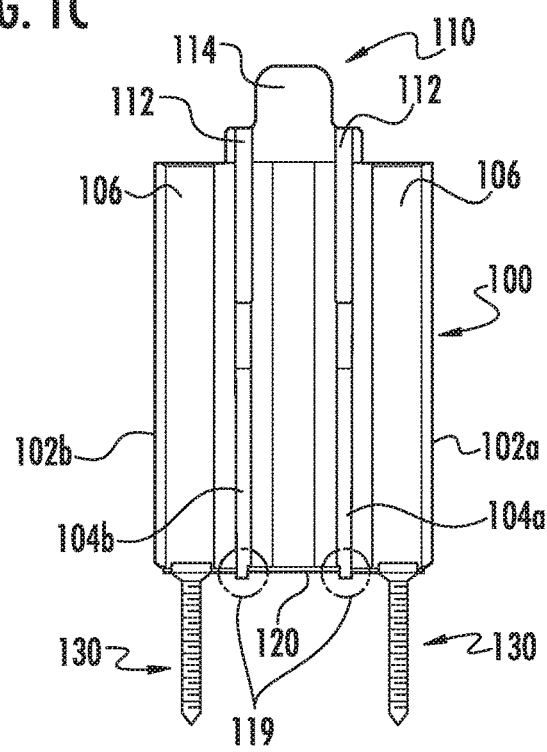
FIG. 1E is the section view A-A but with bone screws inserted as a means of fixating the implant to the bone.
Figures 2A, 2B:
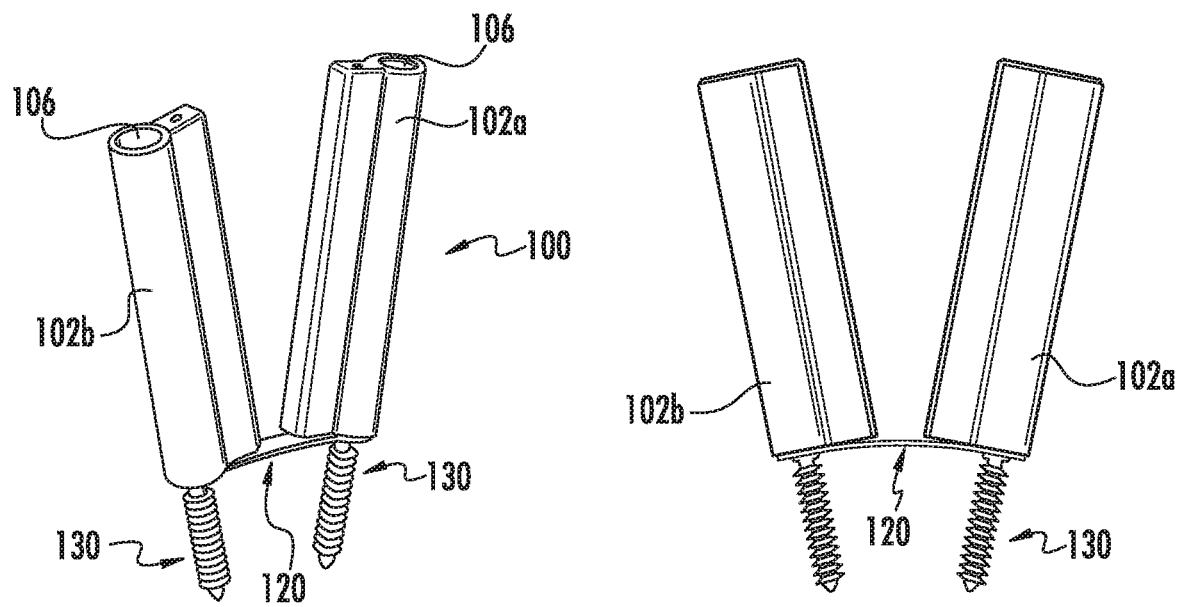
FIG. 2A is a perspective view of the first embodiment of the current technology, depicting a multiple component inserter attached to a modular implant or fixation device.
FIG. 2B is a cross a front view of the first embodiment shown in FIG. 2A.
Figure 2C:
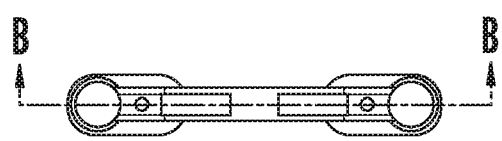
FIG. 2C is a top view of FIG. 2B showing a section line B-B.
Figure 2D:
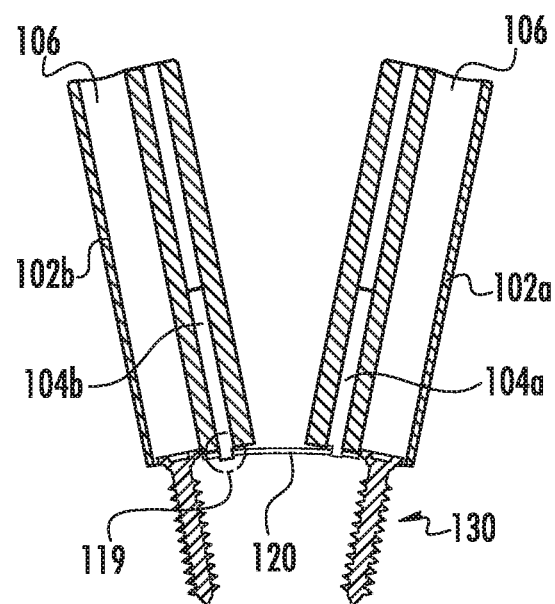
FIG. 2D is the section view B-B shown in FIG. 2C.

As shown in FIGS. 1A, 1B, 1D and 1E, the inserter 100 is assembled to the implant 120. The implant 120 is shown in a first configuration that may or may be flat. The inserter 100 may or may not have features that allow preparation of the bone for receiving other members of the implant. In this embodiment, the inserter 100 has two tube members 102a and 102b that allow the bone to be prepared through the internal diameters 106. The tube members 102a and 102b also serve as drill guides. Implant 120 is temporarily connected to the tubes 102a and 102b by the engagement pins 104a and 104b. The two independent tubes 102a and 102b are individually connected to the implant 120 by the engagement pins 104a and 104b. The engagement pins may or may not extend completely through the implant. The engagement pins could also be temporarily or permanently attached to the implant as opposed to being part of the inserter assembly. The engagement pins may extend through the implant with features that engage the bone for provisional fixation during the procedure. Also, this embodiment shows the use of circular pins, however, to those skilled in the art the use of other attachment means will be obvious and may or may not be separate pieces from the tube members. The means of attaching the plate to the inserter is shown on the bridge area of the plate, but could occur anywhere on or around the periphery of the plate. The two independent tubes are held in relative position to each other by clip 110. Clip 110 has a means for holding during insertion or removal, tab member 114, and two engagement pins 112. The engagement pins 112 engage the tubes 102a and 102b to hold them in relative position to each other thereby maintaining the implant 120 in its first configuration. FIG. 1E depicts the inserter with the bone screws 130 inserted into the implant 120 while the implant is maintained in its first configuration. FIGS. 1C and 1D show an engagement 119 where the engagement pins 104a and 104b controllably interface with the engagement holes 122 shown in FIG. 3. Implant 120 is shown in a first configuration in FIGS. 1A, 1B, 1D and 1E. Alternatively, the inserter 100 may be used for implant manipulation or for holding the implant in a first configuration with or without a means for preparing for other implant members, e.g. bone screws. The bone preparation may or may not be distinct from the inserter. Bone preparation may be done in the implant first configuration and/or in a second configuration.

FIGS. 2A, 2B, 2C and 2D depict the inserter 100 without the clip 110. The inserter assembly 100 is shown in a manner depicting an initial release step that may or may not allow the implant 120 to have a second configuration. In this embodiment, the bone screws 130 have been prepared and placed into the implant 120. The inserter tubes 102a and 102b are still engaged in the implant 120 via the engagement pins 104a and 104b. The implant 120 is shown in a second configuration and is achieved either by the intrinsic mechanical properties of the material or secondary mechanical manipulation of one or more areas of the plate. FIGS. 2A, 2B, 2C and 2D show the inserter temporarily attached to the implant after preparation of the bone and placement of the bone screws 130. The inserter 100 is shown just prior to removal of the inserter 100 from the implant 120. The independent inserter tubes 102a and 102b accommodate the second configuration of the implant 120.

FIG. 3 depicts the implant 120 in its second configuration after removal of the inserter 100 or possibly after secondary mechanical manipulation/deformation. The bone screws 130 may be prepared and positioned through the internal diameter 106 while the inserter 100 was still attached to the implant 120. FIG. 3 shows one embodiment of the engagement hole 122 that accepts the engagement pins 104a and 104b of the inserter tube 102a and 102b.

Figure 4:
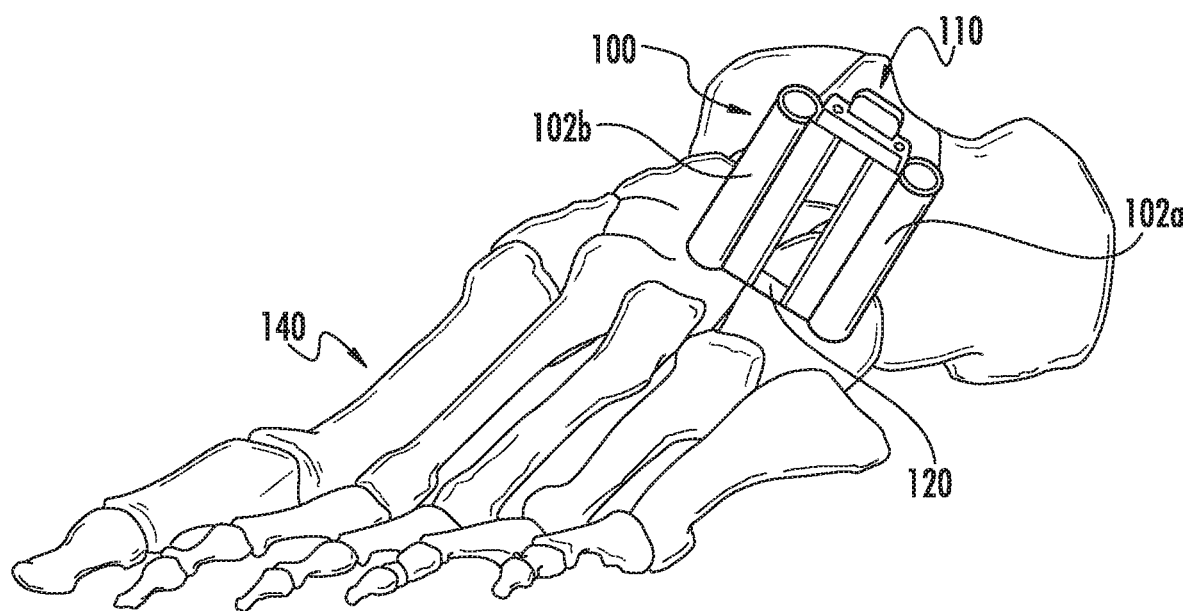
FIG. 4 is a perspective view of the first embodiment of FIG. 1 on a bone.
Figure 5:
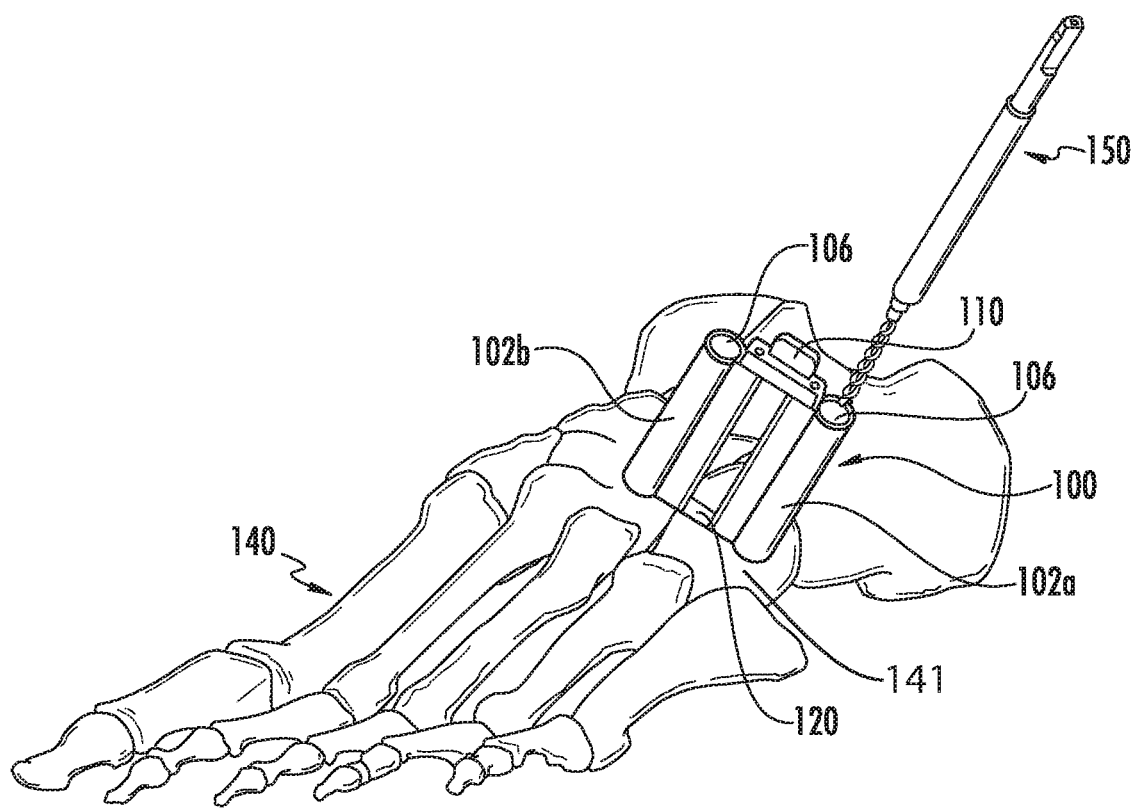
FIG. 5 is a perspective view of the first embodiment of FIG. 1 on a bone and showing preparation of the bone with a drill bit.
Figure 6:
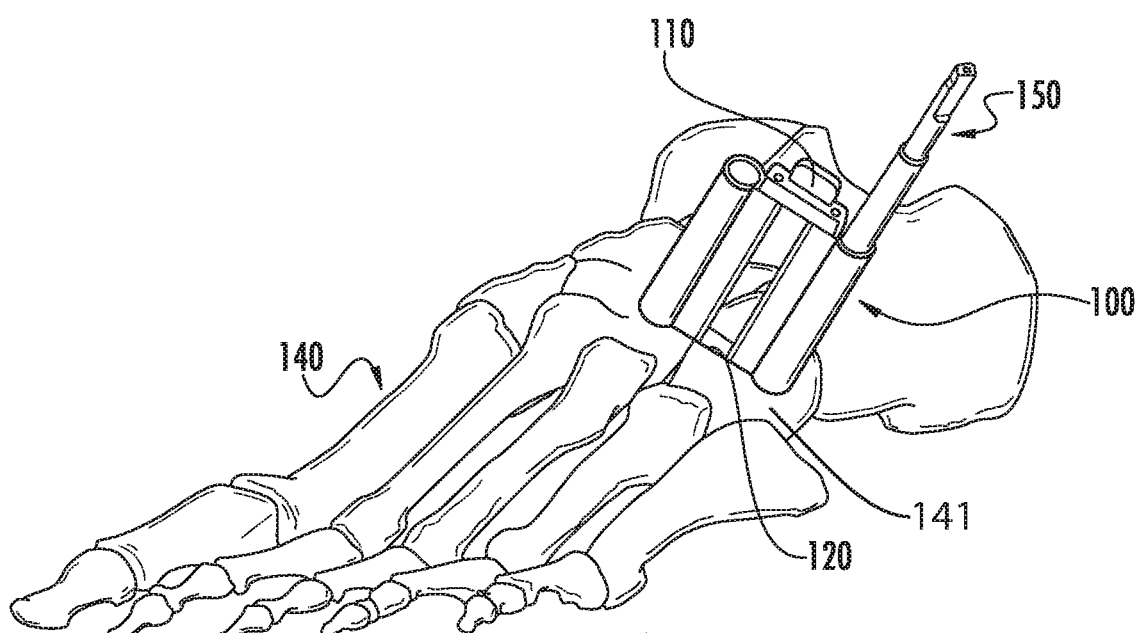
FIG. 6 is a perspective view of the first embodiment of FIG. 1 on a bone and showing preparation of the bone with a drill bit.

FIG. 4 depicts one embodiment of the inserter 100 assembled to implant 120 on a foot 140. FIGS. 5 and 6 depict one embodiment of the inserter 100 assembled to implant 120 on a foot 140 further showing preparation of the bone 141 with drill 150 through the internal diameter 106 to accept bone screws or other fixation features of the implant 120. In FIGS. 4, 5 and 6, clip 110 maintains the tubes 102a and 102b in a relative position to each other. Clip 110 may or may not be a separate assembly; the functionality could be achieved via an integral feature, molded-in for example, to the tube(s). Clip 110 is shown to provide a rigid, static connection between the tubes 102a and 102b. The connection mechanism between the tubes 102a and 102b may also have a dynamic, moveable connection (e.g. application of springs) so that the tubes will allow the plate to conform in some way to the bone prior to complete removable of clip 110. The tubes 102*a* and 102*b* are controllably engaged in implant 120 via engagement pins 104*a* and 104*b* and engagement features 122. In this embodiment, the clip 110, the tubes 102*a* and 102*b*, engagement pins 104*a* and 104*b* and engagement holes 122 act together to maintain the implant 120 in a first configuration. In alternate embodiments more components or fewer may be needed to maintain the implant in a first configuration.

Figure 7:
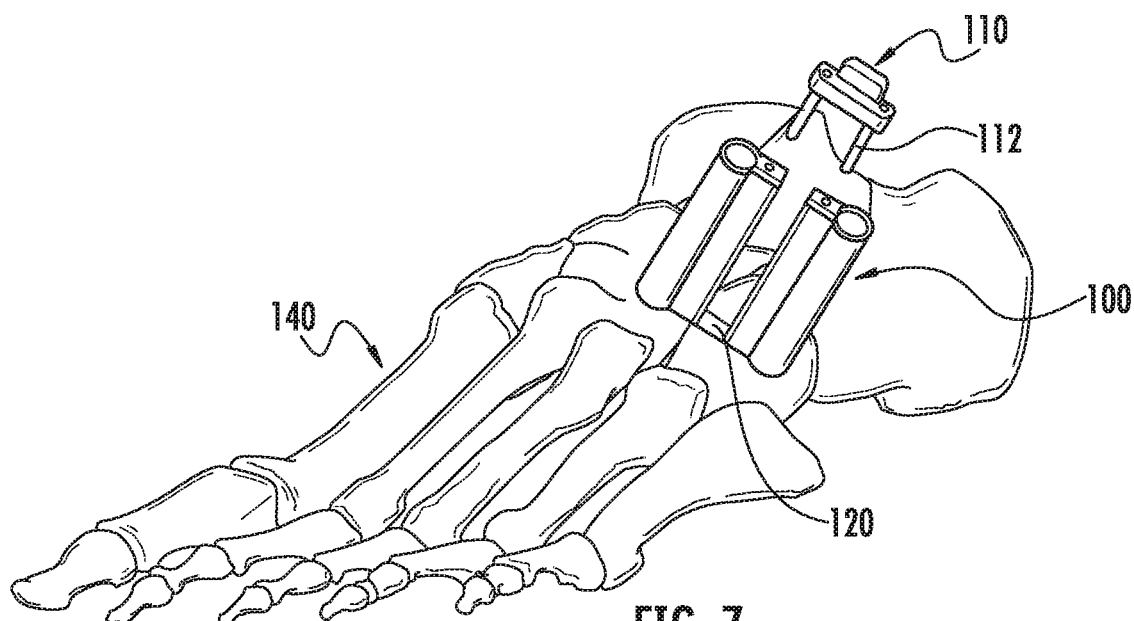
FIG. 7 is a perspective view of the first embodiment of FIG. 1 on a bone after the final placement of the implant has been completed.
Figure 8:
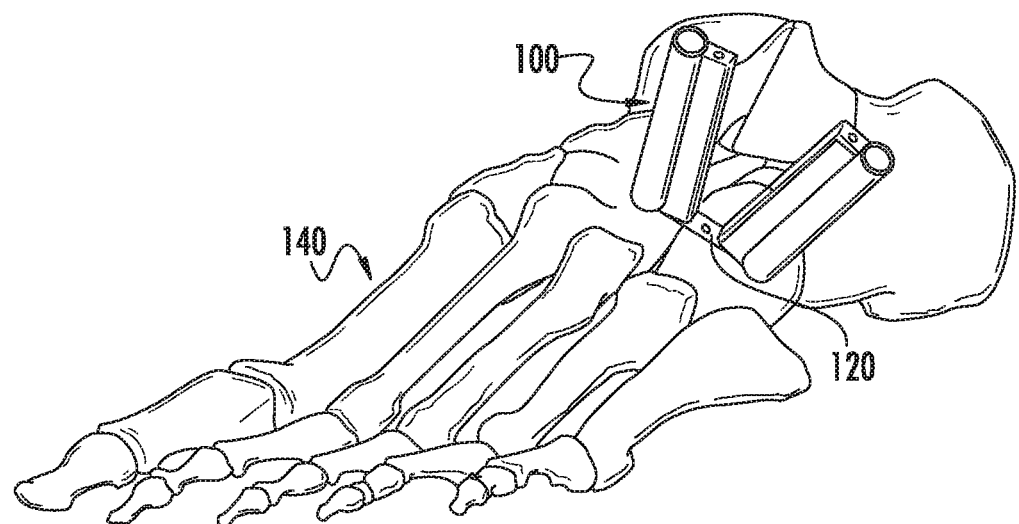
FIG. 8 is a perspective view of the first embodiment of FIG. 1 on a bone after the final placement of the implant has been completed.
Figure 9:
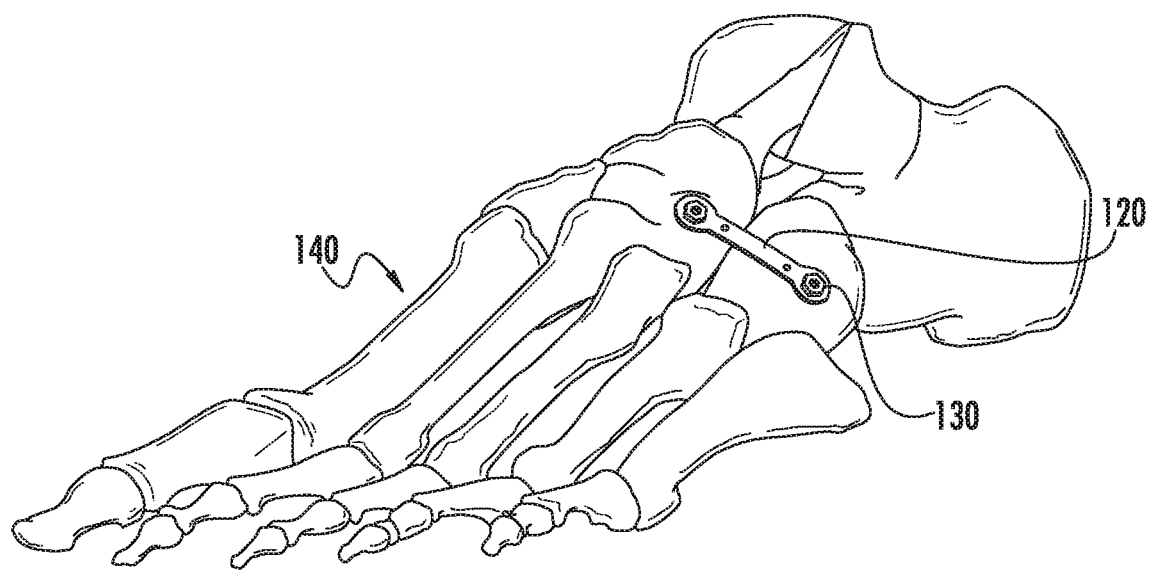
FIG. 9 is a perspective view of the implant of the first embodiment of FIG. 1 on the bone after the final placement of the implant has been completed.

FIG. 7 depicts one embodiment of the inserter 100 assembled to implant 120 on a foot 140. This figure depicts the first removal step for this particular embodiment of the inserter 100. In FIG. 7 the bone has been prepared accordingly and the implant 120 is in its final position on the bone and in its first configuration. FIG. 7 shows removal of clip 110 from inserter 100. As further shown in FIG. 8, removal of the clip 110 from the inserter 100 after completing the appropriate bone preparation allows the implant 120 to adapt to a second configuration while the implant 120 is in its final implant position. Bone screws 130 (not shown in FIG. 7 or 8) may or may not have been prepared and positioned while the inserter assembly 100 was engaged to the implant 120. FIG. 9 shows implant 120 on bone 141 after removal of the inserter assembly 100 after the implant 120 is in its final position either before or after the implant achieves its second configuration.

Figure 10A:
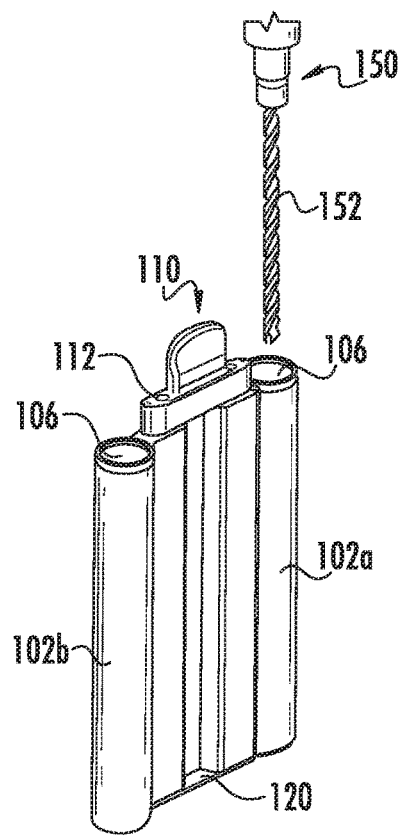
FIG. 10A is a perspective view of the first embodiment of FIG. 1 not shown on a bone showing the use of a drill.
Figure 10B:
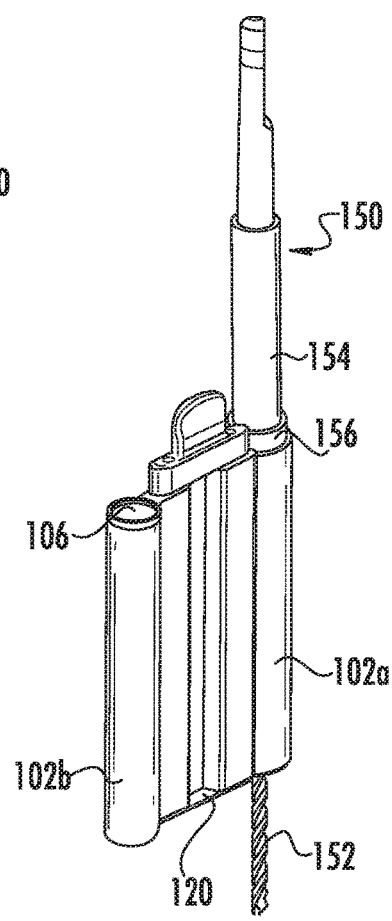
FIG. 10B is a perspective view of the first embodiment showing the drill abutted against the drill guide.
Figure 10C:
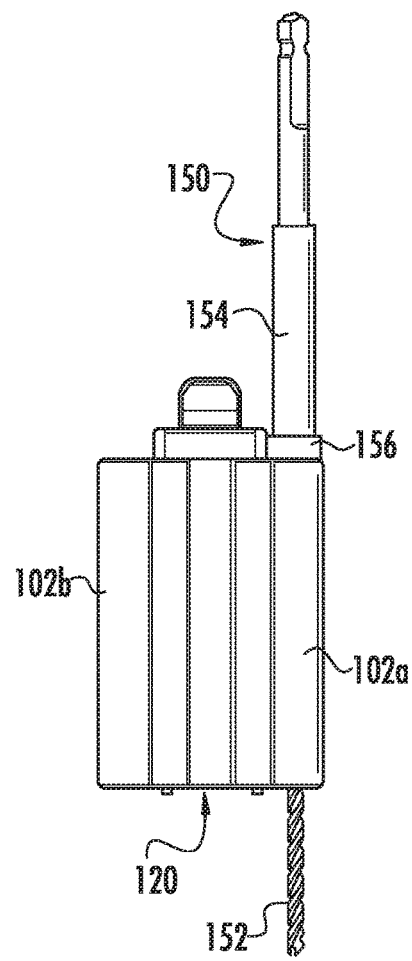
FIG. 10C is a front view of the first embodiment of FIG. 1 not shown on a bone showing a drill abutted against the drill guide.

FIG. 10A depicts an exemplary embodiment of the inserter assembly 100 and implant 120 while also showing preparation steps with drill 150 lined up with the internal diameter 106 of the tubes 102*a* and/or 102*b*. FIGS. 10A, 10B and 10C further show implant 120 controllably engaged to the tubes 102*a* and 102*b* with engagement pins 104*a* and 104*b* (pins not shown in image) engaged in engagement holes 122. Clip 110 is controllably maintaining the tubes relative to each other with the engagement pins 112 engaged in the tubes 102*a* and 102*b*. Drill 150 has a fluted region 152, a shaft 154 and a stop 156. FIGS. 10B and FIG. 10C show the drill stop 156 abutted against the top surface of the drill tube 102*a* or 102*b*. The stop 156 may be used to prevent the drill from extending too far into the bone during preparation. The stop 156 may be used to control the drill depth so the fluted region 152 only protrudes through the drill guide/tubes 102*a* and/or 102*b* to a predetermined depth.

In this exemplary embodiment the implant 120 may be made of a material that may have elastic or spring properties that allow the implant to have more than one configuration. FIG. 3 shows the implant 120 in a possible free-state or implanted-state of the device. The free-state or implanted-state may provide compression (or distraction) across bone members. FIG. 3 shows the implant 120 having a thickness 126 and a bridge member 124. It further shows the implant 120 having an arc or radius 128 while in its second configuration. FIG. 3 also shows an example of a bone attachment device 130, which in this case resembles a bone screw. The attachment device 130 is rigidly attached to the implant 120 through the attachment feature 129. The attachment feature 129 is such that it allows the bone attachment device to be locked to the material that may have elastic properties. The bridge member 124 depicted in FIG. 3 also has an engagement feature 122 for controllably engaging the inserter for maintaining the first configuration. The embodiment depicted thus far allows the implant 120 to be fully seated to the bone in its final position without the inserter interfering with this final position. When the implant is placed in its final position, it may or may not be in its second configuration. The implant may remain in a first configuration until the inserter is removed or further manipulation is performed.

FIG. 11 shows an exemplary embodiment of an implant 200 that resembles a bone staple. The implant is shown in a first configuration where the legs 220 are relatively parallel to each other. This first configuration may be useful in facilitating implantation of the implant 200 into bone. The first configuration may be the configuration that is maintained by an inserter. FIG. 11 depicts implant 200 having a bridge member 210 with a thickness 202. Thickness 202 may or may not be more or less than thickness 204. This particular embodiment shows the bridge member 210 has a radius 206. Radius 206 may or may not be present. FIG. 11 further shows legs 220 having a feature 230 for engaging an inserter. The engaging feature 230 may be an internal feature, external feature, may be positioned on the interior or exterior of the legs 220. It is also reasonable to have an engagement feature similar to engaging holes 122 in this type of device. Implant 200 has bone engagement means in the form of barbs 225 which engage the bone in order to maintain the implant in the bone. FIG. 12 shows the implant 200 of FIG. 11 in a second configuration. In this particular configuration of FIG. 12, the legs 220 converge towards each other. Either one or multiple legs may move to create this convergence or distraction. The second configuration may be the free-state or implanted-state.

Figure 13:
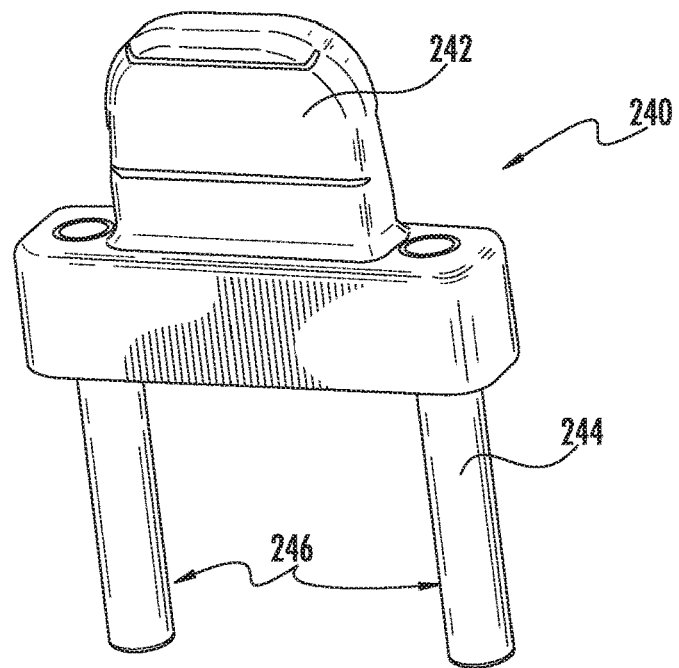
FIG. 13 is a perspective view of a second embodiment of an inserter.

FIG. 13 shows another embodiment of an inserter 240. Inserter 240 has a holding piece 242 and at least one engaging pin 244. The engaging pins 244 are spaced and oriented appropriately to interact with an implant to maintain a first configuration. FIG. 14 shows the inserter 240 assembled to an implant 200. The engaging pins 244 of inserter 240 engage the internal diameter of engaging feature 230 of implant 200 to maintain the implant 200 in a first configuration. When the inserter 240 is removed the implant assumes a second configuration as shown in FIG. 12.

Figure 15A:
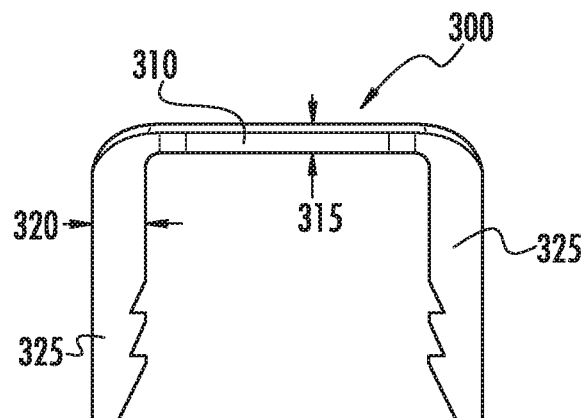
FIG. 15A is a front view of a third embodiment of an implant or fixation device in a first configuration.
Figure 15B:
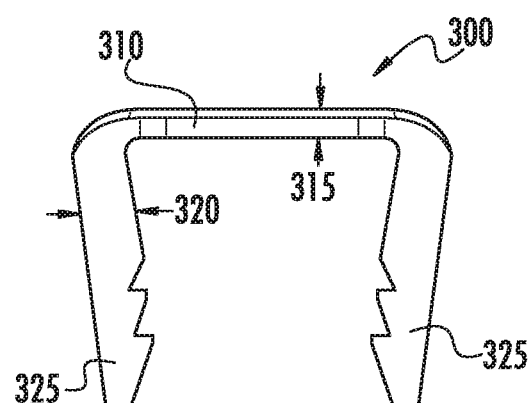
FIG. 15B is a front view of the third implant embodiment in FIG. 15A in a second configuration.
Figure 16A:
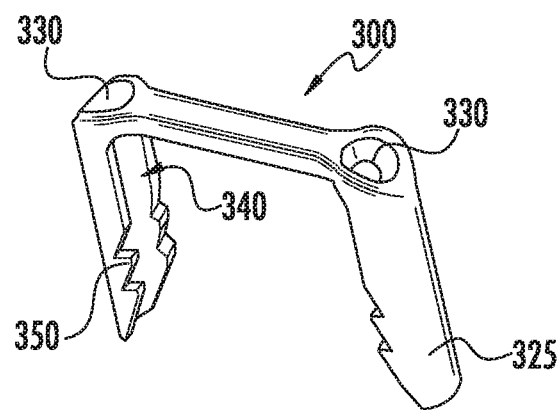
FIG. 16A is a perspective view of the third implant embodiment in FIG. 15A.
Figure 16B:
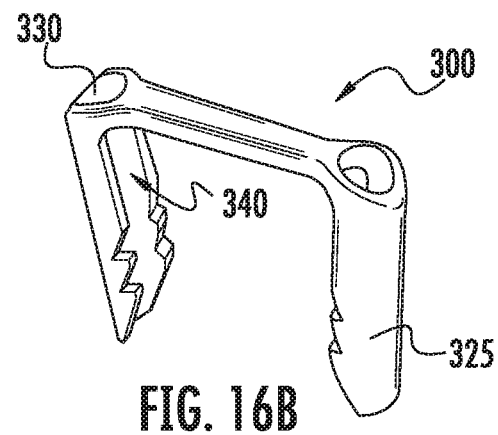
FIG. 16B is a perspective view of the third implant embodiment in FIG. 15B.

FIG. 15A shows yet another embodiment of an implant or fixation device 300. The implant 300 has a bridge member 310 and leg members 325. The bridge member 310 has a thickness 315 that may or may not be the same as the leg thickness 320. FIG. 15A shows the implant in a first configuration. FIG. 15B shows the implant 300 in a second configuration. The implant of FIGS. 15A and 15B is also shown in FIGS. 16A and 16B depicting an internal diameter 330. Opening 340 is generated by the internal diameter 330 breaking out into the inside of the leg. The opening 340 may or may not be needed for this current technology. The internal diameter 330 may be used to engage the inserter and maintain the implant in a particular configuration. The internal diameter 330 may also be used to manipulate the implant into another configuration whereas the relationship between the implant legs 325 is changed by creating convergence, divergence or some other out of plane relationship.

Alternate embodiments may include an inserter and implant that work in conjunction to create a first and second configuration.

Figure 17A:
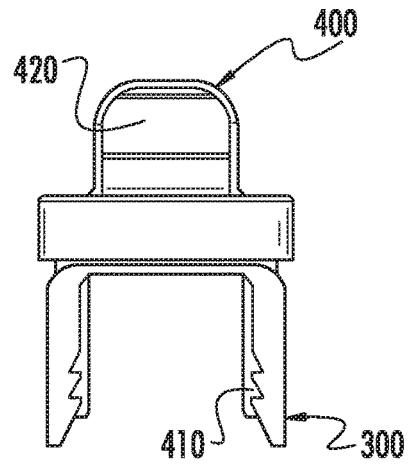
FIG. 17A is a front view of the third embodiment of an implant assembled to the third embodiment of the inserter.
Figure 17B:
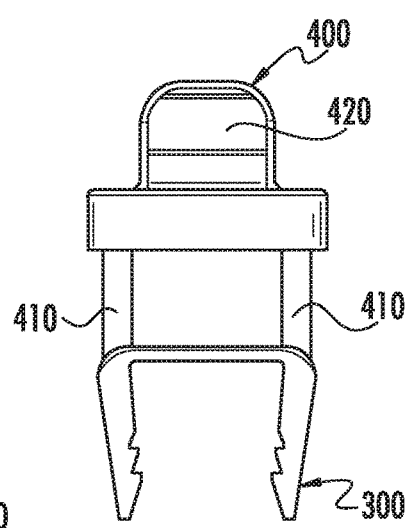
FIG. 17B is a front view of the third embodiment of the implant at the end of engagement to the third embodiment of the inserter.
Figure 17C:
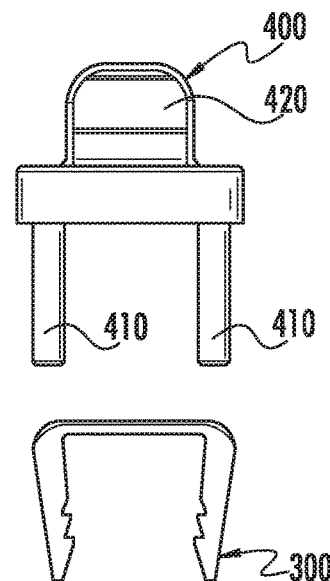
FIG. 17C is a front view of the third embodiment of the implant separated from the third embodiment of the inserter.
Figure 18A:
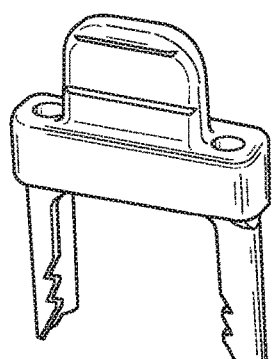
FIG. 18A is a perspective view of FIG. 17A.
Figure 18B:
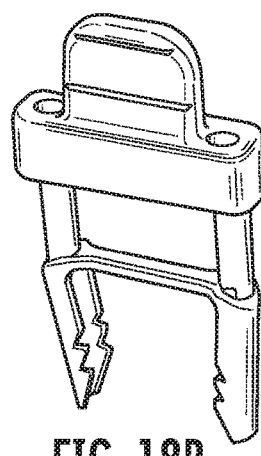
FIG. 18B is a perspective view of FIG. 17B.
Figure 18C:
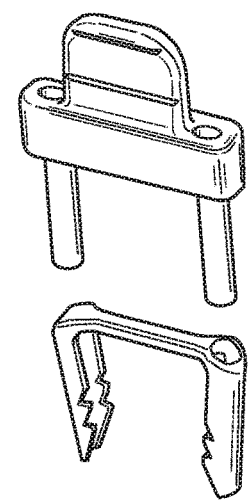
FIG. 18C is a perspective view of FIG. 17C.

FIG. 17A shows an embodiment of an implant 300 on an inserter 400 with the implant being in a first configuration. FIG. 17B shows the same embodiment with the implant 300 at the end of the engagement pins 410 of the inserter 400. The implant in FIG. 17B is transitioning to a second configuration. FIG. 17C shows the implant 300 fully disengaged from the inserter 400. The implant 300 is in a second configuration. FIGS. 18A, 18B and 18C depict the embodiments in FIGS. 17A, 17B and 17C in a perspective view.

The embodiments shown herein depict the engagement between the implant and inserter as using pins. Those skilled in the art will appreciate that various means may be used to attach the implant to the inserter.

Figure 20:
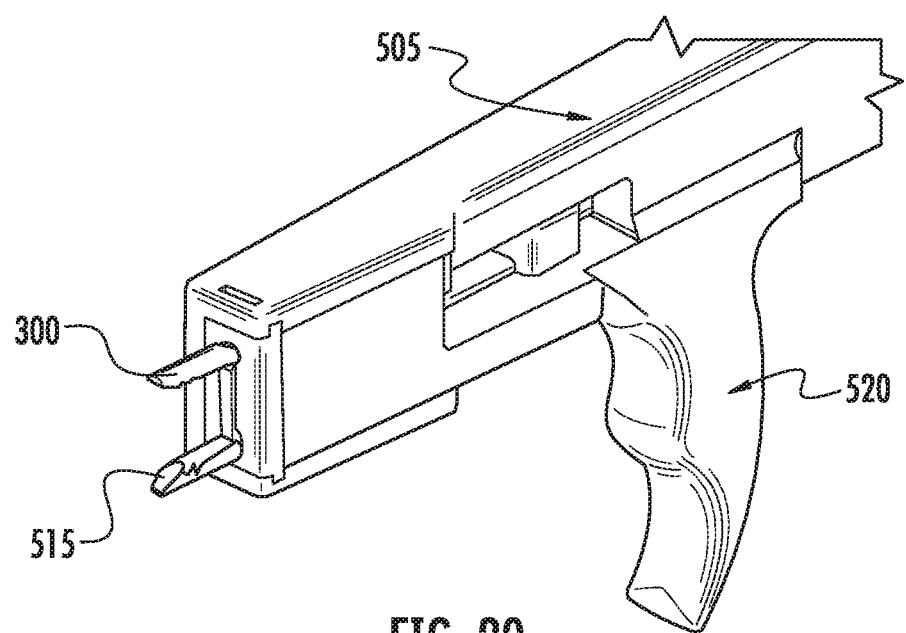
FIG. 20 is a close up view of the working tip of the fourth embodiment depicted in FIG. 19.

FIGS. 19 and 20 depict an embodiment of an inserter 500 that is preassembled to an implant 300. The inserter 500 has a holding means 510 and an impact or seating means 530. Handle 520 is slide-ably engaged in the body 505. The inserter assembly 500 has means for engaging an implant, 515. In this embodiment the engaging means are pins 515. Pins 515 are connected to handle 520 such that the pins will retract from implant 300 thereby ejecting or releasing the implant from the inserter assembly 500. In this embodiment the pins or engagement means are retractable. Those skilled in the art will appreciate that the same effect can be achieved without retractable engagement means where the implant may be pushed off the engagement means with a plunger type mechanism that may push the implant off or from the inserter assembly.

Figure 21:
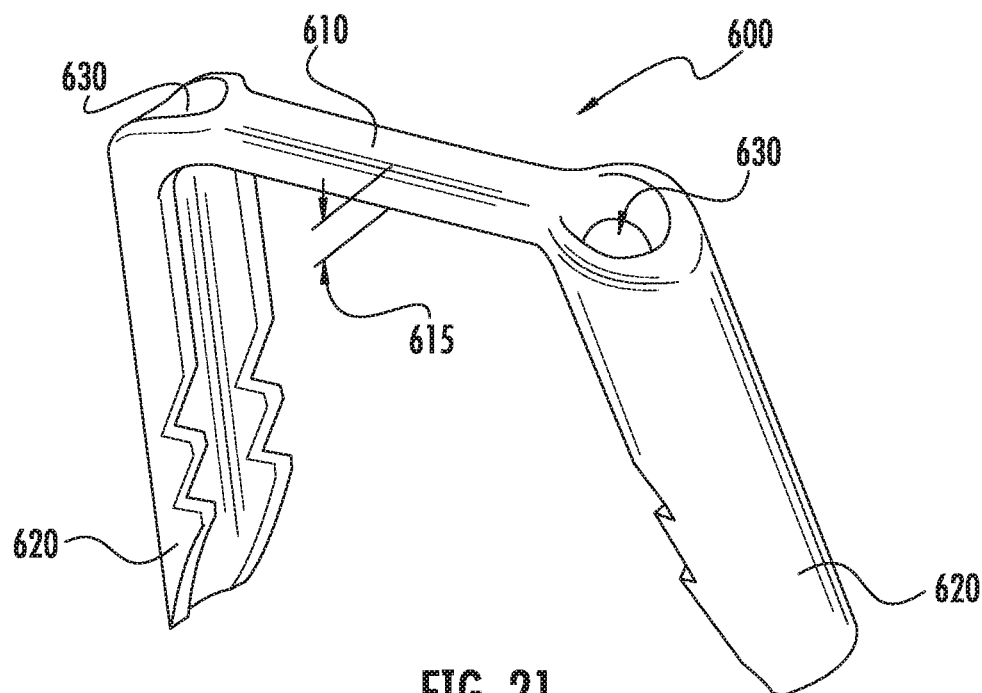
FIG. 21 is a perspective view of a fifth embodiment of an implant in an alternate configuration with the legs or fixation members out of plane relative to each other.
Figure 22:
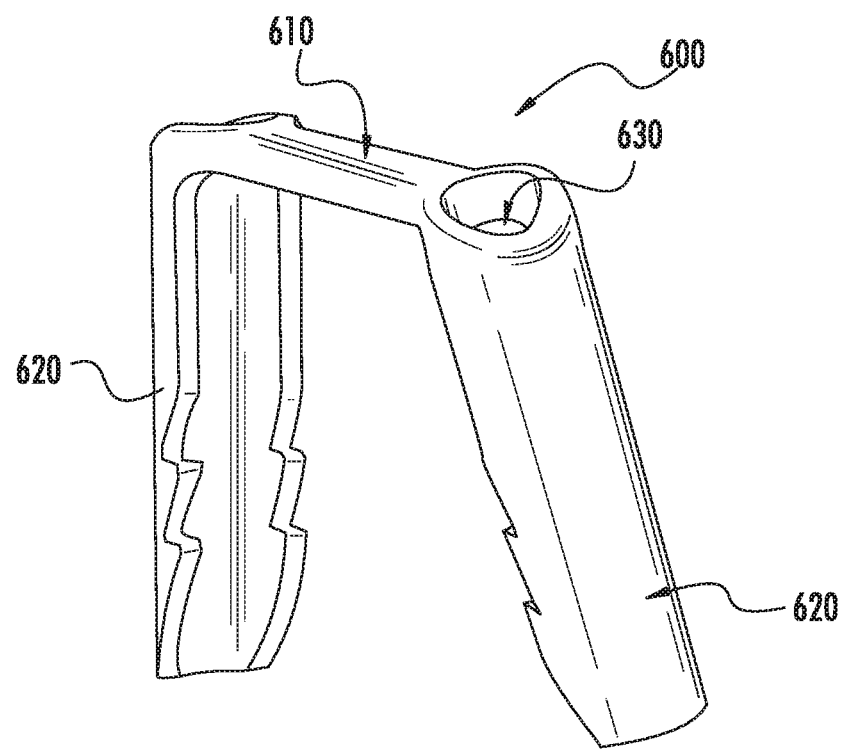
FIG. 22 is another perspective view of the implant in FIG. 21 showing an alternate configuration with the legs or fixation members out of plane relative to each other.

FIGS. 21 and 22 show an embodiment of an implant 600 in an alternate configuration. This embodiment resembles a bone staple, but those skilled in the art will appreciated that this embodiment could also be achieved with modular fixation means such as bone screws. The implant 600 has a bridge member 610 with thickness 615. The bridge member 610 is connected to fixation members or legs 620. Legs 620 are out of plane relative to each other. Legs 620 may or may not be out of plane relative to the bridge member 610. The implant 600 may have engaging features 630 to control and/or manipulate the implant into alternate configurations. The engaging features 630 may or may not extend through the entire implant. The engaging features 630 may be positive or negative features in the implant or inserter. This alternate configuration may or may not be achieved through the inherent material properties of the implant material. The implant may achieve this alternate configuration by transitioning from, for example, configuration 1 to configuration 2 to configuration 3. Where configuration 1 may be that as attached to the inserter or delivery instrument and configuration 2 may be a configuration where the leg members 620 are in a compressed state and where configuration 3 may be a configuration where the compressed legs of configuration 2 are made to be out of plane to each other. Alternately, the implant may achieve this alternate configuration by transitioning from, for example, configuration 1 to configuration 2. Where configuration 1 may be that as attached to the inserter or delivery instrument and configuration 2 may be a configuration where the leg members 620 are in a compressed state and are made to be out of plane to each other. This embodiment is not intended to be limiting. The transition from one configuration to another configuration may be one distinct transition or more than one distinct transition. The transition may be due to the inherent material properties or achieved by a manipulation of the material or a combination thereof.

The embodiments described herein can be manufactured from a number of different materials or combinations of materials. Nitinol, for example, possess material properties, such as shape memory and/or super elasticity that may provide the inherent properties to allow an embodiment to have multiple configurations with or without an external mechanical manipulation. Stainless steel and/or titanium also have desirable material properties for the embodiments described herein. Stainless steel and/or titanium may not possess shape memory or super elasticity, but may possess the mechanical properties for embodiments that may benefit from mechanical manipulation to achieve multiple configurations. Still other materials such as PEEK or other polymers may also possess material properties beneficial for the embodiment described herein. A combination of materials may also be preferred. For example, a nitinol plate with titanium screws may be the materials of choice for some embodiments. Those skilled in the art are aware of the typical materials and combinations of materials applicable to the current technology.

Yet another embodiment of this technology may have the implant assembled onto a holding means such as an apparatus or carrier that may be assembled to an inserter at the time of surgery, as shown in FIGS. 23A, 23B, 24, and 25-28.

Figure 23A:
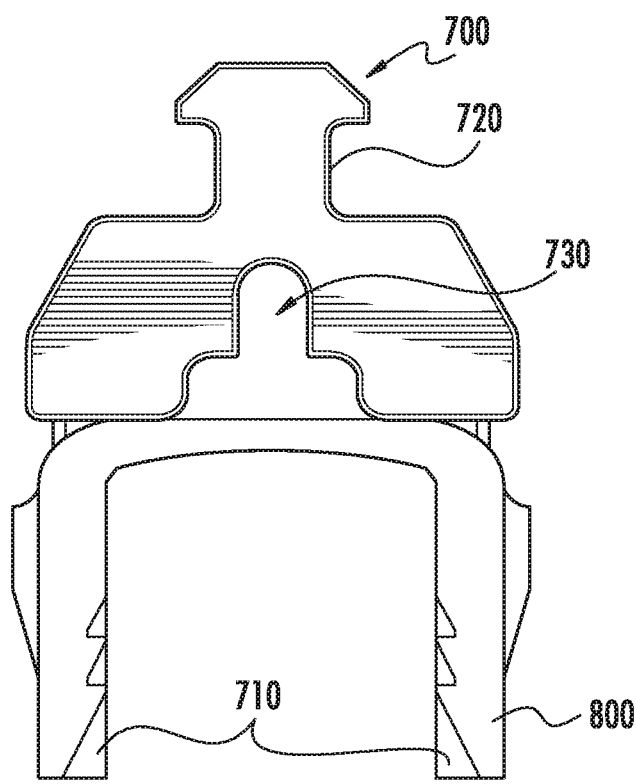
FIG. 23A is a front view of an implant of a sixth embodiment assembled to an implant carrier.
Figure 23B:
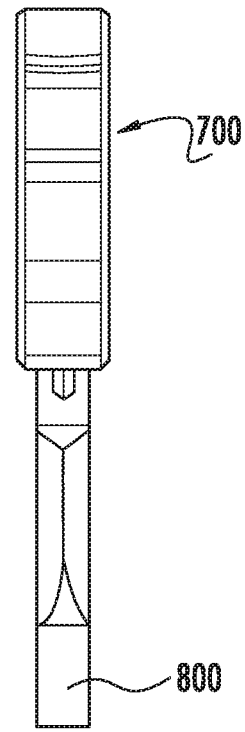
FIG. 23B is a side view of the implant and implant carrier of FIG. 23A.
Figure 24:
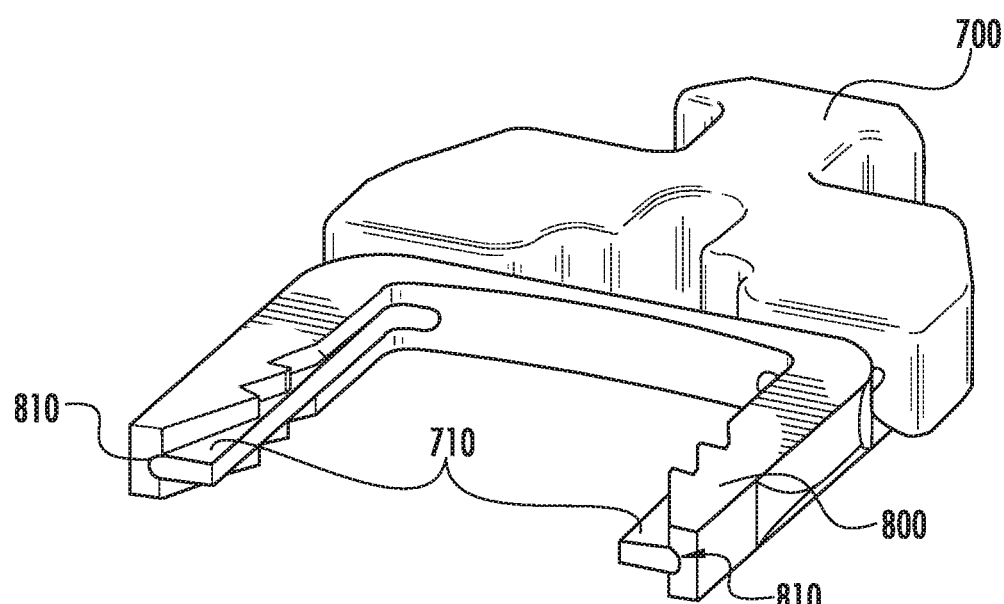
FIG. 24 is an isometric view of the sixth embodiment of the implant and implant carrier assembly shown in FIGS. 23A and 23B.

FIGS. 23A and 23B show an exemplary embodiment of an implant carrier, 700, assembled to an implant embodiment, 800. FIG. 23A is a front view of the assembly and FIG. 23B is a side view of the assembly. FIG. 24 shows the carrier, 700, slidably engaged to the implant, 800. Implant 800 has features 810 for receiving the engaging features 710 of the carrier. The carrier 700 may have features and/or geometries 720 for engaging the inserter. The carrier 700 may have features and/or geometries 730 for additionally engaging the inserter. The engaging features and or geometries 720 and 730 may be used separately or in combination to provide a poka-yoke feature that prevents incorrect assembly of the carrier to the inserter. Features 720 and or 730 may also be used to assist the inserter in removing the carrier from the implant, i.e. releasing the implant from the carrier, at the time of implantation. The carrier 700 may be configured to fit multiple sized implants. The engaging features 710 of the carrier 700 may change from size to size in order to optimize the fit between the implant 800 and carrier 700. The engaging features (e.g. 720 and 730) of the carrier may or may not change by implant size. Keeping such features consistent among varying implant sizes may allow the use of multiple implant carriers with the same inserter.

Figure 25:
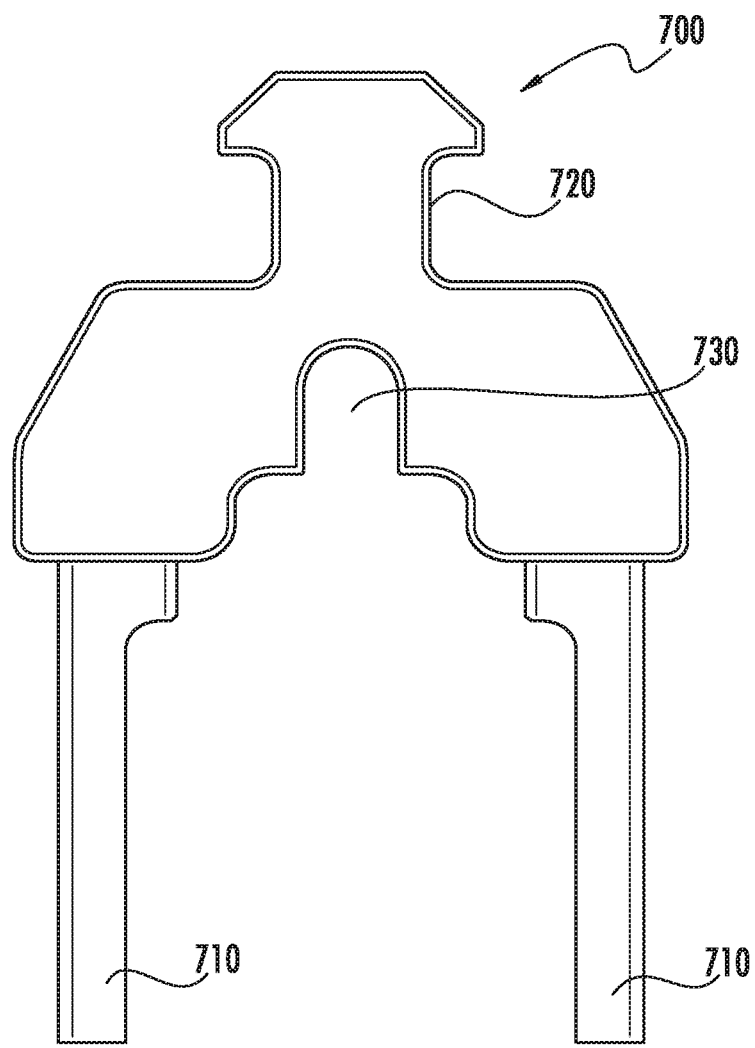
FIG. 25 is a front view of the implant carrier of the sixth embodiment shown in FIG. 24 without the implant assembled to it.

FIG. 25 more clearly shows the carrier 700 without an implant assembled. As previously described the carrier 700 has features 710 for slidably or by other means attaching and securing the implant in position on the carrier. The inserter engaging feature 720 may have multiple configurations or geometries. The engaging feature 720 may provide an engagement with the inserter that allows the inserter to retract the carrier from the implant 800. Engaging feature 730 may also be used to attach to the inserter and may provide a poka-yoke feature to prevent improper assembly of the carrier 700 to an inserter. To those skilled in the art, it will be apparent that the function of features 720 and 730 may be combined or alternated to achieve the same purpose and function described in this embodiment.

Figure 26A:
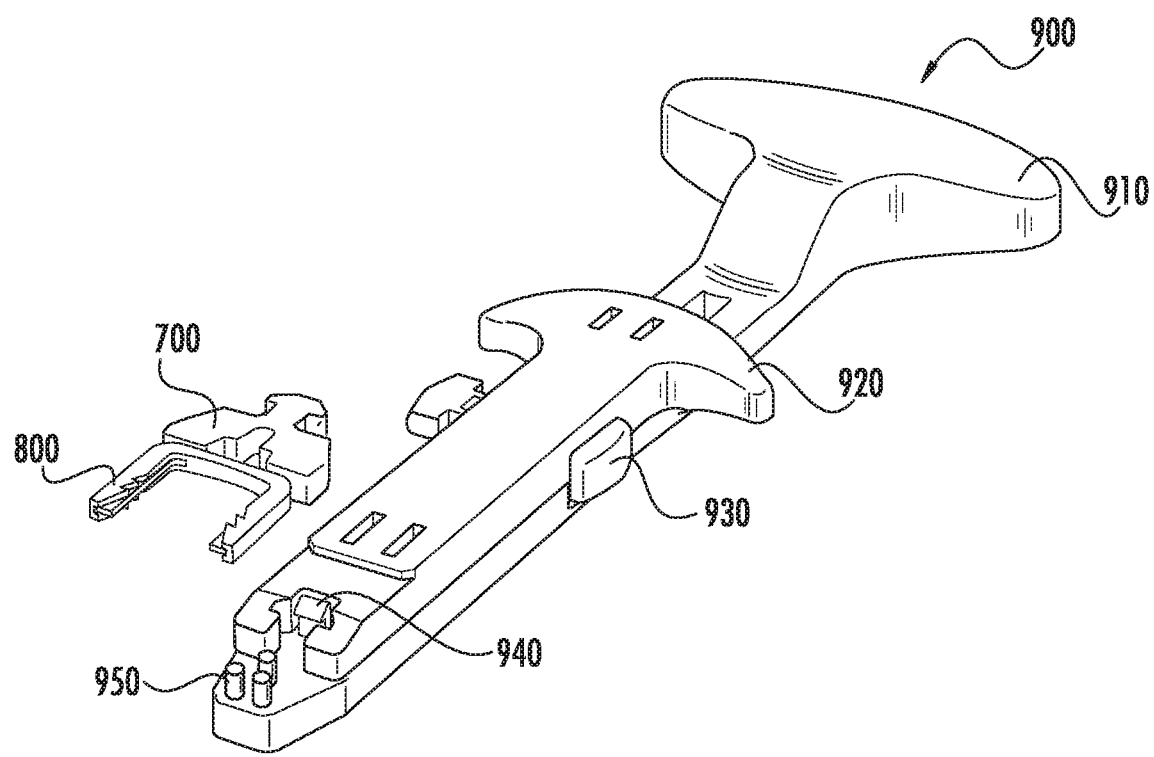
FIG. 26A is an isometric view showing the inserter and an implant/carrier assembly of the sixth embodiment prior to installing the carrier to the inserter.
Figure 26B:
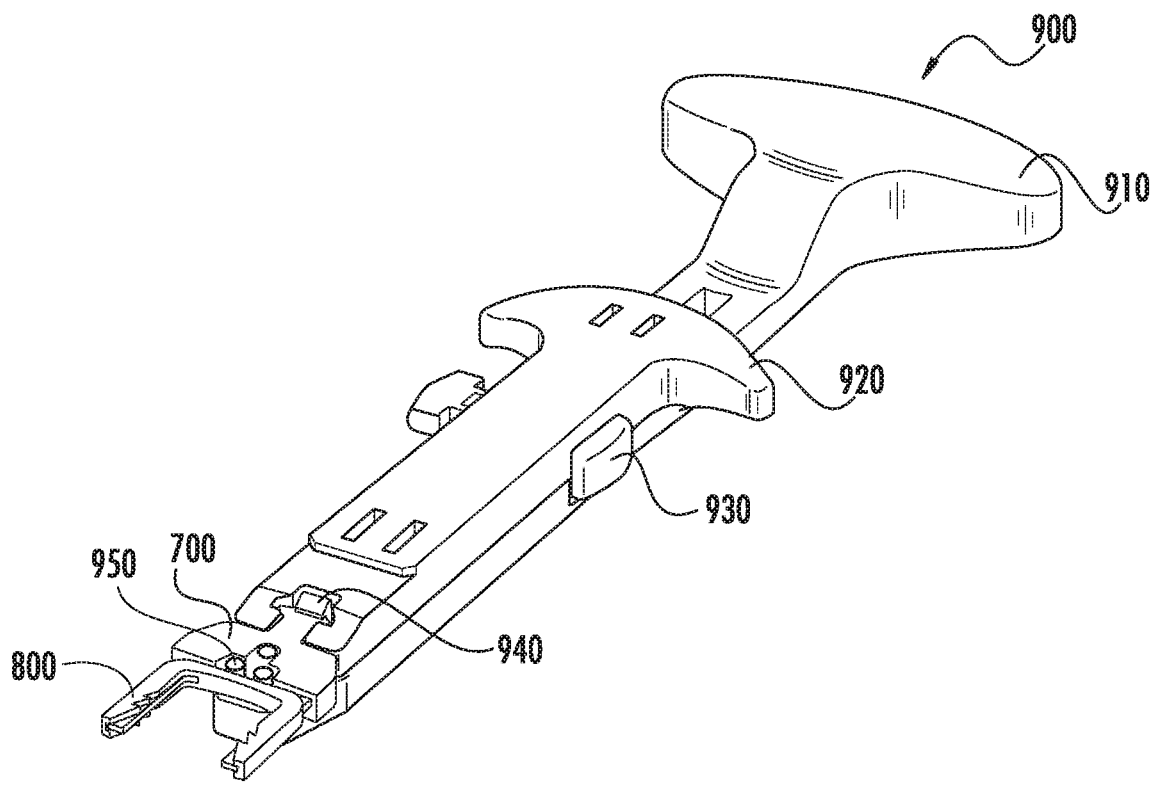
FIG. 26B is an isometric view of the sixth embodiment shown in FIG. 26A further showing the implant/carrier assembled to the inserter.

FIGS. 26A and 26B show an exemplary embodiment of an inserter 900 and the implant 800 assembled to the carrier 700. FIG. 26A shows the inserter 900 with the implant carrier 700 prior to assembling the carrier 700 to the inserter 900. FIG. 26B shows the carrier 700 with the attached implant 800 assembled to the inserter 900. In this exemplary embodiment the inserter 900 has a base component 910, a handle component 920 and a locking means 930. The inserter also may have a retaining member 940 that may be used for assisting in maintaining the carrier 700 in a specified position. Retaining member 940 may or may not be integrated into the handle component 920. This inserter embodiment has features 950 for engaging with the carrier 700 in a poka-yoke means. The locking means 930 may be used to secure the handle component 920 to the base component 910.

Figure 27A:
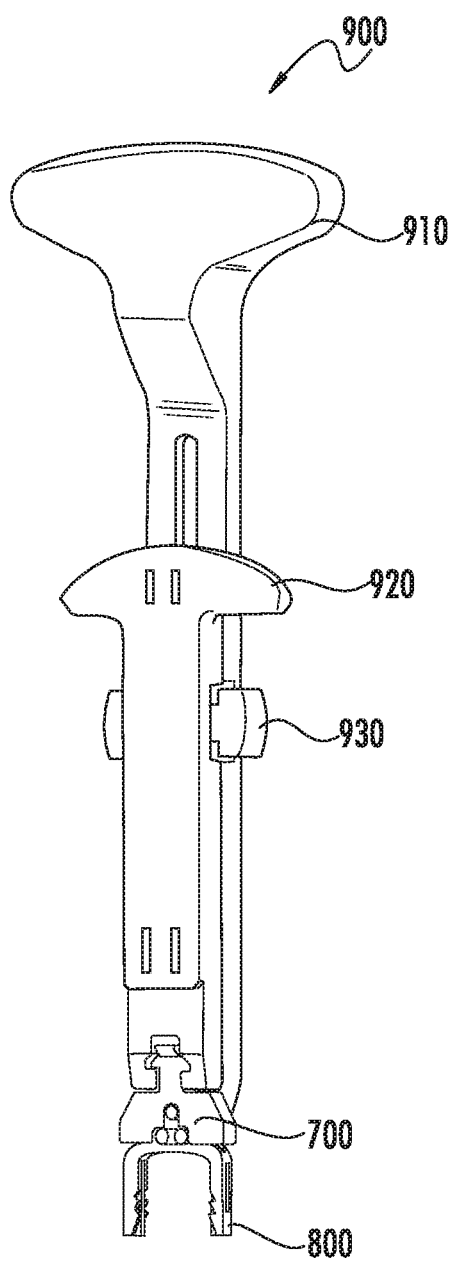
FIG. 27A is an isometric view showing the sixth embodiment of FIG. 26 prior to releasing the implant from the inserter and carrier.
Figure 27B:
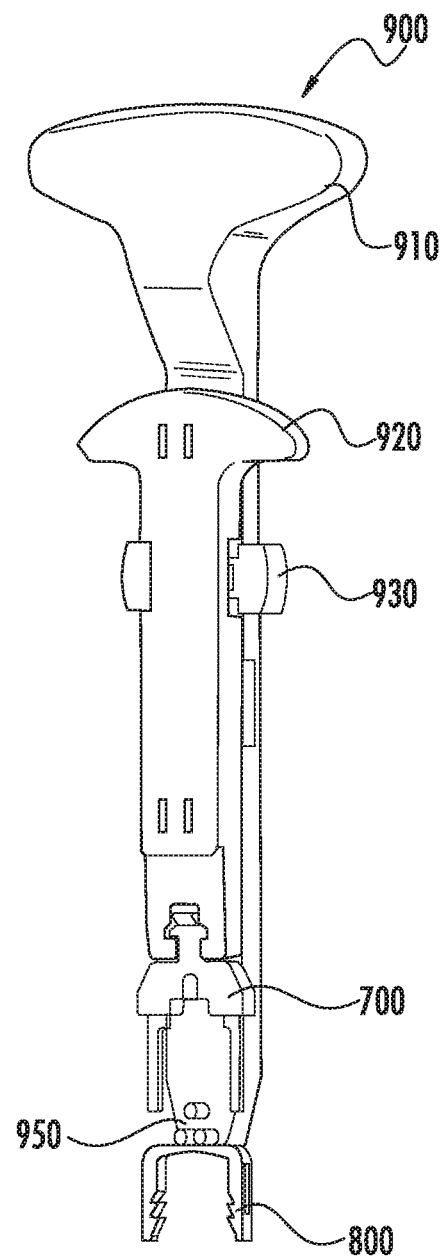
FIG. 27B is an isometric view showing the sixth embodiment of FIG. 26 after releasing the implant from the carrier, further showing the implant released from the carrier and the carrier still engaged with the inserter.

FIGS. 27A and 27B show the exemplary embodiments of FIGS. 26A and 26B in an upright isometric view. FIG. 27A shows the carrier 700 and implant 800 attached to the inserter 900 prior to releasing the implant 800 from its carrier 700. FIG. 27B demonstrates one embodiment for releasing the implant 800 from the carrier 700. FIG. 27B shows the handle 920 in a retracted position that removes the carrier 700 from the implant 800. In the state shown in FIG. 27B the implant is now free from the carrier 700. The carrier 700 may be removed from the inserter 900 and replaced with another implant/carrier assembly.

Figure 28:
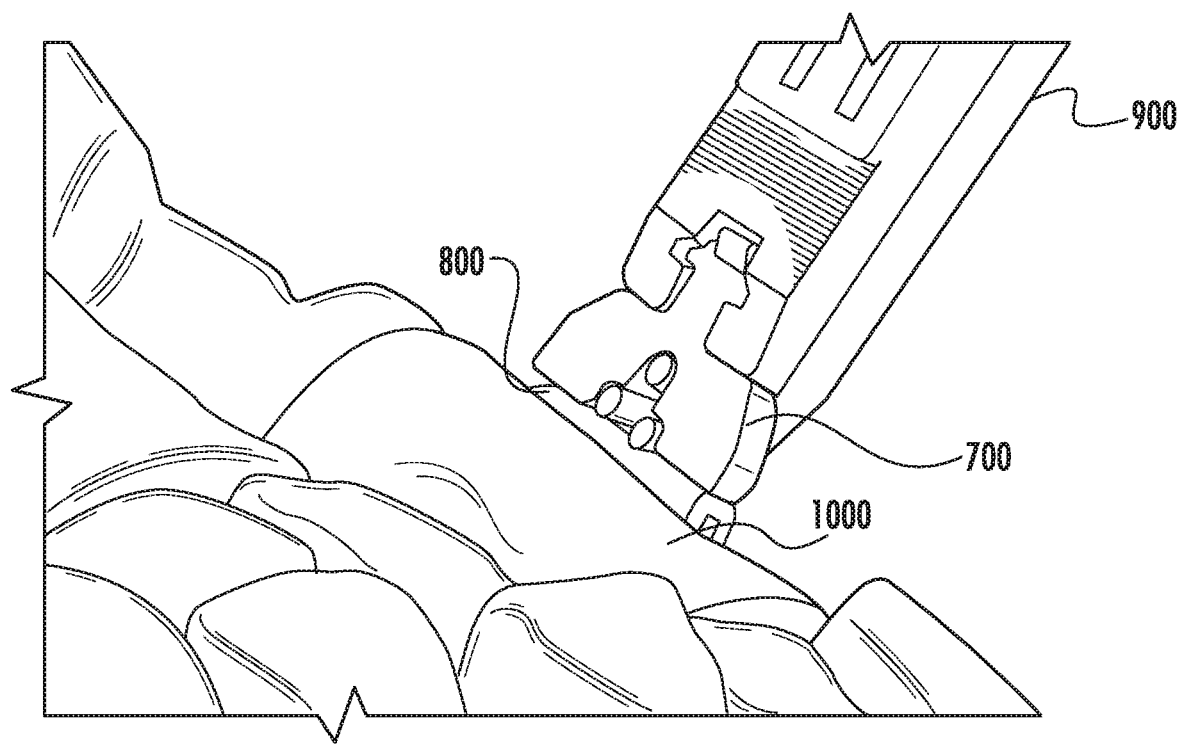
FIG. 28 shows the sixth embodiment further depicting the implant, assembled to the inserter via the carrier, being fully seated on the bone, further showing that the inserter and carrier do not interfere with the placement of the implant in its final position.

FIG. 28 demonstrates the exemplary embodiments of the inserter 900, the carrier 700 and the implant 800 allowing the implant 800 to be seated flush against a bone surface 1000. One will notice that the inserter 900 does not interfere with the final placement of the implant 800. For an implant 800 having a second configuration where the parallel legs are allowed to converge after releasing from the inserter 900 and carrier 700, not having to perform a secondary final seating of the implant after release from an inserting device is beneficial.

Figure 29:
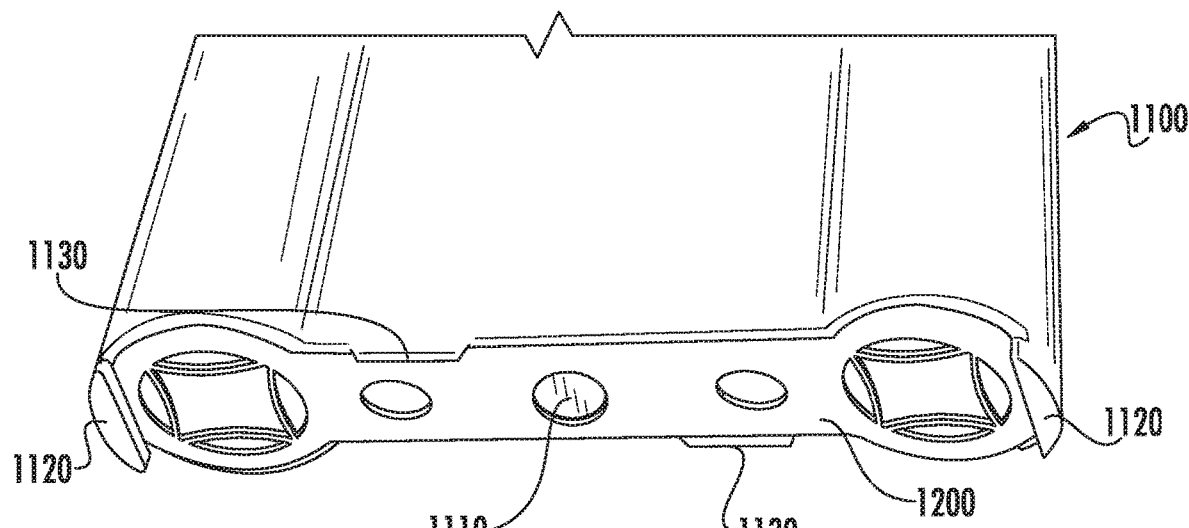
FIG. 29 is a close-up view of the implant/inserter interface of a seventh embodiment depicting an implant assembled to the inserter further showing the inserter engaging the periphery of the implant thereby not interfering with the final seating of the implant.
Figure 30:
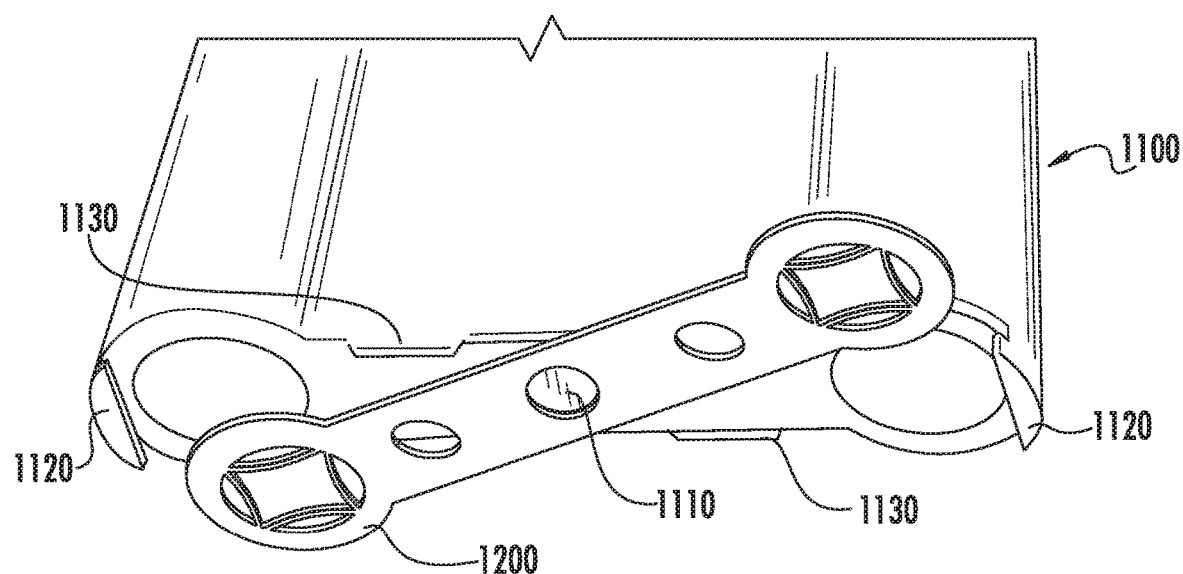
FIG. 30 shows the seventh embodiment of FIG. 29 depicting the inserter being released from the implant by rotating the inserter off the implant.

FIG. 29 shows a close-up view of the implant/inserter interface of another exemplary embodiment of an inserter 1100 and an implant 1200. The inserter 1100 has means 1120, 1130 and 1110 for attaching to the implant. These attachment means engage the implant 1200 in such a way to not prohibit final seating of the implant 1200 in its final desired position. FIG. 30 shows one possible means for releasing the implant 1200 from the inserter 1100. This embodiment demonstrates a rotation of the inserter 1100 relative to the implant 1200. This rotation releasing the engaging means 1120 and 1130 while rotating about the pin 1110. Once fully rotated and released the inserter 1100 can be removed from implant 1200.

Figure 31:
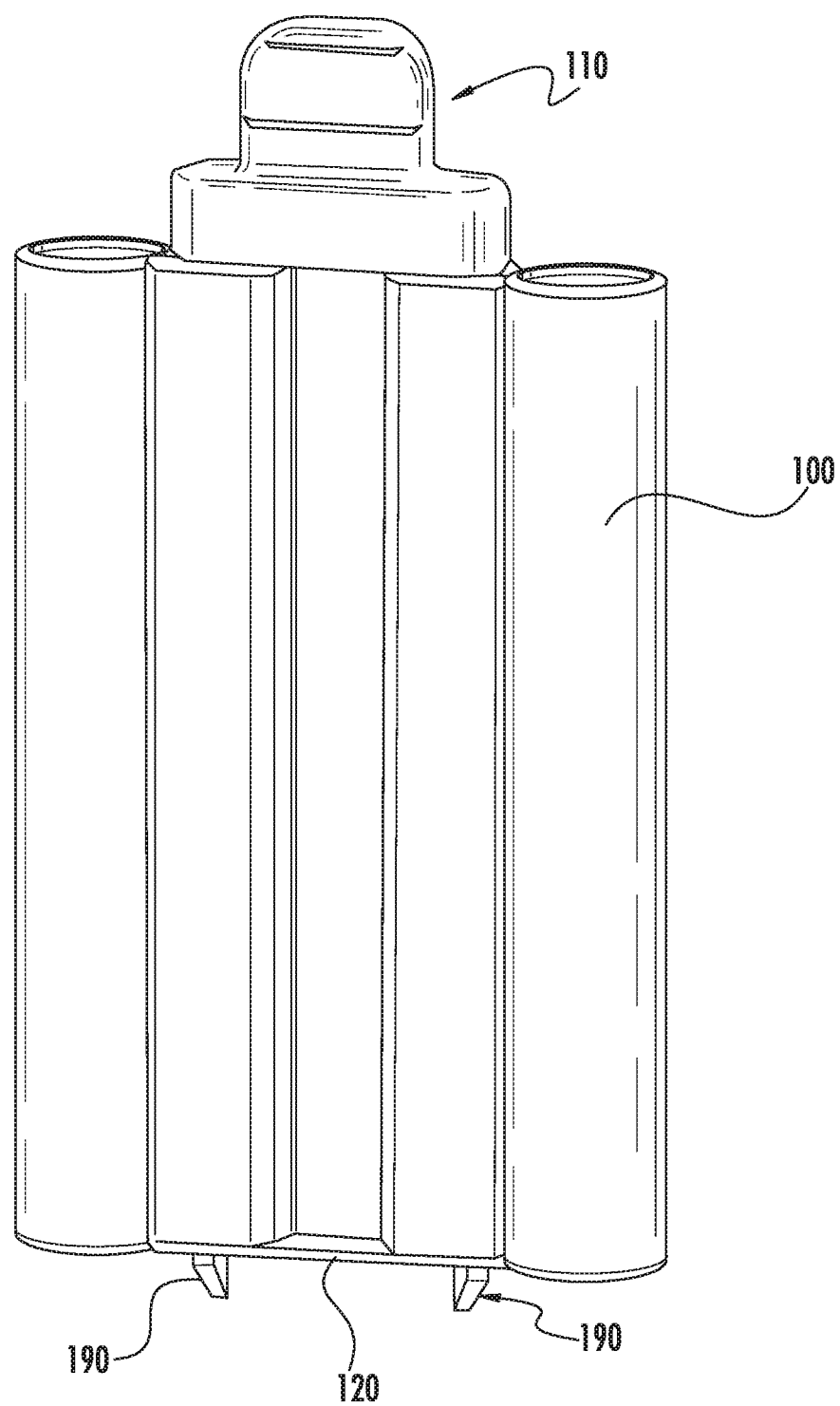
FIG. 31 shows an eighth embodiment of the current technology with engaging members extending through an implant for provisional fixation on the bone surface.

FIG. 31 shows the previously described inserter embodiment 100 and clip 110 assembled to implant 120. It further shows an embodiment of the engaging means 190 that may purposely extend beyond the implant 120. The engaging means 190 shown may have tips that are configured to penetrate into a bone surface to provide provisional fixation.

FIG. 32 depicts an embodiment of the implant 1600 which includes multiple connection means (means for fixation to a bone) 1620 for receiving bone engaging members. The bone engaging members may be bone screws, pegs, blades or other means suitable for engaging bone or soft tissue. The connection means 1620 may be of the same or varying styles or geometries for a particular implant. For example, some of the connection means 1620 in implant 1600 may be threaded and or locking while others may be non-threaded or non-locking. Implant 1600 has a bridge area 1601 spanning between the connection means 1620. The bridge area 1601 may or may not have multiple rails or members 1602. This particular embodiment depicts two rail members 1602 defining a space 1603 with a perimeter 1645. As further shown in FIG. 33 the space 1603 has lower surfaces 1641 and 1642 that are recessed from the bottom surface 1640. Lower surfaces 1641 and 1642 may be of similar or different configurations and or geometries suitable for engaging a means of insertion. FIG. 34 depicts an inserter 1650 that is engaged with the implant 1600. Inserter 1650 has two members 1652 and 1651 with a space 1655 therein. FIG. 34 shows the implant 1600 held in a first configuration which may or may not be flat. This first configuration may facilitate the surgical implantation. This first configuration may act to store a compressive force or other force. FIG. 35 shows the inserter 1650 partially disengaged from implant 1600. The members 1651 and 1652 may come together thereby reducing the space 1655 that may enable or facilitate assembly and or disassembly of the inserter 1650 and implant 1600. As depicted in FIG. 35 as the inserter 1650 is disengaged from the implant 1600 the implant is allowed to take on a second configuration. This second configuration may be achieved by the design of the implant 1600 and or in combination with the intrinsic material properties of the implant and or in combination with the processing of the implant 1600. This second configuration may act to create a compressive force or other force across one or two bone or tissue segments.

Figure 36:
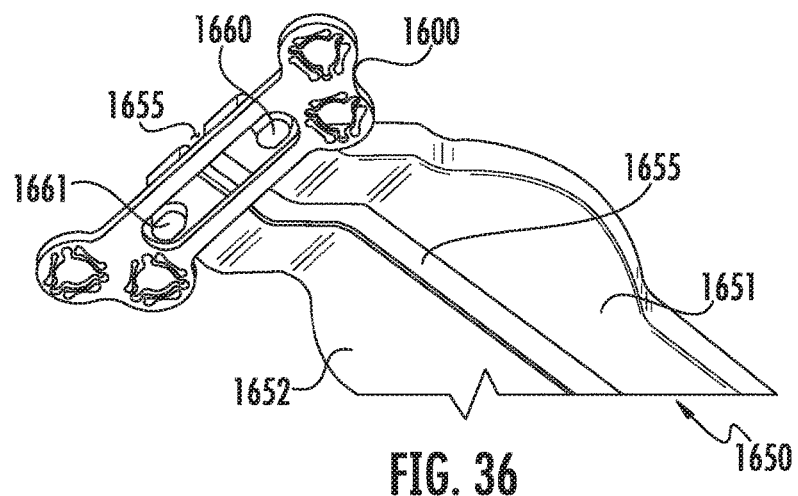
FIG. 36 is a bottom perspective view of the implant-inserter assembly depicted in FIG. 34.

FIG. 36 depicts the implant 1600 releasably attached to the inserter 1650. The implant engaging means 1660 and 1661 of the inserter 1650 may engage the implant 1600 by interfacing the implant surface 1641 and 1642. The arms of the inserter 1651 and 1652 may pass through space 1603 to engage the implant 1600.

Figure 37A:
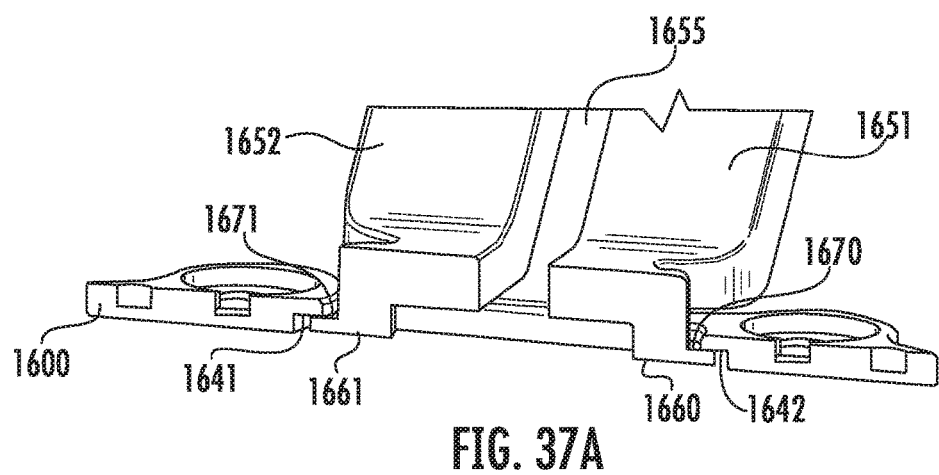
FIG. 37A is a section view of the implant-inserter assembly depicted in FIG. 34.
Figure 37B:
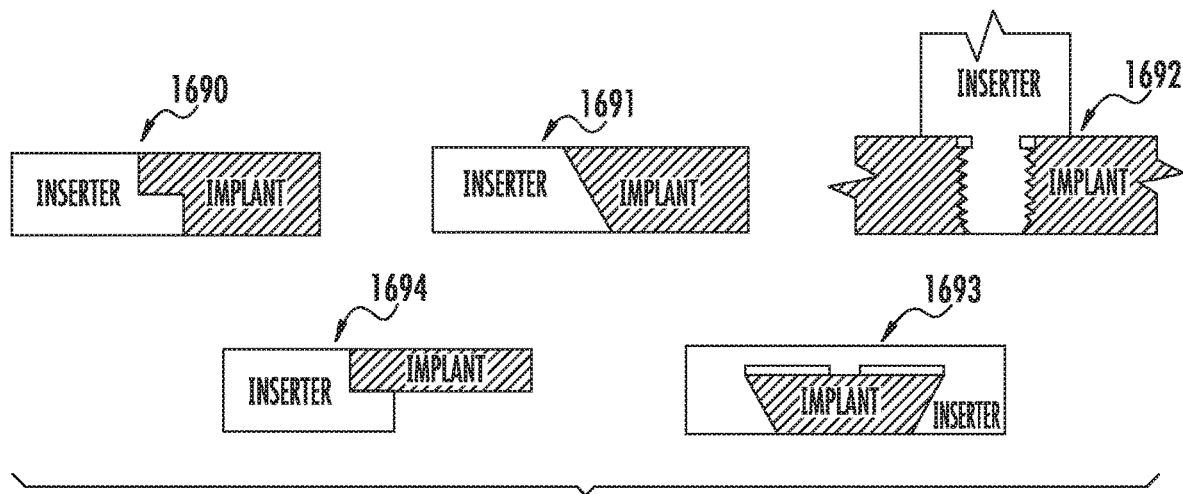
FIG. 37B depicts alternate geometries for various means of insertion.

FIG. 37A depicts a possible cross section of the implant-inserter combination. The implant is shown in a first configuration. The arms 1651 and 1652 of the inserter 1650 may pass through space 1603 of the implant thereby allowing the upper surfaces 1670 and 1671 of the engaging members 1660 and 1661 to interface with the lower surfaces 1641 and 1642 of implant 1600. Once engaged the inserter arms 1651 and 1652 may provide a force that maintains the implant in a first configuration. In this exemplary embodiment the inserter 1650 is depicted passing through an internal space 1603 of implant 1600. In other embodiments the inserter may engage on an external feature as will be demonstrated herein. In the current embodiment, the general shape of the engagement is depicted as an "L" shape interface. However to those skilled in the art it is apparent that numerous geometries and configuration or combination of geometries and configurations that are possible and may be encompassed by the current technology. FIG. 37B depicts several possible alternative geometries for connection to a means of insertion that may be used to maintain a particular implant configuration. FIG. 37B depicts geometry 1690 which may be generally "L" shaped. FIG. 37B depicts geometry 1691 which may be generally angled faces or tapered faces or chamfered edges. FIG. 37B depicts geometry 1692 which may be generally a threaded or other fastening geometry. FIG. 37B depicts geometry 1693 which may generally represent a bending modality that may utilize specific geometries in combination with locations on an implant surface to maintain a particular implant configuration. FIG. 37B depicts geometry 1694 which generally may be a combination of a square geometry and a "L" shaped geometry. The means of insertion may or may not be flush with the implant. A combination of features may be used to maintain an implant in a particular configuration or combination of configurations. Certain combinations may be used to hold certain implant features in a configuration that may or may not be the same as the entire implant. For example, certain features or combinations of features may be used to hold one arm or projection of an implant in an upward direction while another feature or combination of features may be used to hold a different arm or projection or portion of an implant in a downward direction. This may allow certain aspects of an implant to achieve various configurations. The connection between an implant and inserter and the means of insertion my hold the implant in a first configuration and or an alternate configuration. As the inserter and implant are disassembled, the disassembly may allow the implant to achieve a second or alternative configuration. This disassembly may allow the implant to achieve multiple alternative configurations. For example, step 1 of the disassembly may allow the implant to achieve a second configuration and step 2 may allow the implant to achieve a third configuration and step 3 of the disassembly may allow the implant to achieve a fourth configuration. This disassembly may allow the implant or portions of the implant to achieve multiple alternative configurations. For example, step 1 of the disassembly may allow the portion A of the implant to achieve a second configuration and step 2 may allow portion B of the implant to achieve an alternate configuration and step 3 of the disassembly may allow portion C of the implant to achieve an alternate configuration. Those skilled in the art will understand that combinations of alternate configurations of an implant or portions of an implant may be possible with the current technology. Certain alternate configurations may be intermediate configurations that will revert to a previous configuration or may proceed to a final configuration once fully disassembled from the inserter. The embodiments described herein do not limit the scope of the current technology. Further embodiments and combinations of embodiment may be possible and will become evident to those skilled in the art. The current technology may include an inserter and inserter-implant combination that may be used with an implant that has one or more configurations.

An implant of the current technology may be assembled to an inserter or other delivery instrument by several means that will be evident to those skilled in the art. The implant may be pre-assembled in the packaging or assembled at the time of use. The implant may be predisposed to a first configuration then assembled to an inserter. The implant may be predisposed by various means to achieve a first configuration for assembly with an inserter. Alternatively, an implant may be predisposed by various means to achieve a pre-assembly configuration for assembly with an inserter whereas the pre-assembly configuration may or may not be equivalent to the first configuration or second configuration. The implant may be predisposed by various means to achieve this alternate configuration for assembly with an inserter or other delivery instrument which may include physical deformation of the implant such as bending or mechanical manipulation, for example applying a force to the implant on a flat surface or other surface to temporarily hold the implant in a shape for assembly to the inserter. The implant may be predisposed by various means to achieve this alternate configuration for assembly with an inserter which may include application of an external temperature change, either by heating, cooling and or freezing the implant that may create a change in the physical properties of the material such as to facilitate an alternate configuration for assembly. The implant may be predisposed by various means to achieve this alternate configuration for assembly or re-assembly with an inserter which may include assembly or re-assembly at the time of use. If an implant is already positioned or implanted, either partially or fully, the implant may be in a sufficient configuration that would allow re-assembly of the inserter or other instruments. This may have advantages over existing technologies and may be beneficial in allowing an implant to be removed, repositioned or otherwise adjusted. In addition, the advantages of the current technology may include the ability for the end user to assemble a multi configuration implant to an instrument at the time of use. As shown in the embodiments described herein, the inserter may be designed to provide a means for assembly; a means for maintaining a first implant configuration; and or a means for delivering an implant and achieving an alternate configuration. The instrument may include features such as chamfers, ramps, steps, shoulders, mechanical levers, mechanical interfaces, complementary geometries, etc. for manipulating an implant from an alternate configuration to a first configuration for means of assembly and maintaining a first configuration. The means of assembly may be achieved by a single feature or multiple features on a single inserter or delivery instrument. The means of assembly may be achieved by a single feature or multiple features on a single inserter or delivery instrument or by the use of multiple delivery instruments used sequentially or simultaneously in combination.

Figure 38:
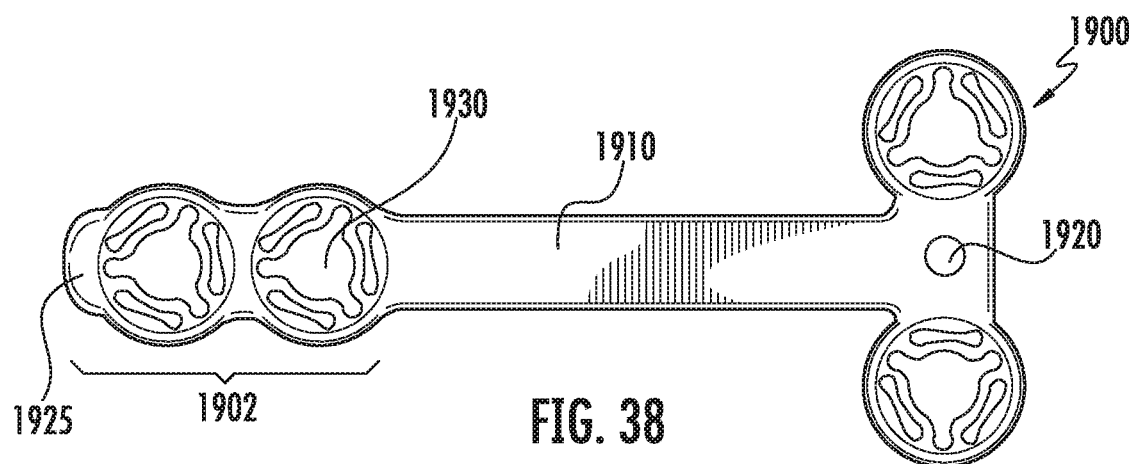
FIG. 38 is a top view an of an implant of a tenth embodiment of the current technology depicting a "T" shaped implant with a means for connection to bone engaging features and various means for engaging an inserter.
Figure 39:
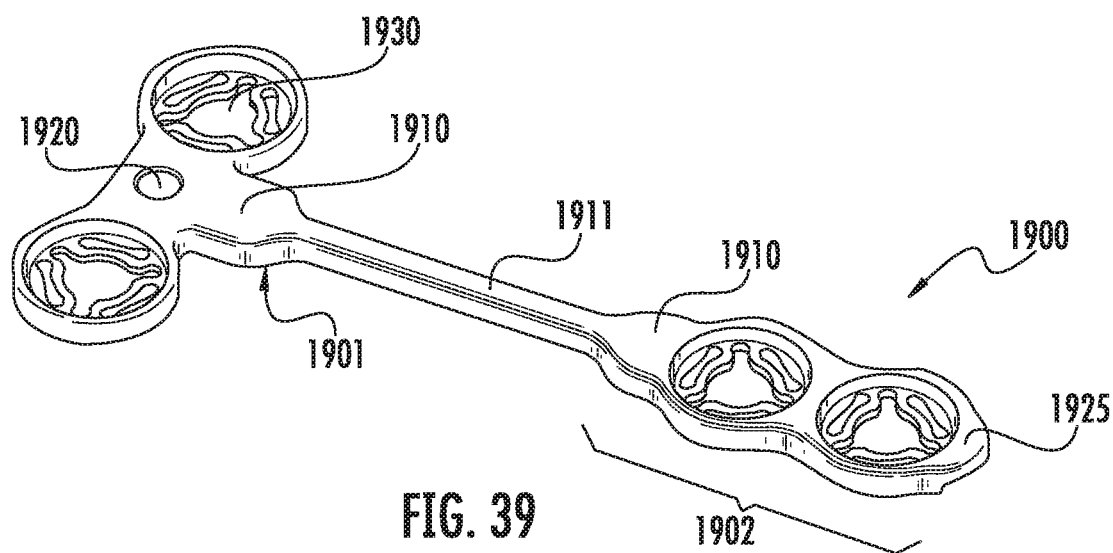
FIG. 39 is a perspective view of the implant of the tenth embodiment of the current technology.

FIG. 38 depicts an embodiment of an implant 1900 of the current technology in a "T" shape. Implants may take on many various configurations. The merits of the current technology are not limited by the shape or style of the implant. In FIG. 38 implant 1900 is shown in a first configuration. The implant 1900 may include multiple connection means for bone engaging members. The bone engaging members may be bone screws, pegs, blades or other means suitable for engaging bone or soft tissue. The connection means 1930 may be of the same or varying styles or geometries for a particular implant. For example, some of the connection means 1930 in implant 1900 may be threaded and or locking while others may be non-threaded or non-locking. Implant 1900 may include a connection for a means for insertion 1925 that is an external feature and may also include a connection for a means for insertion 1920 that is internal. Implant 1900 may include multiple connections 1920 and or 1925 for a means of insertion that may vary in size, geometry, orientation and or configuration. Implant 1900 as depicted in FIG. 38 has a top surface 1910 that may be of uniform shape, size, geometry and or configuration. The perspective view of implant 1900 is shown in FIG. 39. Implant 1900 may include a top surface 1910 and a bottom surface 1901. In FIG. 39 implant 1900 may have a rail or bridge member 1911 that may be of varying size, geometry and or configuration. Bridge member 1911 may or may not be similar in size, shape, geometry and or orientation as top surface 1910 or bottom surface 1901. Implant 1900 may have one or more arms or projections 1902 that may extend from the implant. In FIGS. 38 and 39 implant 1900 is shown in a flat configuration or first configuration. The first configuration may or may not be flat. The first configuration may be flat, angled, arched, bent or some combination thereof. This first configuration may facilitate the surgical implantation. This first configuration may act to store a compressive force or other force.

Figure 40:
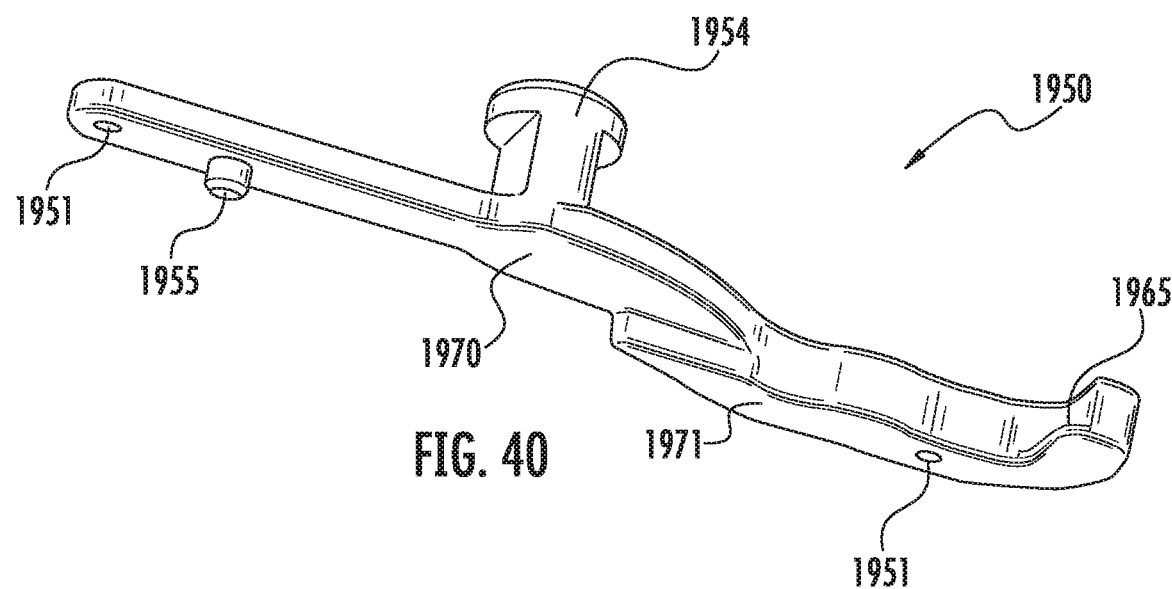
FIG. 40 is a bottom perspective view of an inserter of the tenth embodiment of the current technology depicting an inserter with means for engaging the implant depicted in FIG. 38.
Figure 41:
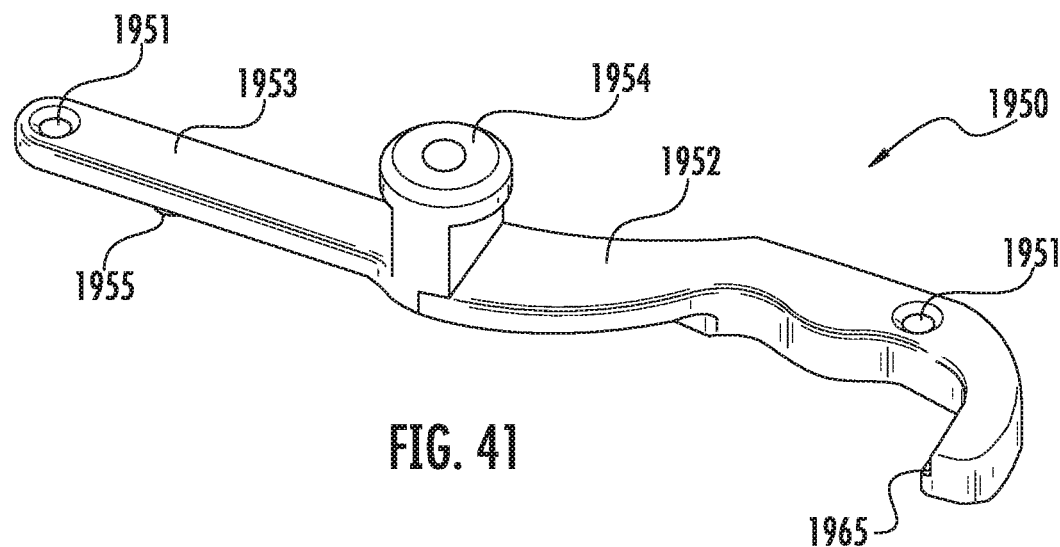
FIG. 41 is a top perspective view of an inserter of the tenth embodiment of the current technology depicting an inserter with means for engaging the implant depicted in FIG. 38.

FIGS. 40 and 41 depict one embodiment of an inserter of the current technology. Inserter 1950 is configured to interact and or engage implant 1900 shown in FIG. 39. The inserter 1950 may hold an implant in a first configuration. Inserter 1950 has a connection means 1954 that may be used for engaging a separate handle or other holding means. This exemplary embodiment may also have feature 1951 in various locations, orientations or configurations. One or more features 1951 may be present in a particular implant. Feature 1951 may be used to provisionally or temporarily attach the inserter and implant combination to a surface such as bone or tissue. A pin or other means may be used to pass through features 1951 for maintaining a relative position of the inserter or inserter-implant combination on the bone or tissue. The current technology may include an inserter and inserter-implant combination that may be used with an implant that has one or more configurations. The inserter 1950 may have an implant connection means 1955 for releasably and or rotatably engaging an implant. Inserter 1950 may include at least a second implant connection means 1965 for releasably engaging an implant. Connection means 1965 and 1955 may or may not be of the same size, shape, geometry, orientation or configuration. FIG. 41 depicts a top side perspective view showing how a temporary fixation means 1951 may extend from the upper surfaces 1952 and 1953 through the bottom surfaces 1971 and 1970. Surfaces 1970 and 1971 may or may not be in the same plane or of the same configuration.

Figure 42:
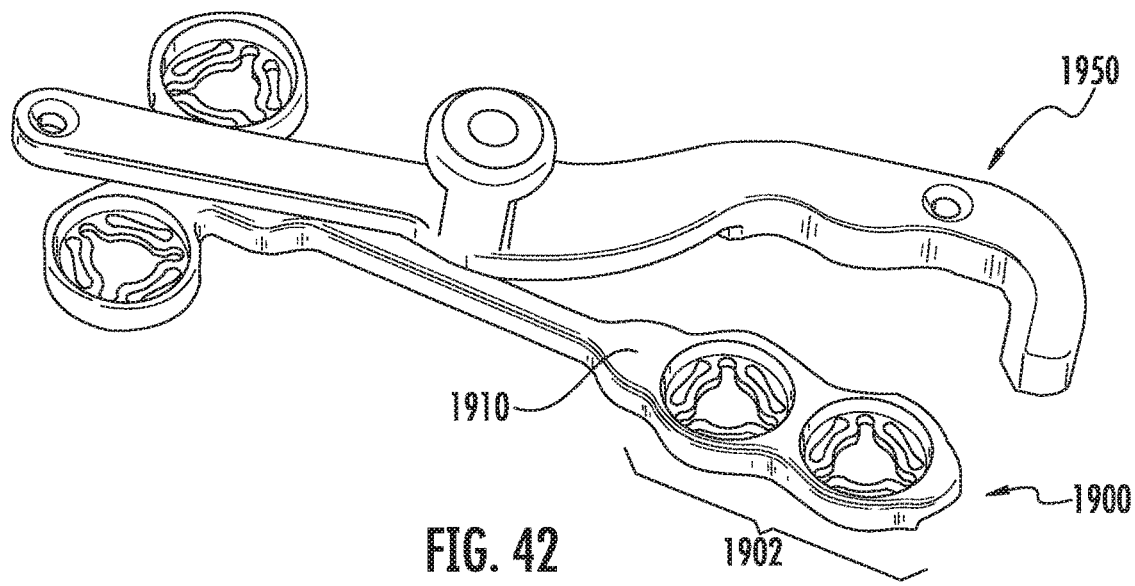
FIG. 42 is a top perspective view of a tenth embodiment of the current technology depicting a partial implant-inserter assembly of the implant depicted in FIG. 38 and the inserter depicted in FIG. 40. The implant is shown in a first configuration.
Figure 43:
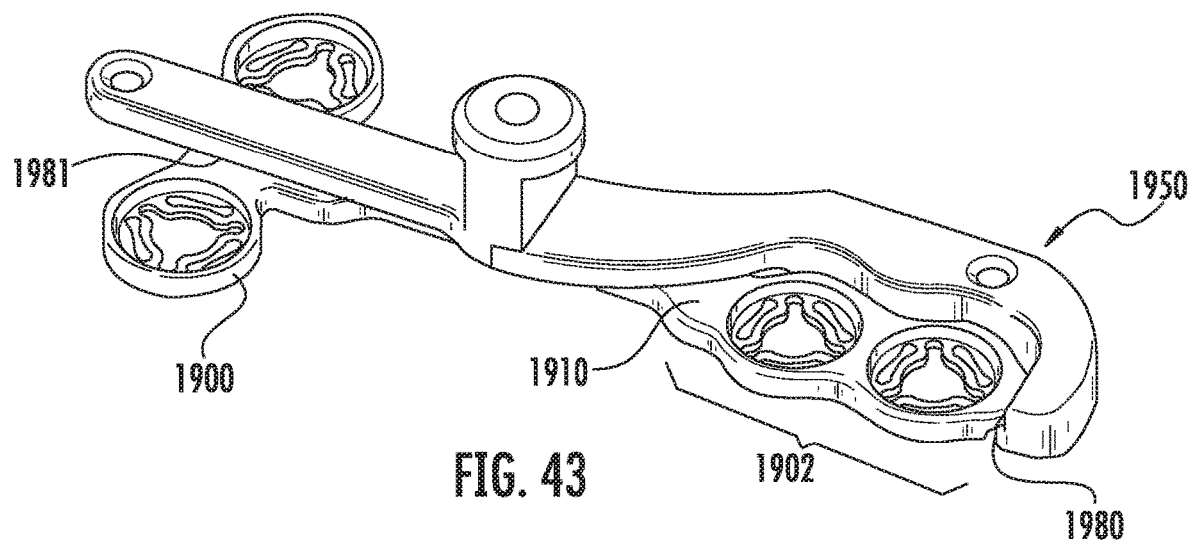
FIG. 43 is a top perspective view of a tenth embodiment of the current technology depicting a completed implant-inserter assembly of the implant depicted in FIG. 38 and the inserter depicted in FIG. 40. The implant is shown in a first configuration.

FIG. 42 depicts inserter 1950 partially engaged with implant 1900. Implant 1900 may be held in a first configuration by the engagement features 1965 and 1955 of inserter 1950. FIG. 43 shows the implant 1900 fully engaged with inserter 1950. Implant 1900 is maintained in a first configuration by the interactions 1980 and 1981 between the implant 1900 and the inserter 1950. The means of insertion may utilize features similar to 1925 as described herein in combination with other surfaces such as top surface 1910. This combination of means of insertion 1925 and surface 1910 may be used to maintain one or more features or arms or projection 1902. A combination of means of insertion such as 1925, 1910 and or 1920 may be used to create a bending modality, such as a three point or four point bend, to maintain a specific implant configuration or combination of configurations. A combination of surfaces and means of insertion, such as 1925, 1910 and or 1920, may be used on the entire implant or portions of an implant to create or maintain a particular configuration of an implant or portions of an implant. For example, a tab such as 1925 and surface, such as 1910, may be used to maintain one arm or projection such as 1902 of an implant in a particular configuration. When disassembled, that arm may have a configuration that is different from or the same as the configuration of the rest of the implant.

Figure 44:
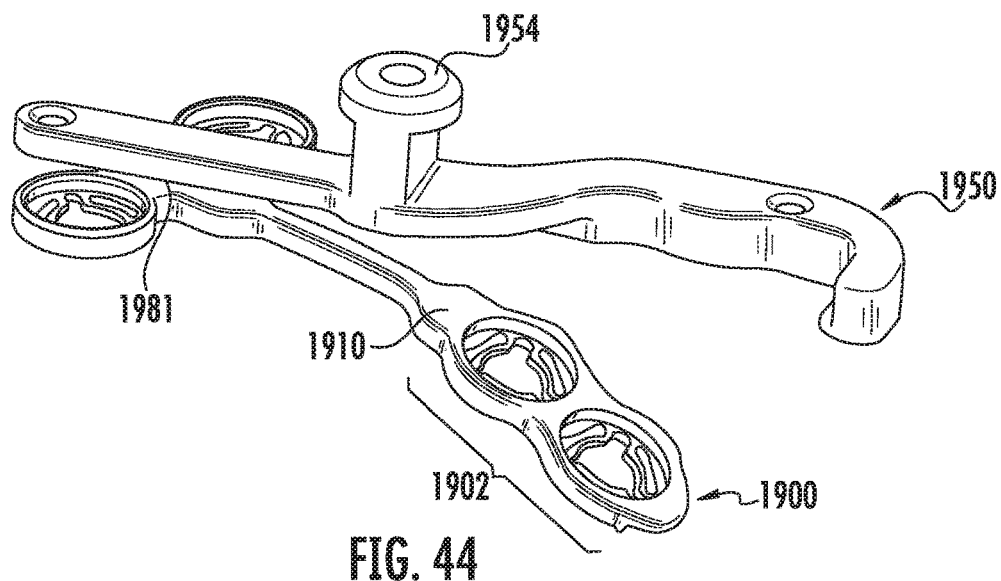
FIG. 44 is a top perspective view of the tenth embodiment depicting the implant-inserter combination depicted in FIG. 43 depicting a partial disassembly of the implant-inserter combination. The implant is shown in a second configuration.

FIG. 44 depicts the inserter 1950 partially disassembled from implant 1900. As the implant 1900 disengages from the inserter 1950 it may achieve a second configuration. This second configuration may be achieved by the design of the implant 1900 and or in combination with the intrinsic material properties of the implant and or in combination with the processing of the implant 1900. This second configuration may act to create a compressive force or other force across one or two bone or tissue segments.

Figure 45:
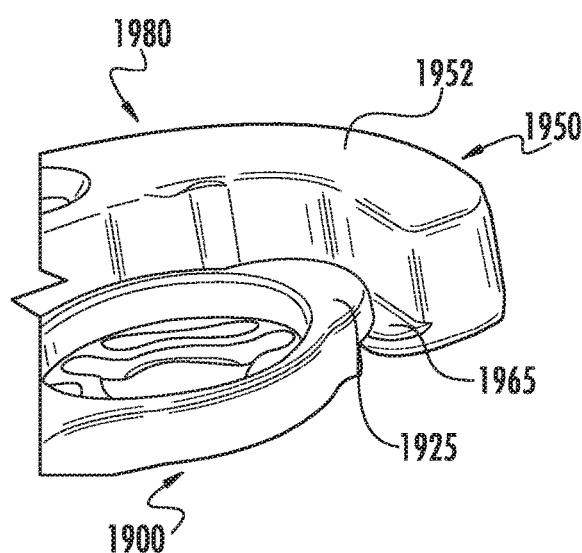
FIG. 45 is a perspective view of one of the implant-inserter connection means of the assembly shown in FIG. 43.
Figure 46:
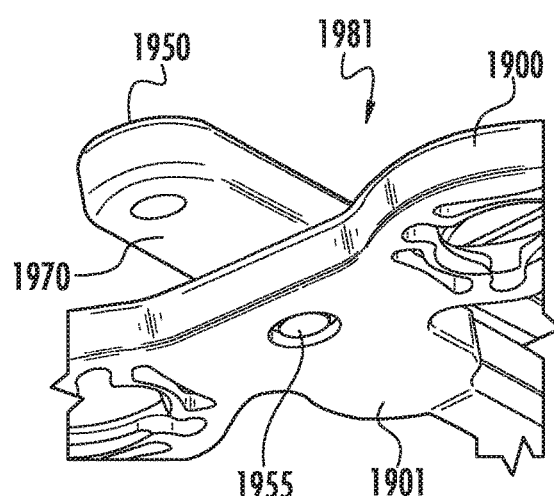
FIG. 46 is a perspective view of one of the implant-inserter connection means of the assembly shown in FIG. 43.

FIG. 45 depicts the interaction 1980 between the implant 1900 and the inserter 1950. The surface 1965 may releasably engage or interact with the connection means 1925 of implant 1900. Interaction or interface 1980 may work in combination with the interaction or interface 1981 to maintain an implant in a first configuration. Feature 1955 of inserter 1950 may releasably engage feature 1920 of implant 1900. This interaction or interface may allow rotation, pivoting, latching or other motion to facilitate the assembly or interaction between the implant and inserter.

Figure 47:
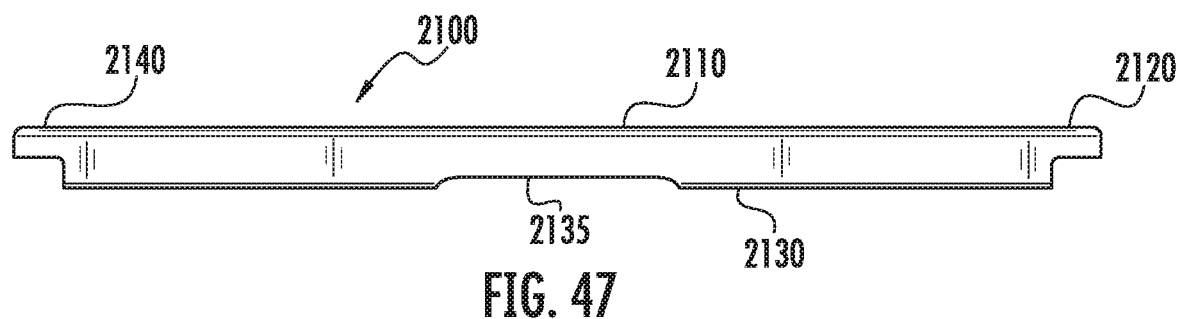
FIG. 47 is a side view of an eleventh embodiment of the current technology depicting an implant with a means for engaging an inserter.
Figure 48:
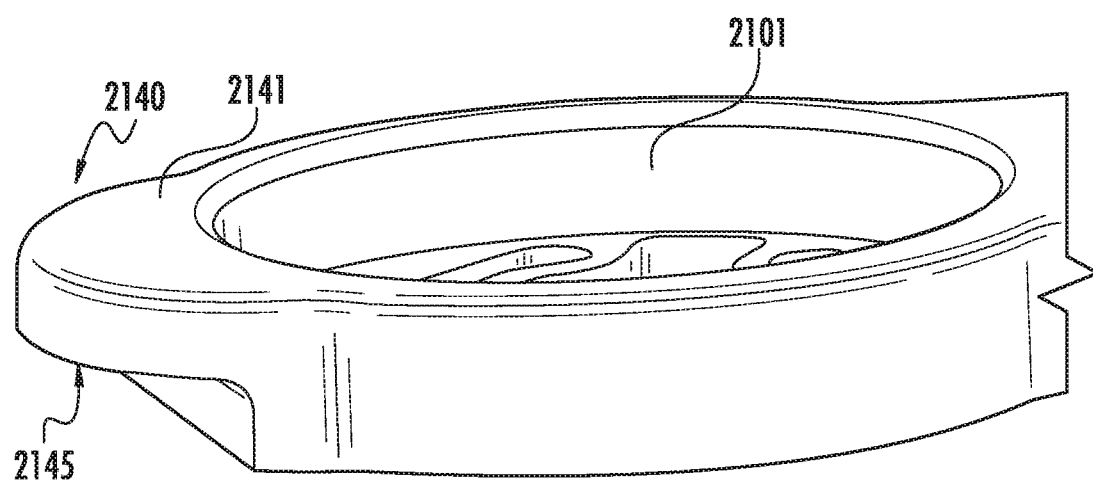
FIG. 48 is a perspective view of the embodiment depicted in FIG. 47 illustrating the means for engaging an inserter.
Figure 49:
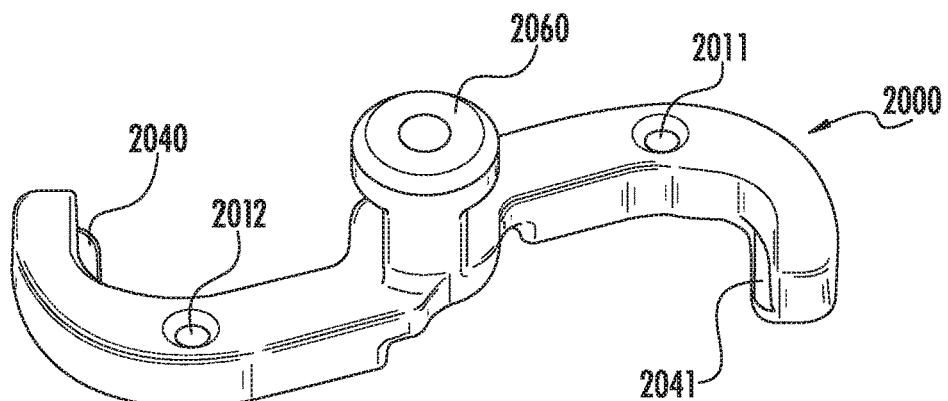
FIG. 49 is a top perspective view of an eleventh embodiment of the current technology depicting an inserter with means for engaging an implant of the current technology.
Figure 50:
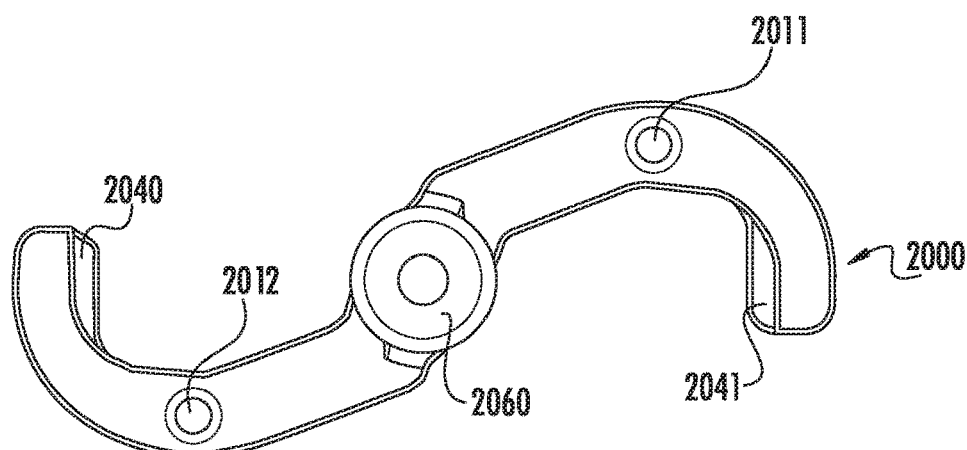
FIG. 50 is a top view of the inserter depicted in FIG. 49.
Figure 51:
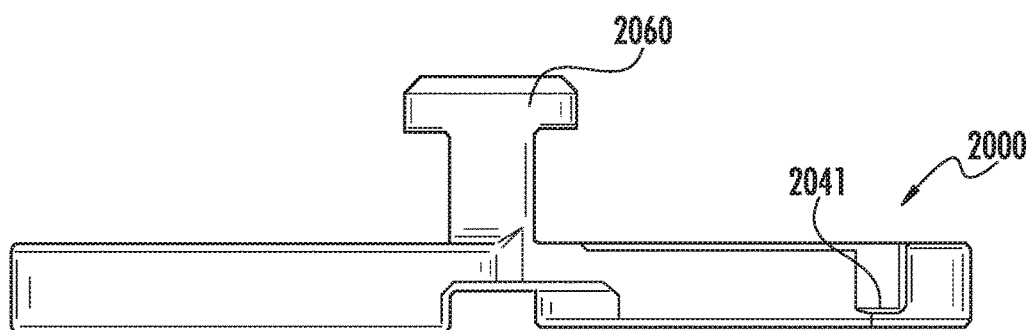
FIG. 51 is a front view of the inserter depicted in FIG. 49.
Figure 52:
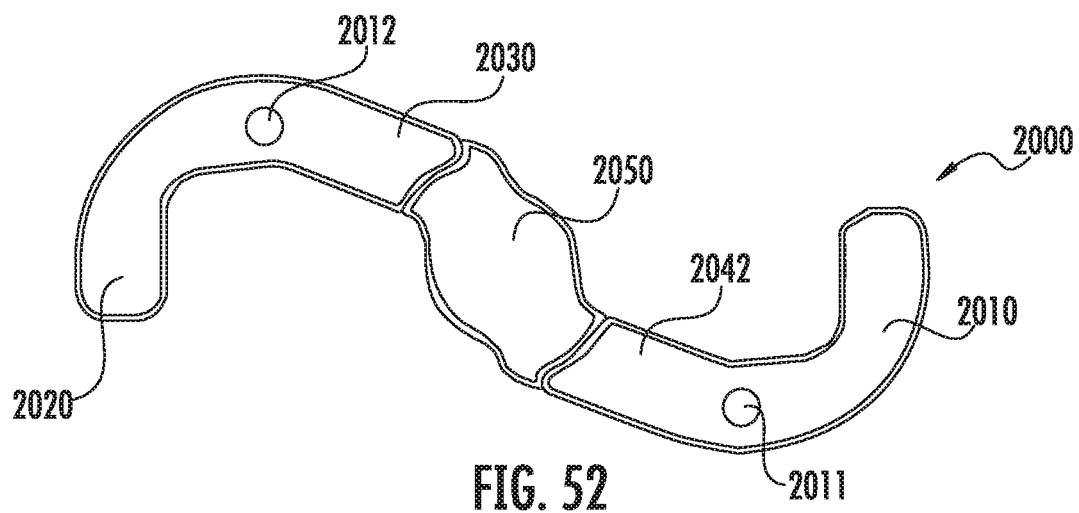
FIG. 52 is a bottom view of the inserter depicted in FIG. 49.

The embodiment of the current technology depicted in FIG. 47 is an implant 2100 having a top surface 2110 and one or more connection means 2101 for bone engaging members. The bone engaging members may be bone screws, pegs, blades or other means suitable for engaging bone or soft tissue. The connection means 2101 may be of the same or varying styles or geometries for a particular implant. For example, some of the connection means 2101 in implant 2100 may be threaded and or locking while others may be non-threaded or non-locking. Implant 2100 may have one or more means 2140 and 2120 for connecting to an inserter or other means of insertion. One embodiment of means 2140 may include a top surface 2141 and a bottom surface 2145 as depicted in FIG. 48. Means 2140 may or may not be in close proximity to connection means 2101. The embodiment of implant 2100 in FIG. 47 is shown is a first configuration.

The advantages of the current technology and embodiment shown in FIGS. 42-46 are numerous and may include the ability of the means of insertion to maintain an implant in a first configuration. These embodiments may also allow the implant-inserter combination to be provisionally fixed or temporarily fixed to bone segment or tissue segments while maintaining the implant in a first configuration during the method of implantation. The inserter may be releasably engaged to the implant to facilitate assembly and disassembly of the implant and inserter. The assembly and disassembly is in a direction or movement that is conducive to the surgical procedure. Once the implant and inserter are fully disassembled the implant may achieve a second configuration. This second configuration may be achieved by the design of the implant and or in combination with the intrinsic material properties of the implant and or in combination with the processing of the implant 1600. This second configuration may act to create a compressive force or other force across one or two bone or tissue segments. The implant may or may not be pre-assembled to the inserter in the final packaging.

FIGS. 49, 50, 51 and 52 depict an inserter 2000 of the current technology. Inserter 2000 may or may not have a connection means 2060 for attaching to a handle or other holding means. The inserter 2000 may have one or more features 2011 and 2012 for temporarily attaching the inserter to one or more bone or tissue segments. The inserter may have means 2040 and 2041 for releasably engaging an implant to maintain an implant in a first configuration or a configuration that is different than the implant configuration of the implant. Inserter 2000 may have one or more projections or arms 2020 and 2010 for facilitating connection to an implant. Inserter 2000 may have bottom surfaces 2030, 2042 and 2050 for engaging and or facilitating connection to an implant.

Figure 53:
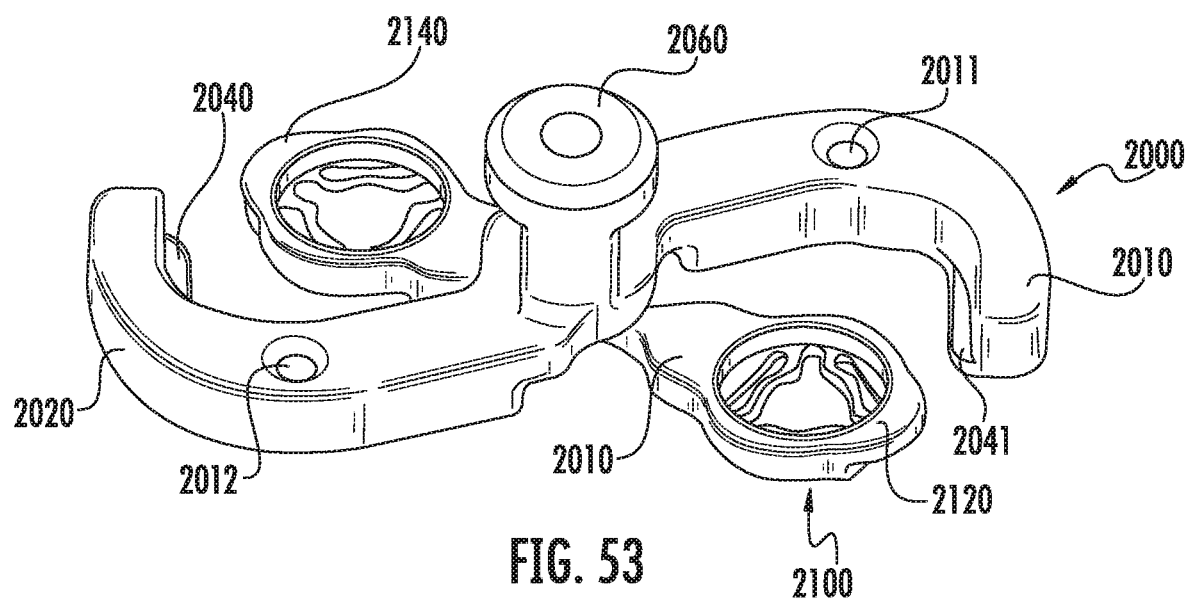
FIG. 53 is a top perspective view of the eleventh embodiment of the current technology depicting a partial implant-inserter assembly of an implant and the inserter depicted in FIG. 49. The implant is shown in a first configuration.
Figure 54:
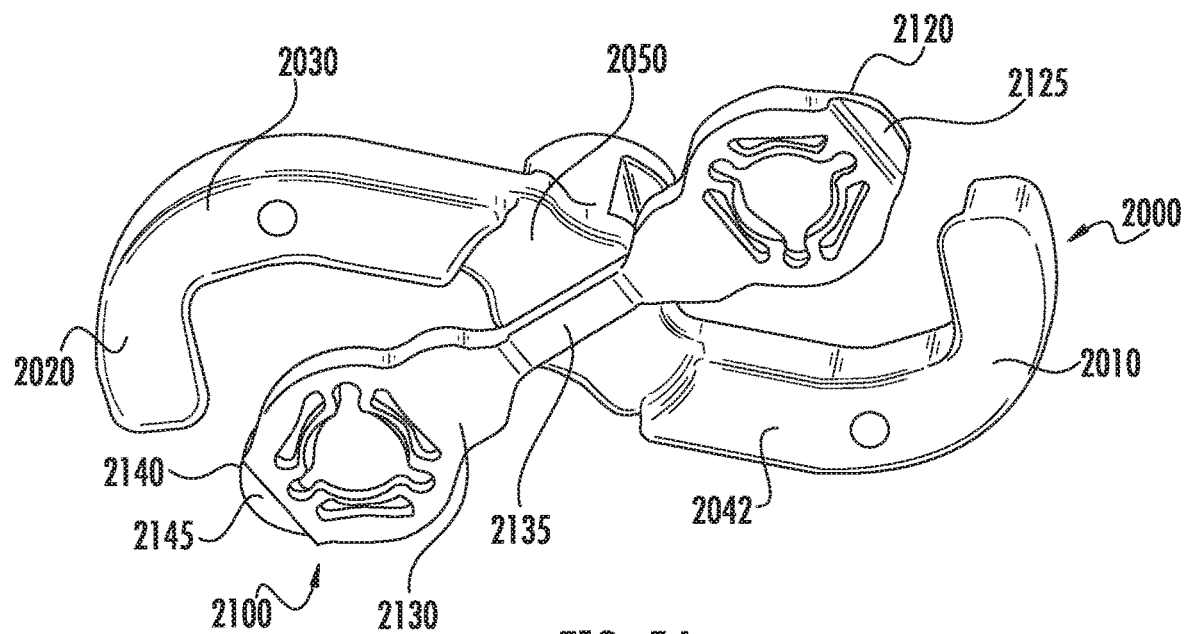
FIG. 54 is a bottom perspective view of the implant-inserter combination depicted in FIG. 53.

FIGS. 53 and 54 depict inserter 2000 partially assembled to an implant 2100. The implant may be held or maintained in a first configuration. Top surface 2110 of implant 2100 may slidably interface with bottom surfaces 2030 and 2042 of inserter 2000. These surfaces may be coplanar and may or may not physically engage one another. Surface 2040 of inserter 2000 may releasably engage bottom surface 2145 of means 2140 on implant 2100. Surface 2041 of inserter 2000 may releasably engage bottom surface 2125 of means 2120 on implant 2100. The engagement of surface 2041 with surface 2125 may occur simultaneously with engagement of surface 2040 and surface 2145. This interaction may maintain implant 2100 in a first configuration. The engagement of surface 2041 with surface 2125 and the engagement of surface 2040 with surface 2145 may occur from opposite directions which may require inserter 2000 to pivot relative to implant 2100. This engagement may occur from the same direction as a sliding motion or top load motion. The merits of the current technology are maintained regardless of the direction of assembly.

Figure 55:
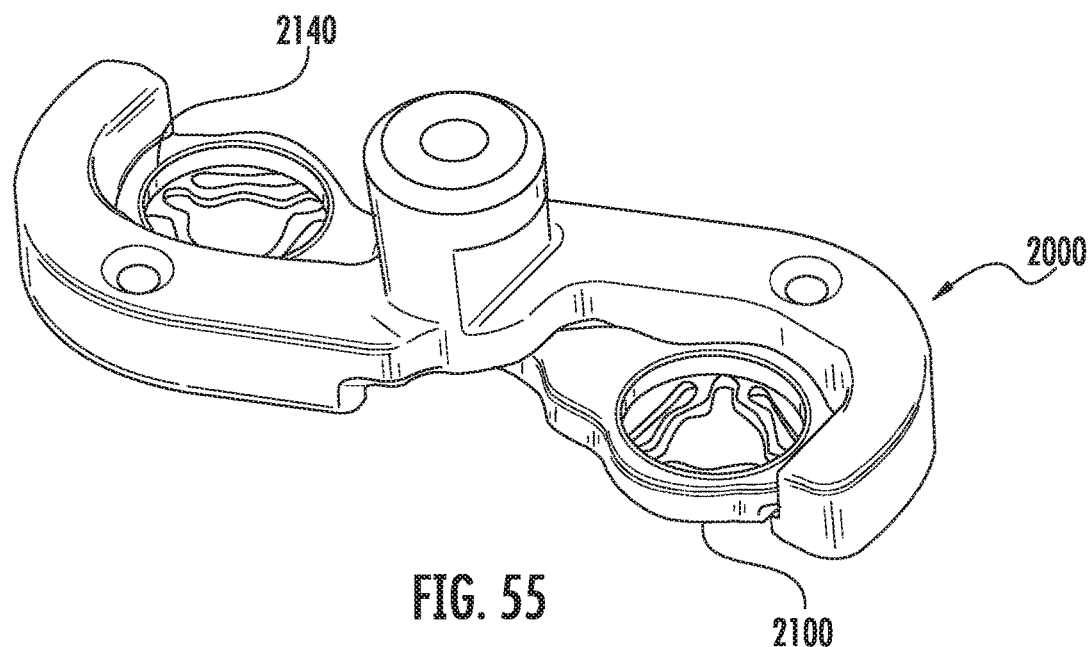
FIG. 55 is a top perspective view of an additional embodiment of the current technology depicting a completed implant-inserter assembly of an implant and the inserter depicted in FIG. 49. The implant is shown in a first configuration.
Figure 56:
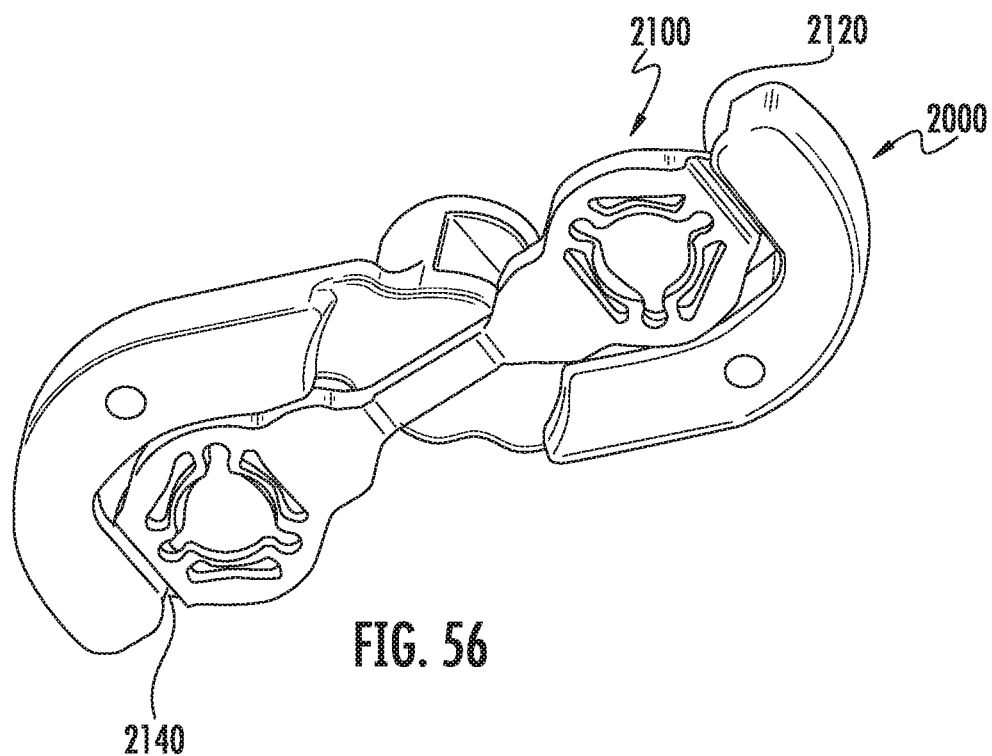
FIG. 56 is a bottom a perspective view the implant-inserter combination depicted in FIG. 55.

FIGS. 55 and 56 depict inserter 2000 fully or completely assembled to an implant 2100. The implant may be held or maintained in this first configuration. FIG. 55 depicts the implant 2100 held in a first configuration which may or may not be flat. The first configuration may be flat, angled, arched, bent or some combination thereof. This first configuration may facilitate the surgical implantation. This first configuration may act to store a compressive force or other force. Top surface 2110 of implant 2100 may slidably interface with bottom surfaces 2030 and 2042 of inserter 2000. These surfaces may be coplanar and may or may not physically engage one another. Surface 2040 of inserter 2000 may releasably engage bottom surface 2145 of means 2140 on implant 2100. Surface 2041 of inserter 2000 may releasably engage bottom surface 2125 of means 2120 on implant 2100. The engagement of surface 2041 with surface 2125 may occur simultaneously with engagement of surface 2040 and surface 2145. This interaction may maintain implant 2100 in a first configuration. The engagement of surface 2041 with surface 2125 and the engagement of surface 2040 with surface 2145 may occur from opposite directions which may require inserter 2000 to pivot relative to implant 2100. This engagement may occur from the same direction as a sliding motion or top load motion. The merits of the current technology are maintained regardless of the direction of assembly.

Figure 57:
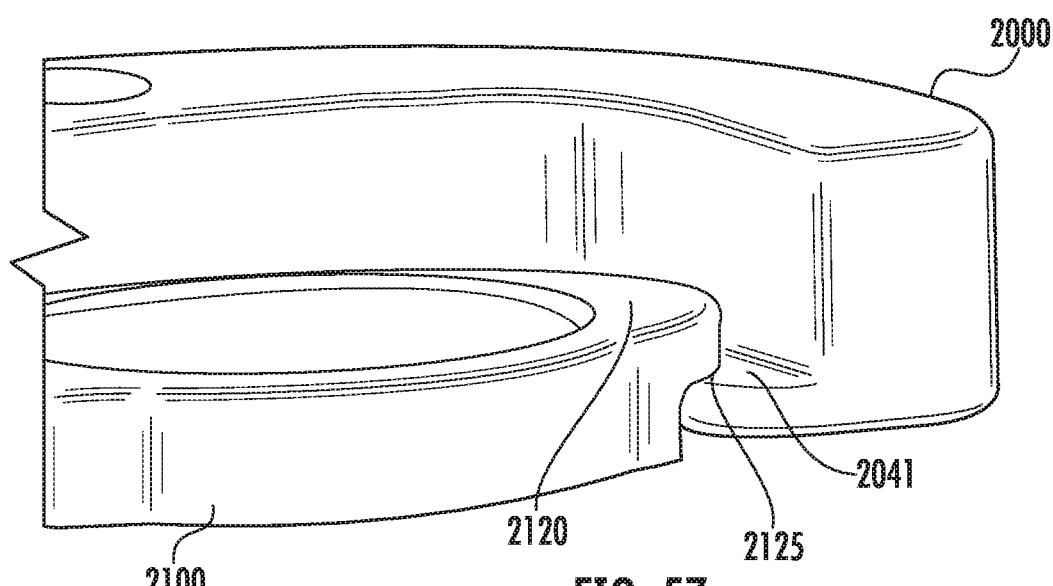
FIG. 57 is a perspective view of the eleventh embodiment depicting the implant-inserter connection means of the assembly shown in FIG. 55. The implant is shown in a first configuration.

FIG. 57 depicts the interaction of the holding means between inserter 2000 and implant 2100. Surface 2041 slidably engages with bottom surface 2125 of implant 2100. This may provide the necessary support to maintain an implant in a first configuration or a configuration may be different than the implanted configuration. In this embodiment, the general shape of the engagement is depicted as an "L" shape interface. As previously described herein, alternate geometries and or configurations may be used. However to those skilled in the art it is apparent that numerous geometries and configuration or combination of geometries and configurations are possible and may be encompassed by the current technology. Other possible alternative embodiment of geometries for connection to a means of insertion have been described herein. The means of insertion may or may not be flush with the implant. The connection between an implant and inserter and the means of insertion my hold the implant in a first configuration and or an alternate configuration. As the inserter and implant are disassembled, the disassembly may allow the implant to achieve a second or alternative configuration. This disassembly may allow the implant to achieve multiple alternative configurations. For example, step 1 of the disassembly may allow the implant to achieve a second configuration and step 2 may allow the implant to achieve a third configuration and step 3 of the disassembly may allow the implant to achieve a fourth configuration. This disassembly may allow the implant or portions of the implant to achieve multiple alternative configurations. For example, step 1 of the disassembly may allow the portion A of the implant to achieve a second configuration and step 2 may allow portion B of the implant to achieve an alternate configuration and step 3 of the disassembly may allow portion C of the implant to achieve an alternate configuration. Those skilled in the art will understand that combinations of alternate configurations of an implant or portions of an implant may be possible with the current technology. Certain alternate configurations may be intermediate configurations that will revert to a previous configuration or may proceed to a final configuration once fully disassembled from the inserter. The embodiments described herein do not limit the scope of the current technology.

Figure 58:
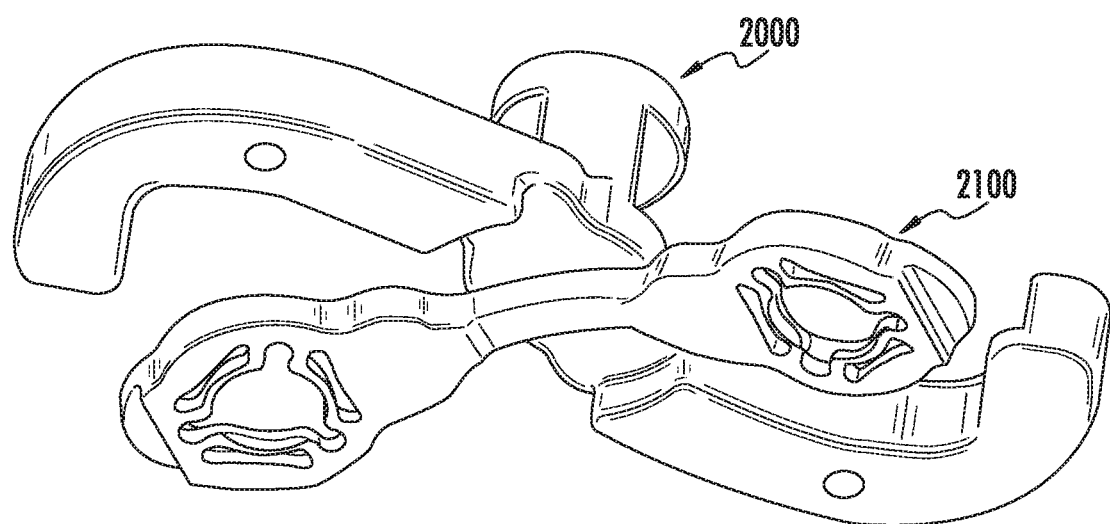
FIG. 58 is a top perspective view of the eleventh embodiment depicting the implant-inserter combination depicted in FIG. 55 depicting a partial disassembly of the implant-inserter assembly of an implant and the inserter depicted in FIG. 49. The implant is shown in a second configuration.
Figure 59:
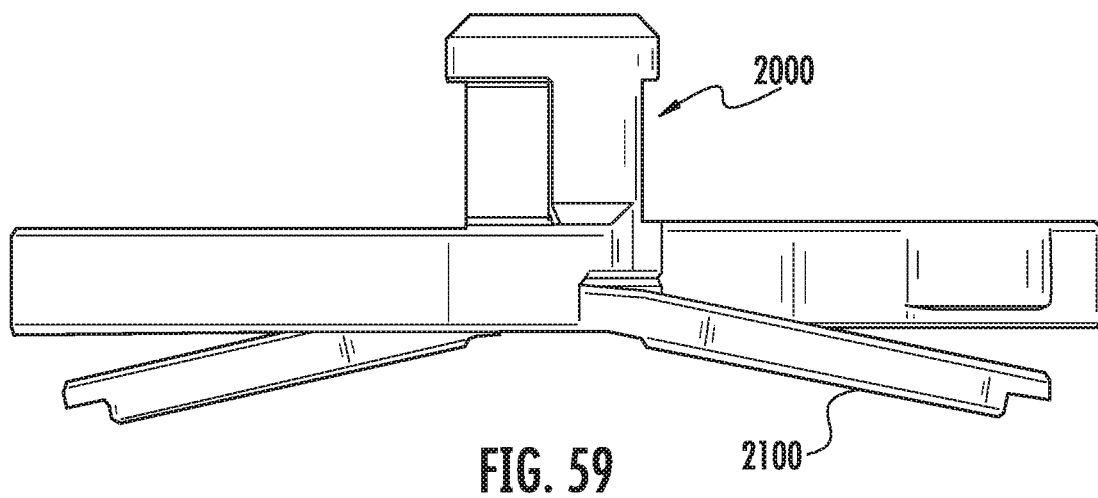
FIG. 59 is a front view of partial disassembly of the implant-inserter assembly represented in FIG. 58. The implant is shown in a second configuration.

FIGS. 58 and 59 depict the implant 2100 disengaged or released from the inserter 2000. The implant 2100 is allowed to achieve a second configuration or a configuration different than the one maintained by the inserter. This second configuration may be achieved by the design of the implant 2100 and or in combination with the intrinsic material properties of the implant and or in combination with the processing of the implant. This second configuration may act to create a compressive force or other force across one or two bone or tissue segments. The connection between an implant and inserter and the means of insertion my hold the implant in a first configuration and or an alternate configuration. As the inserter and implant are disassembled, the disassembly may allow the implant to achieve a second or alternative configuration. This disassembly may allow the implant to achieve multiple alternative configurations. For example, step 1 of the disassembly may allow the implant to achieve a second configuration and step 2 may allow the implant to achieve a third configuration and step 3 of the disassembly may allow the implant to achieve a fourth configuration. This disassembly may allow the implant or portions of the implant to achieve multiple alternative configurations. For example, step 1 of the disassembly may allow the portion A of the implant to achieve a second configuration and step 2 may allow portion B of the implant to achieve an alternate configuration and step 3 of the disassembly may allow portion C of the implant to achieve an alternate configuration. Those skilled in the art will understand that combinations of alternate configurations of an implant or portions of an implant may be possible with the current technology. Certain alternate configurations may be intermediate configurations that will revert to a previous configuration or may proceed to a final configuration once fully disassembled from the inserter. The embodiments described herein do not limit the scope of the current technology. Further embodiments and combinations of embodiment may be possible and will become evident to those skilled in the art. The current technology may include an inserter and inserter-implant combination that may be used with an implant that has one or more configurations.

Based on the description herein, those skilled in the art will know that various mechanisms may be created as a means of insertion that may maintain an implant in one configuration that may vary from a second or implant configuration. The merits of the current technology are particularly beneficial in application where an implant may have means for connecting with bone engaging members such as bone screws or pegs. Controlling the ability of an implant to have multiple configurations is beneficial to ensure proper implant sizing, orientation, placement, and or fixation to one or more bone or tissue segments.

Figure 60:
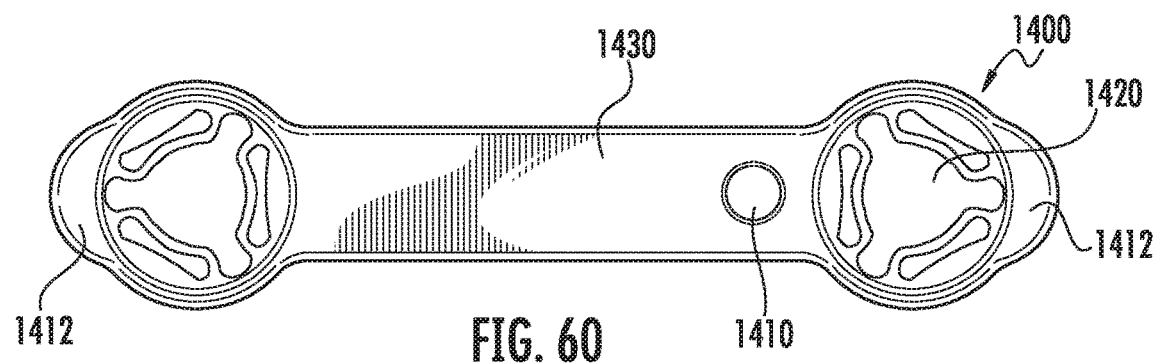
FIG. 60 is a top view of a twelfth embodiment of the current technology depicting an implant with a means for connection to bone engaging features and various means for engaging an inserter.
Figure 61:
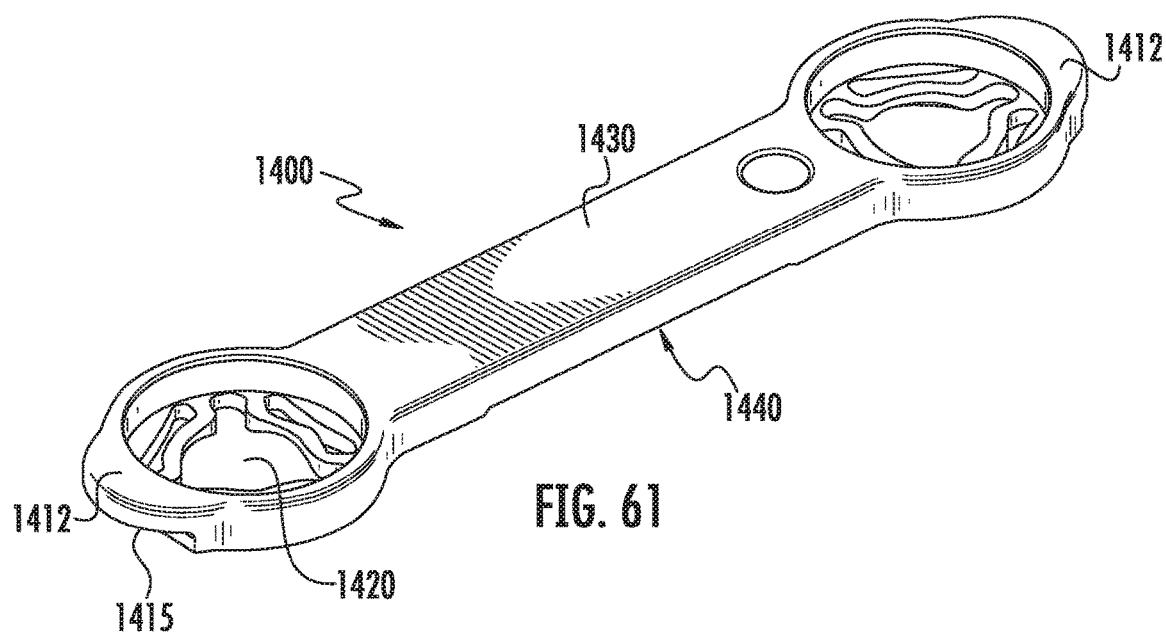
FIG. 61 is a perspective view of the embodiment shown in FIG. 60.
Figure 62:
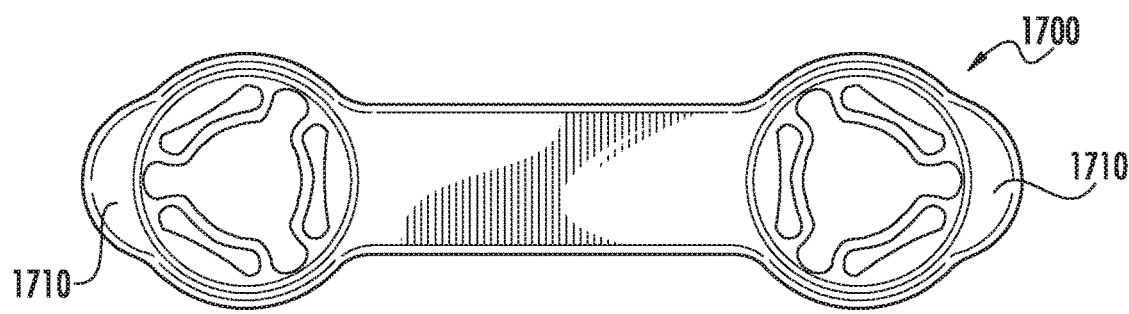
FIG. 62 is a top view of a thirteenth embodiment of the current technology depicting an implant with a means for connection to bone engaging features and a means for engaging an inserter.
Figure 63:
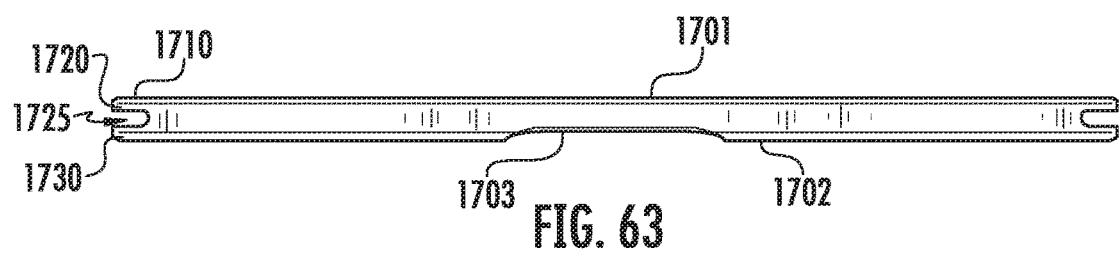
FIG. 63 is a front view of the embodiment shown in FIG. 62.
Figure 64:
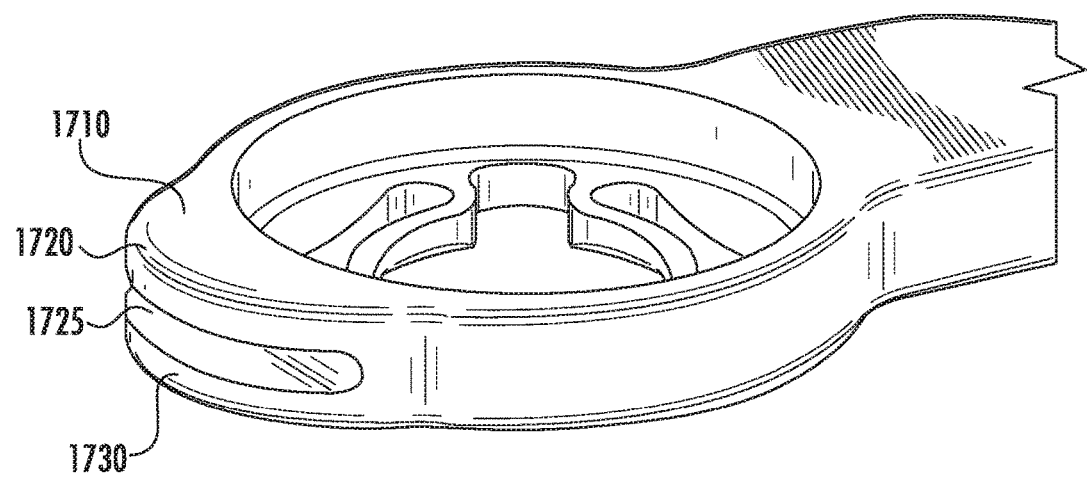
FIG. 64 is a perspective view of the embodiment depicted in FIG. 62 illustrating the means for connection to bone engaging features and the means for engaging an inserter.

FIGS. 60 and 61 depict yet another embodiment of an implant 1400 with multiple means of connecting to an inserter. This embodiment of the implant 1400 may combine an internal means of connection 1410 with one or more external means of connection 1412. The means of connecting to an inserter may or may not be in close proximity to the means of connecting to bone engaging features 1420. Various means of connecting to an inserter may be used in combination with various implant configurations. FIGS. 62, 63 and 64 depict a means of connection 1710 to an inserter that may include a tab consisting of a top element 1720 and a bottom element 1730 that may create a space 1725. The implant 1700 has a top surface 1701 and a bottom surface 1702 that may include at least one or more thinner sections 1703. The combination of surfaces 1701, 1702 and 1703 may constitute a bridge or rail member that may be designed to achieve a second configuration or predict or determine the geometry of the second configuration. The means of insertion may utilize features similar to 1710 as described herein in combination with other surfaces such as top surface 1701. This combination of means of insertion may be used to maintain one or more features or arms or projections. This combination of means of insertion may create a bending modality, such as a three point or four point bend, to maintain a specific implant configuration or combination of configurations. A combination of surfaces and means of insertion, such as 1710, may be used on the entire implant or portions of an implant to create or maintain a particular configuration of an implant or portions of an implant. For example, a tab such as 1710 and top surface, such as 1701 may be used to maintain one side, one arm, one projection and or one portion of an implant in a particular configuration. When disassembled, that arm may have a configuration that is different from or the same as the configuration of the rest of the implant.

Figure 65:
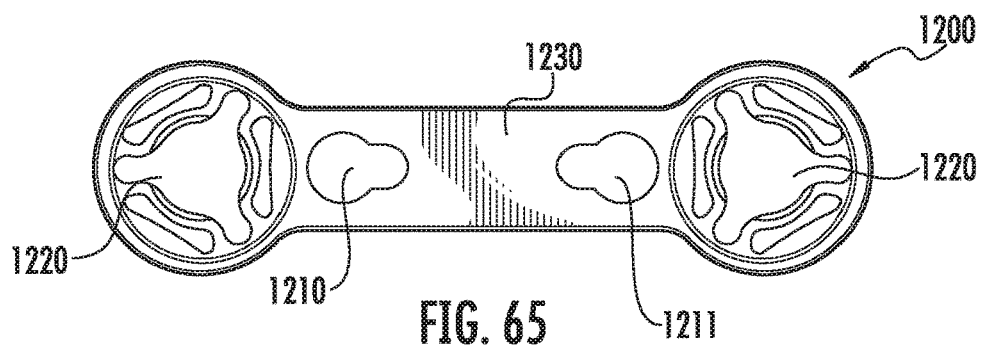
FIG. 65 is a top view of a fourteenth embodiment of the current technology depicting an implant with a means for connection to bone engaging features and a means for engaging an inserter.
Figure 66:
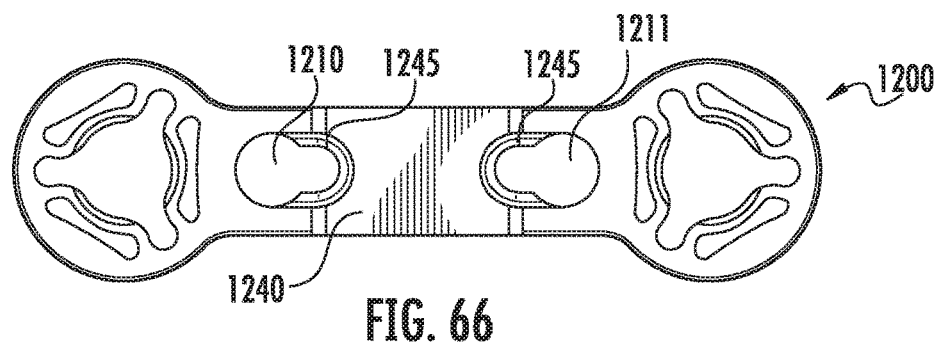
FIG. 66 is a bottom view of the embodiment shown in FIG. 65.
Figure 67:
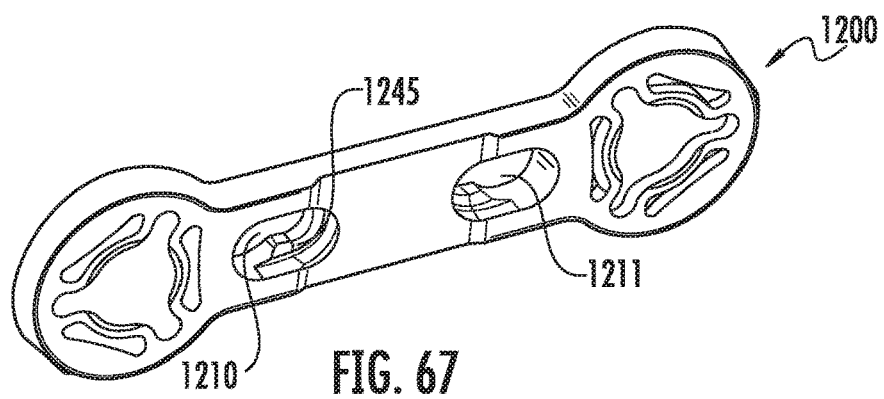
FIG. 67 is a perspective view of the embodiment shown in FIG. 65.
Figure 68:
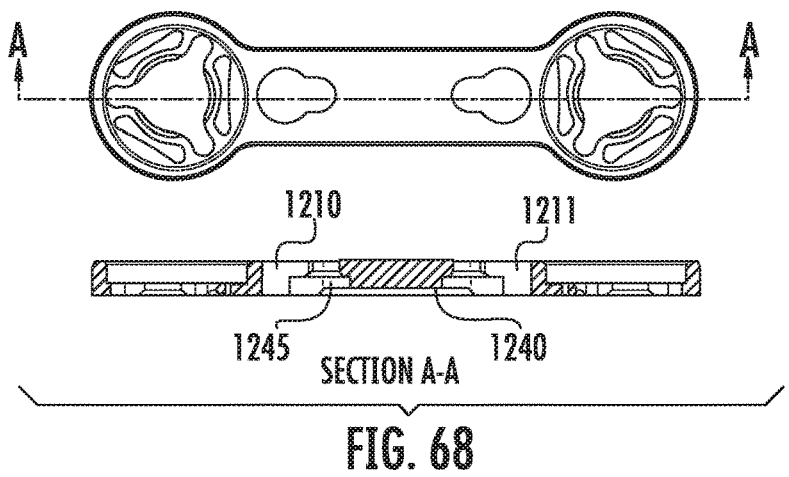
FIG. 68 is a section view of the embodiment shown in FIG. 65.

FIG. 65 depicts the implant 1200 in a first configuration. Implant 1200 has one or more connection means 1220 for fastening bone engaging members to the implant. Connection means 1220 may be a multitude of geometries for connecting bone engaging members to the implant. For example these connection means 1220 may be one of the following or a combination of the following: threads, locking geometries, or mating geometries conducive to interfacing with a bone engaging member. Those skilled in the art will understand the various options available for connecting an implant to a bone engaging member, such as a bone screw or peg. Implant 1200 has a means 1210 and 1211 for attaching to an inserter. FIG. 65 shows inserter attaching means 1210 and 1211 as mirror images. These means could be any number of geometries or orientations. Exemplary embodiments are described herein. The implant 1200 may have one or more inserter connection means. These connection means may be similar in geometry or vastly different in geometry. In this embodiment, the inserter connection means 1210 and 1211 have an upper surface 1230 and pass from the upper surface 1230 to a lower surface 1240. As shown in FIGS. 65, 66, and 67 the insert connection means may have different geometries at the upper surface 1230 and the lower surface 1240. In this embodiment the inserter connection means 1210 and 1211 have geometry that provides a lower surface 1245. The passage ways for 1210 and 1211 may work with the lower surface 1245 to engage a mating geometry of an inserter for holding the implant in a first configuration that may be flat or may have some non linear geometry. The features of this embodiment are further depicted in FIG. 68 by the section view. The lower surface 1245 of the inserter connection means 1210 and 1211 may not be at the same level or orientation as the lower surface 1240 of the implant 1200.

Figure 69:
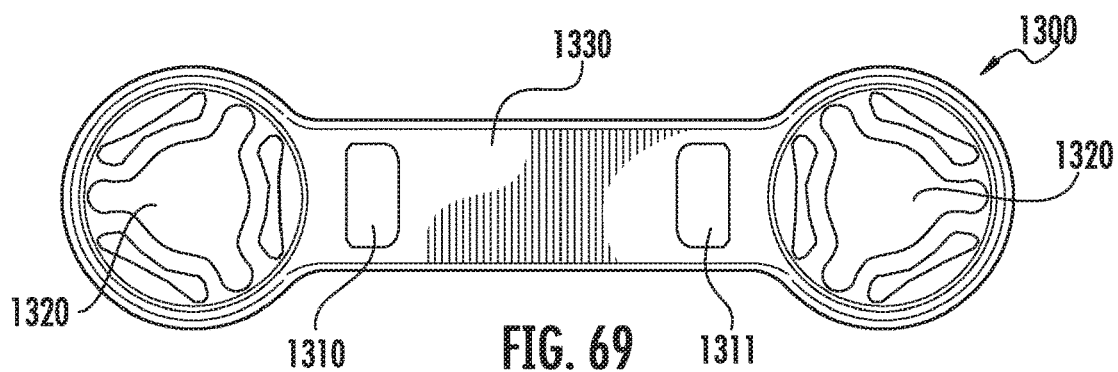
FIG. 69 is a top view of a fifteenth embodiment of the current technology depicting an implant with a means for connection to bone engaging features and a means for engaging an inserter.
Figure 70:
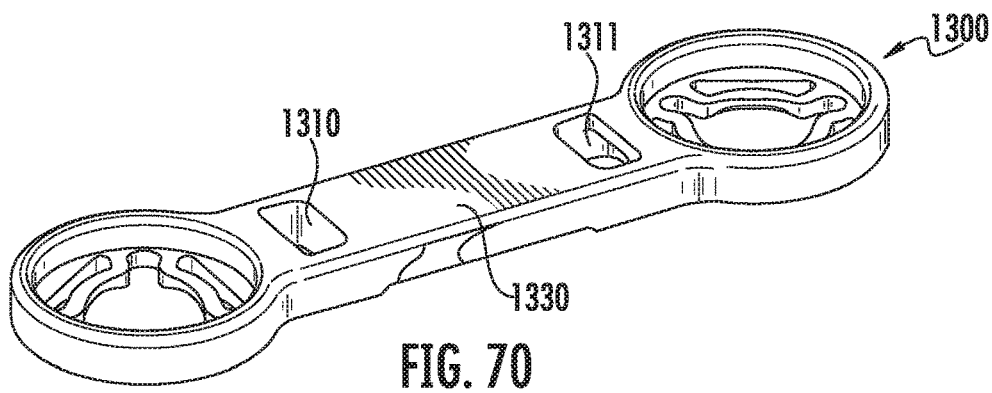
FIG. 70 is a perspective view of the embodiment shown in FIG. 69.
Figure 71:
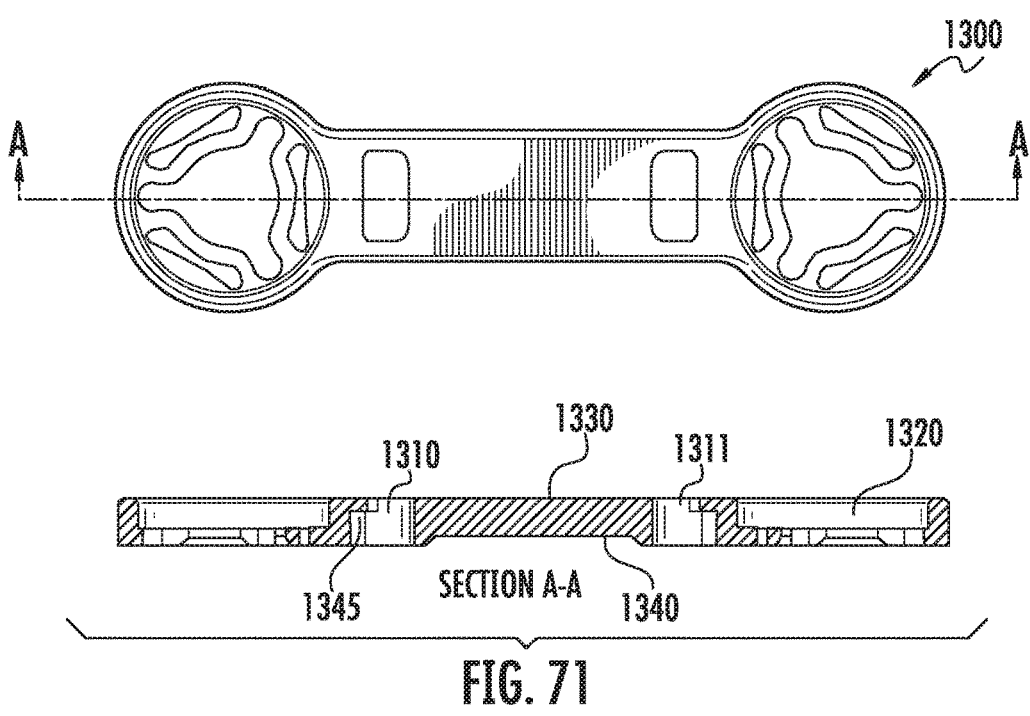
FIG. 71 is a section view of the embodiment shown in FIG. 69.
Figure 72:
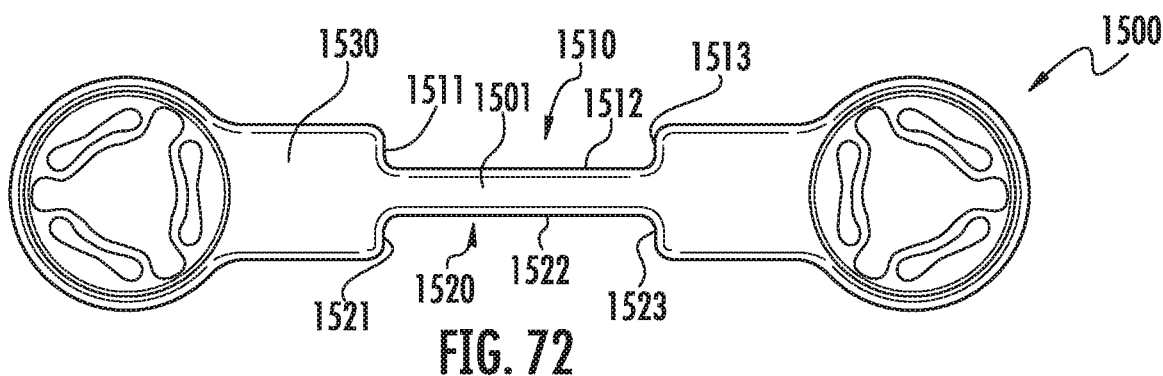
FIG. 72 is a top view of a sixteenth embodiment of the current technology depicting an implant with a means for connection to bone engaging features and a means for engaging an inserter.
Figure 73:
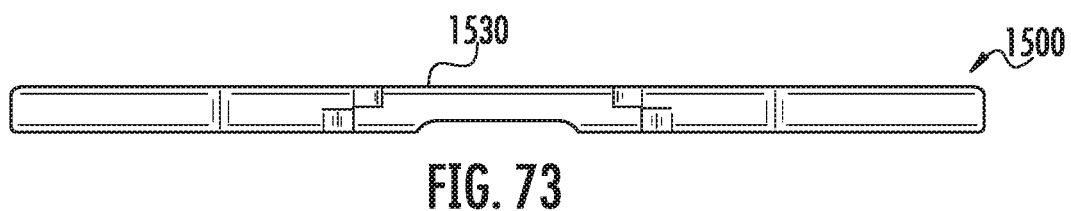
FIG. 73 is a front view of the embodiment shown in FIG. 72.

FIG. 69 depicts the implant 1300 in a first configuration. Implant 1300 has one or more connection means 1320 for fastening bone engaging members to the implant. Connection means 1320 may be a multitude of geometries for connecting bone engaging members to the implant. For example these connection means 1320 may be one of the following or a combination of the following: threads, locking geometries, or mating geometries conducive to interfacing with a bone engaging member. Those skilled in the art will understand the various options available for connecting an implant to a bone engaging member, such as a bone screw or peg. Implant 1300 has a means 1310 and 1311 for attaching to an inserter. FIG. 70 shows inserter attaching means 1310 and 1311 as mirror images. These means may be any number of geometries or orientations. Exemplary embodiments are described herein. The implant 1300 may have one or more inserter connection means. These connection means may be similar in geometry or vastly different in geometry. In this embodiment, the inserter connection means 1310 and 1311 have an upper surface 1330 and pass from the upper surface 1330 to a lower surface 1340. As shown in FIGS. 69, 70 and 71 the inserter connection means may have different geometries at the upper surface 1330 and the lower surface 1340. In this embodiment the inserter connection means 1310 and 1311 have geometry that provides a lower surface 1345. The passage ways for 1310 and 1311 may work with the lower surface 1345 to engage a mating geometry of an inserter for holding the implant in a first configuration that may be flat or may have some non linear geometry. The features of this embodiment are further depicted in FIG. 71 by the section view. The lower surface 1345 of the inserter connection means 1310 and 1311 may not be at the same level or orientation as the lower surface 1340 of the implant 1300.

Figure 74:
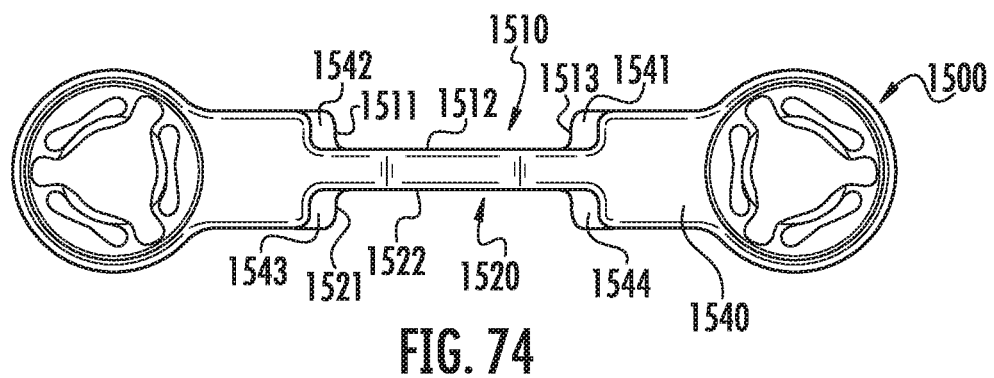
FIG. 74 is a bottom view of the embodiment shown in FIG. 72.
Figure 75:
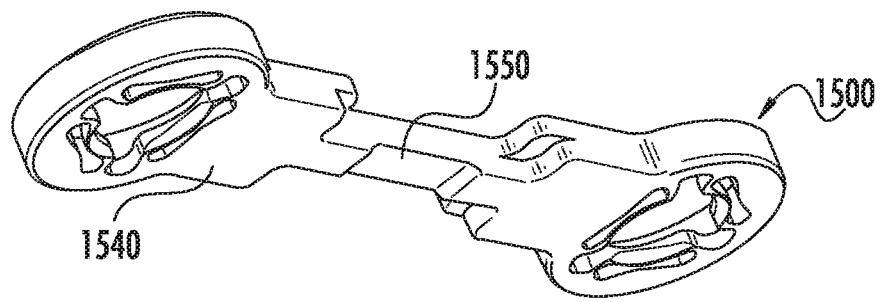
FIG. 75 is a perspective view of the embodiment shown in FIG. 72.

FIGS. 72, 73, 74 and 75 depict an implant embodiment 1500 of the current technology. The implant 1500 may utilize the geometry of the rail or bridge member 1501 as the means for connecting to an inserter. The rail or bridge member may be used to determine or predict the second configuration and may also be used as the connection means for an inserter. The bridge member 1501 has a top surface 1530 that may not have a uniform perimeter. The bridge member 1501 has a perimeter that may include edges 1511, 1512, 1513, 1521, 1522 and 1523. The perimeter of the bridge member may or may not be consistent or uniform with the top surface 1530. As depicted in FIG. 74 the bridge member has a bottom surface 1541, 1542, 1543, and 1544 that may be used to releasably engage an inserter. Engagement between the bridge member geometry and the inserter may maintain the implant 1500 in a first configuration.

Figure 76:
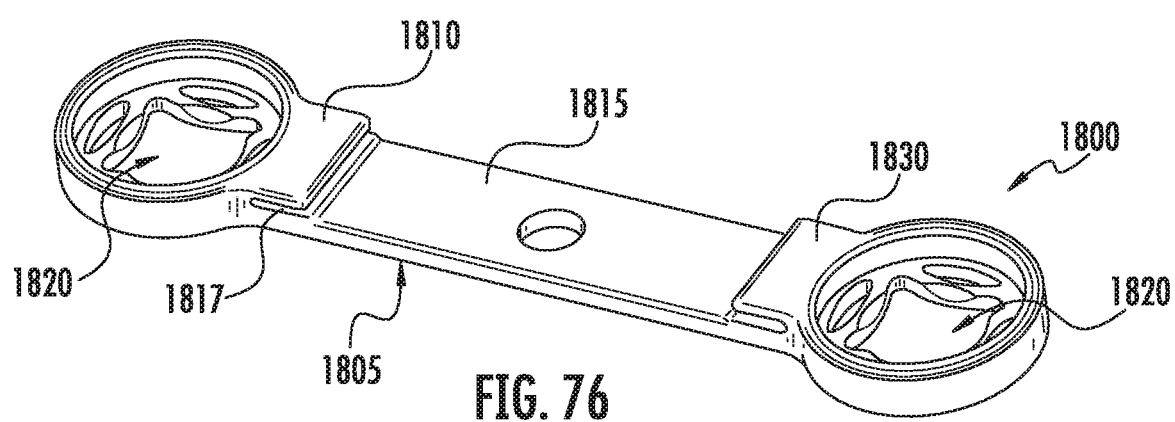
FIG. 76 is a perspective view of a seventeenth embodiment of the current technology depicting an implant with a means for connection to bone engaging features and a means for engaging an inserter.
Figure 77:
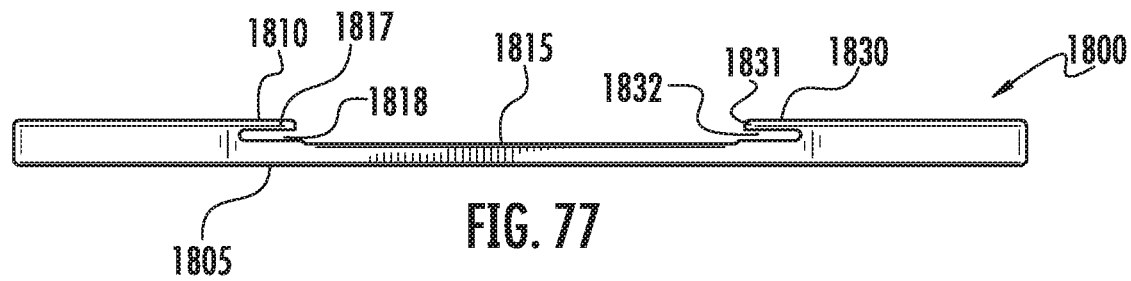
FIG. 77 is a side view of the implant depicted in FIG. 76.

FIGS. 76 and 77 depict an implant embodiment 1800 of the current technology that may have a top loading means of engagement 1810 and 1830 for interaction with a means of insertion. Connection means 1810 and 1830 have upper elements 1817 and 1831, respectively. Connection means 1810 and 1830 may share a bottom element 1815 which may thereby create independent spaces 1818 and 1832 for releasably engaging a means of insertion. In an alternate embodiment, connection means 1810 and 1830 may share a bottom element 1815 and a top element which may thereby create at least one space for releasably engaging a means of insertion.

Figure 78:
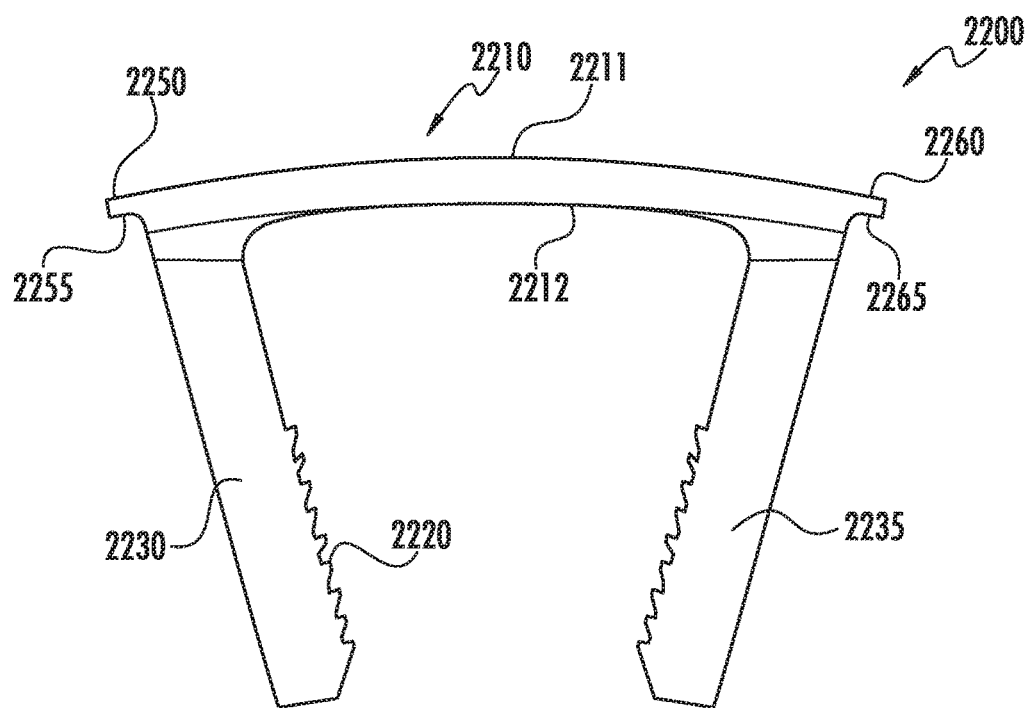
FIG. 78 is a front view of an eighteenth of the current technology depicting an implant with bone engaging features and a means for engaging an inserter.
Figure 79:
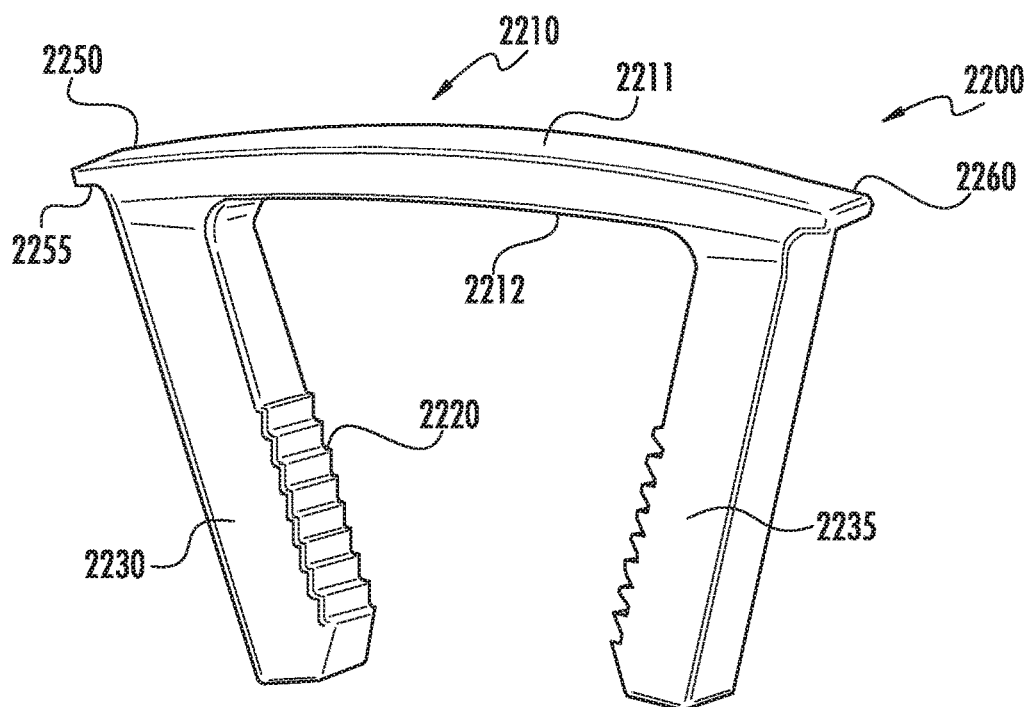
FIG. 79 is a perspective view of the embodiment depicted in FIG. 78.

FIGS. 78 and 79 depict an implant embodiment 2200 that may have bone engaging members 2230 and 2235 integral to the implant bridge 2210. Implant bridge 2210 has an upper surface 2211 and a lower surface 2212. The bone engaging members 2230 and 2235 may have features 2220 that may improve bone purchase or improve pull out strength of the implant 2200 from bone or soft tissue. The implant 2200 may have projections or other connecting means 2250 and 2260 for connection with a means of insertion. The connecting means 2250 and 2260 may have a lower surface 2255 and 2265 respectively that may releasably engage with a means of insertion that may allow the inserter or other means of insertion to be side loading, top loading or pivotably loaded. The means of insertion may maintain a one piece implant in a first configuration thereby allowing a second implant configuration once the implant is disassembled from the implant. The means of insertion may utilize features similar to 2250 and 2260 as described herein in combination with other surfaces such as top surface 2211. This combination of means of insertion may be used to maintain one or more features or arms or projections. This combination of means of insertion may create a bending modality, such as a three point or four point bend, to maintain a specific implant configuration or combination of configurations. A combination of surfaces and means of insertion, such as 2250, may be used on the entire implant or portions of an implant to create or maintain a particular configuration of an implant. For example, a tab such as 2250 and top surface, such as 2211 may be used to maintain one side of an implant or one arm of an implant in a particular configuration. When disassembled, that arm may have a configuration that is different from or the same as the configuration of the rest of the implant.

The present technology includes an implant for generating a multidirectional or multicomponent force across bone or tissue segments. Exemplary embodiments of the current technology are shown in the drawings and discussed below. The implant may be of a configuration similar to a modular staple or bone plate as discussed in the figures. The present technology may employ an apparatus or instrument for inserting the implant that may be pre-assembled or affixed to the implant as shown in FIGS. 84 and 85. The implant or implants could be held in a particular configuration in the packaging that facilitates engagement with the inserter at time of use. Certain embodiments of the current technology may not require the use of an inserter tool, for example an embodiment made of shape memory nitinol may rely on the ability of the user to activate the shape memory nitinol to generate the multidirectional or multicomponent forces.

The implant embodiments described herein may be used in connection with any type of inserter or fixation device, including but not limited to various bone staples, bone plates, etc. that have more than one implant configuration where a force, typically a compressive force, is generated across bone segments.

Figure 80:
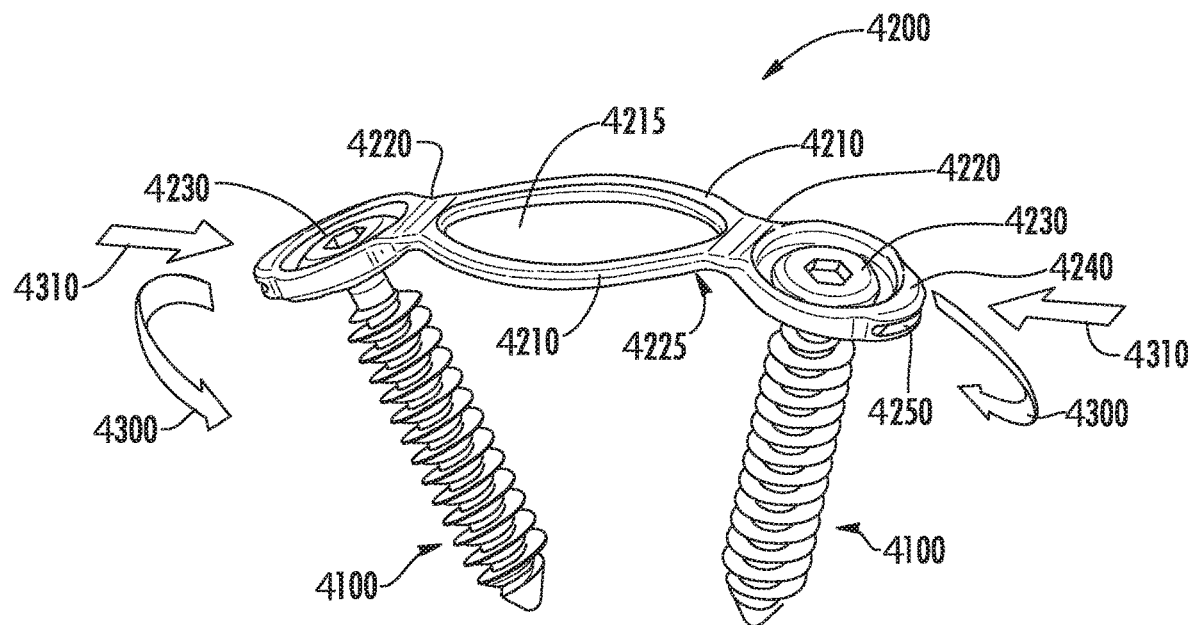
FIG. 80 is a perspective view of a first embodiment of the current technology depicting an implant with bone screws generating compression by two different actions as indicated by the arrows.
Figure 81:
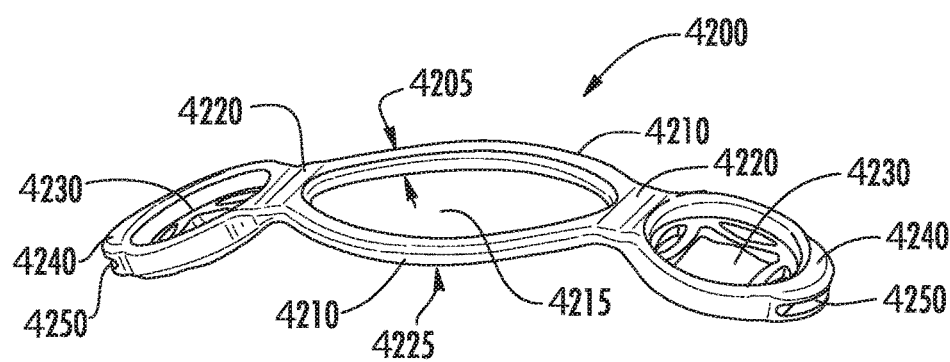
FIG. 81 is a perspective view of a first embodiment of the current technology depicting an implant without bone screws generating compression by two different actions.

FIGS. 80 and 81 show implant 4200. FIG. 80 shows the bone screws 4100 assembled to implant 4200. The implant 4200 is shown in a state that exerts forces shown in the direction of 4300 and 4310. In this exemplary embodiment, the implant 4200 has screw holes 4230 for attaching a bone screw 4100 or other fixation elements. In another embodiment, the implant may have integral staple legs that may be used instead of or in combination with screw holes 4230. (See for example FIGS. 94-96.) Also shown are tabs 4240 that may have a slot 4250 to facilitate attachment to an insertion device. This attachment tab 4240 may be used to hold the implant 4200 with the flexing region 4220 in a neutral position, i.e. the screw holes 4230 are held in a flat orientation. Implant 4200 has a flexing region 4220 that is located between the screw hole 4230 and the bridge member(s) 4210. This flexing region 4220 may have a nonsymmetrical geometry or other features, such as cutout, slots, embossments, ridges, etc., strategically placed to assist in controlling the direction, force and predictability of the flexing region 4220. In this embodiment, the bridge members 4210 and the flexing regions 4220 define a space 4215. The forces may be generated simultaneously or as separate actions. In the exemplary embodiment the forces are generated as separate actions and will simplify the description herein. The first compressive force 4300 may be generated when the flexing region 4220 is allowed to move thereby allowing the screw holes 4230 and bone screws 4100 to converge relative to one another. The compressive force 4300 may be generated by having a superelastic implant with the screw hole regions 4230 manufactured such that they are converging relative to one another when the implant is at rest. Holding the screw hole regions 4230 flat may store the compressive (i.e. converging) energy until they are released and allowed to resume the converged orientation. With the bone screw hole regions 4230 held flat or relatively parallel to the bone, the bone screws 4100 may be inserted into the bone and maintained parallel relative to one another. Once the bone screws are fully seated, the screw holes 4230 may be released from their flat orientation and allowed to resume their converging orientation due to the superelastic aspects of nitinol. In another embodiment, this same effect may be achieved with the shape memory aspects of the nitinol material. In such an embodiment, once the bone screws are fully seated in the implant 4200, the screw holes 4230 may be activated using for example the appropriate activation temperature (e.g. body heat or an external temperature source) and allowed to resume their converging orientation due to the shape memory aspects of nitinol. The magnitude of the force 4300 may be dependent on the material of choice, the overall geometry of the implant and or the surgical technique. This compressive force 4300 may generate a compressive force that is higher in magnitude at the level of the tips of the screws 4100 than at the level of the bone plate 4225. Compressive force 4310 may be generated when the bridge members 4210 are allowed to displace, in this case outwardly, to an open position. This displacement may change the shape of the space 4215 thereby creating force 4310 which may draw the screw holes 4230 closer together generating a compressive force that may have a greater magnitude at the level of the bone plate 4225 than the level of the tips of the bone screws 4100.

Similar to the mechanism that may be used to generate force 4300, force 4310 may be generated by having a superelastic implant with the bridge members 4210 manufactured such that they may be in an outward or open position when the implant is at rest. Holding the bridge members 4210 in a closed position may store the compressive (i.e. displacement) energy until they are released and allowed to resume the open position or outward orientation. With the bone screws 4100 fully seated and secured in bone, the bridge members 4210 may be released from their closed orientation and allowed to resume their open orientation due to the superelastic aspects of nitinol. This movement from the closed position to the open position may create a change in the relative spacing between the bone screws 4100 thereby generating a displacement that may result in a compressive force 4310. In another embodiment, this same effect may be achieved with the shape memory aspects of the nitinol material. In such an embodiment, once the bone screws are fully seated in the implant 4200, the bridge members 4210 may be activated using the appropriate activation temperature (e.g. body heat or an external temperature source) and allowed to resume their open position or outward orientation due to the shape memory aspects of nitinol. The magnitude of the force 4310 may be dependent on the material of choice, the overall geometry of the implant (e.g. thickness, width, height, etc.) and or the surgical technique. The unique combination of the forces 4300 and 4310 may create a more uniform and overall greater compressive force than the forces would individually. The current state of the art is to have an implant device that will generate only one compressive force. The description of the compressive forces 4300 and 4310 is not intended to be limiting. The forces generated may or may not be uniform or may have varying magnitudes. The particular order of forces generated is also not limiting. The current technology also includes any order or combination of more than one force magnitude and vector.

FIG. 81 shows the implant 4200 in the same condition as FIG. 80 but without bone screws 4100 in place. This figure shows screw holes 4230 that are locking screw holes in this particular embodiment. This embodiment has two bridge members 4210 that create a space 4215. Based on the description of the technology herein, those skilled in the art will understand that there are numerous shapes that may be created by the bridge members. Furthermore, it is possible to have an implant 4200 that may have multiple bridge members or a single bridge member. The single bridge member may be manipulated such that the fixation means (i.e. bone screw, staple legs, etc.) may be brought closer together to create, in this case, a compressive force. In the case of a single bridge member, space 4215 may or may not exist.

The positioning and or orientation and or geometry of opening 4215 relative to the bridge members 4210 and flexing regions 4220 may provide a means for distributing the required stresses within the implant 4200 to achieve a desired compressive force. The position and geometry of opening 4215 may be altered within the scope of this technology to manipulate the stress distribution to achieve the desired performance. Within the scope of this technology, the position and geometry of opening 4215 may be altered in combination with the thicknesses 4205 to manipulate the stress distribution to achieve the desired performance. The amount of desired force generated by the current technology may be accomplished by manipulating individual aspects of the implant geometry and their relative orientations to one another. The geometry and relative orientation of thicknesses 4205 may be altered to manipulate the stress distribution within the implant bridges 4210 to achieve the desired performance. The geometry and relative orientation of thicknesses 4205 may be altered in combination with altering the geometry and relative orientation of the flex regions 4220 to manipulate the stress distribution within the implant 4200 to achieve the desired performance or force generated. The geometry and relative orientation of thicknesses 4205 may be altered in combination with altering the geometry and relative orientation of flex region 4220 and may be in combination with altering the geometry and relative orientation of opening 4215 to manipulate the stress distribution within the implant 4200 to achieve the desired performance and force generation. Furthermore, the implant widths 4208, 4209, 4211, 4212, 4213 and or 4214 as shown in FIG. 82A may also be manipulated in geometry and or orientation either as independent variables or in combination with the previously described aspect or aspects of the implant to manipulate the stress distribution within the implant 4200 to achieve the desired performance or force generation.

Figure 82A:
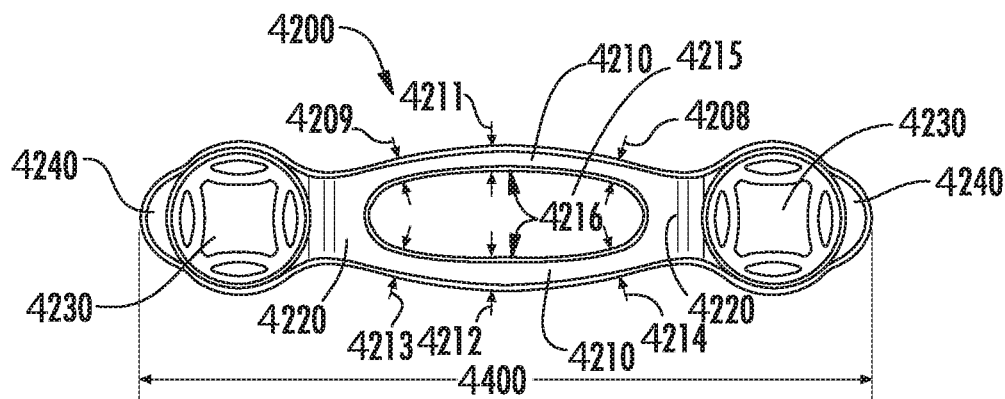
FIG. 82A is a top view of a first embodiment of the current technology depicting an implant without the bone screws inserted in a first configuration showing no compressive force generated.

FIG. 82A depicts a top view of the implant 4200 for this particular embodiment. The implant 4200 is shown as it would be held prior to releasing and or activating any of the superelastic and or shape memory mechanisms, i.e. in this case shown with no generated forces as it may be held in an inserter for implantation, for clarity the inserter is not shown in this particular view. For clarity, the fixation means bone screws 4100 are not included in FIGS. 82A, 82B or 82C. The implant 4200 may have tabs 4240 or other means for holding the implant in a flat, non-force generating geometry. This particular embodiment depicts attachment means 4230 as locking holes for bone screws 4100. However, based on the description of the technology herein, those skilled in the art will understand that the fixation means may be integral to the implant 4200, e.g. staple legs, or may include other fixation means such as pegs, blades or other types of bone screws. The flexing region 4220 may or may not be of uniform width and or thickness. Flexing region 4220 and or the bridge members 4210 may have certain features, such as holes, slots, keyways, ribs, bosses, etc. to facilitate and assist in a predictable means and method of flexing. The space 4215 is adjacent to the bridge member(s) 4210 that have widths 4211 and 4212. The width of the bridge member 4210 may or may not be uniform. Width 4211 may be greater than or less than width 4212. The bridge member widths 4208 and 4209 and widths 4213 and 4214 may or may not be the same. It is possible that some bridge member widths may be the same while others are greater than or less than the remaining widths. The current embodiment is considered to be made from nitinol or other materials with shape memory or super-elastic material properties, although other materials may achieve the same effect.

Figure 82B:
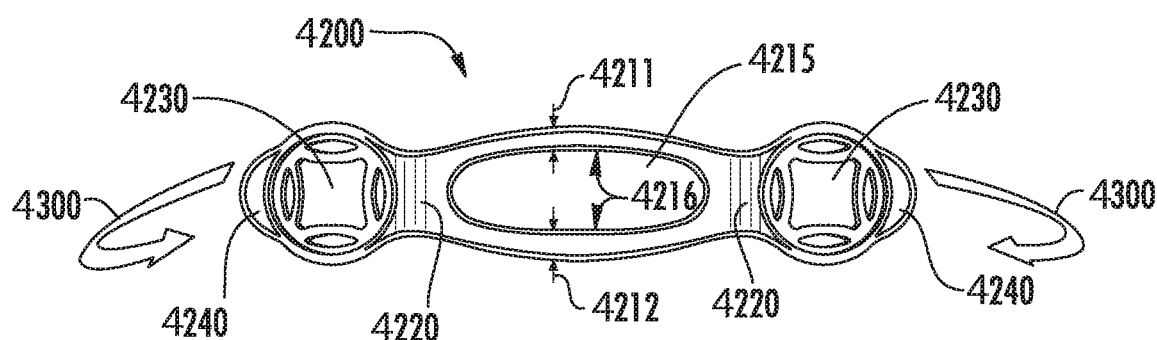
FIG. 82B is a top view of a first embodiment of the current technology depicting an implant without the bone screws in a second configuration showing a first compressive force being generated.
Figure 82C:
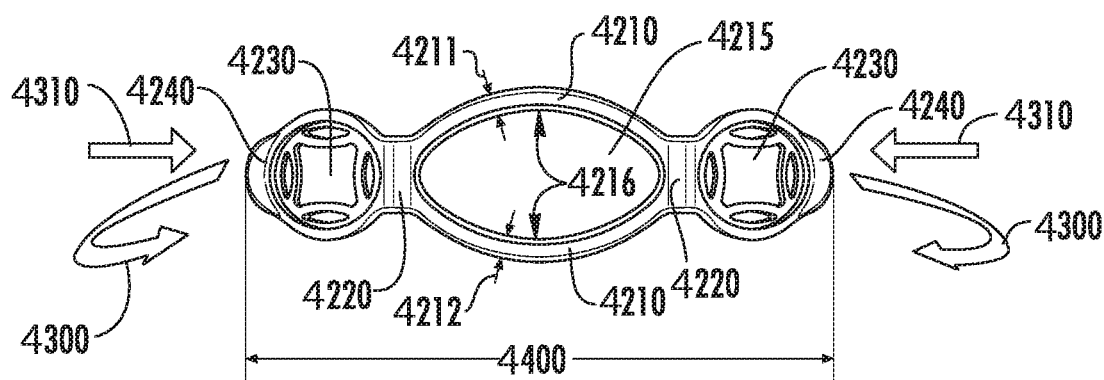
FIG. 82C is a top view of a first embodiment of the current technology depicting an implant without the bone screws in a third configuration showing a second compressive force being generated while maintaining the first compressive force.

FIG. 82B is a top view of implant 4200 in a second configuration showing the first compressive force 4300. Compressive force 4300 may be in a direction that causes the flexing region(s) 4220 and or the fixation means, such as bone screws 4100 or other such fixation means, to converge (i.e. the tips of the bone screws 4100 are brought closer together). FIG. 82C is a top view of implant 4300 in a third configuration showing the second compressive force 4310 and the first compressive force 4300. The distance 4216 between bridge members 4210 has increased while the overall width 4400 of implant 4200 has decreased. In alternate embodiments, the distance 4216 may increase or decrease as needed to generate a particular force. Compressive force 4310 may be in a direction that shortens the distance between the flexing region(s) 4220 and or the fixation means, such as bone screws 4100 or other such means. The order in which the implant generates the various forces may be irrelevant. In this exemplary embodiment force 4300 is generated before force 4310. The opposite is also possible. Likewise the relative magnitudes of the forces generated is not limiting in nature. One force may be more or less than the other forces generated. As previously described herein, the relative magnitude and direction of the force or forces generated may depend on the orientation of the implant, the material or combination of materials used in construction, the geometry of the various features of the implant and or the surgical technique. The relative magnitude and direction of the force or forces generated may also be a product of the superelastic and or shape memory properties of a material such as nitinol. The superelastic and or shape memory properties of the material may allow energy to be stored in one configuration only to be released when the implant is allowed to resume or attempt to resume it's at rest or zero stress configuration. One embodiment of the current technology may combine the use of the superelastic and shape memory properties of the nitinol material. For example one force may be generated using the superelastic properties and a second force may be generated using the shape memory properties. In this embodiment the first force 4300 and the second force 4310 both remain present in the final state or configuration of the implant.

Figure 83A:
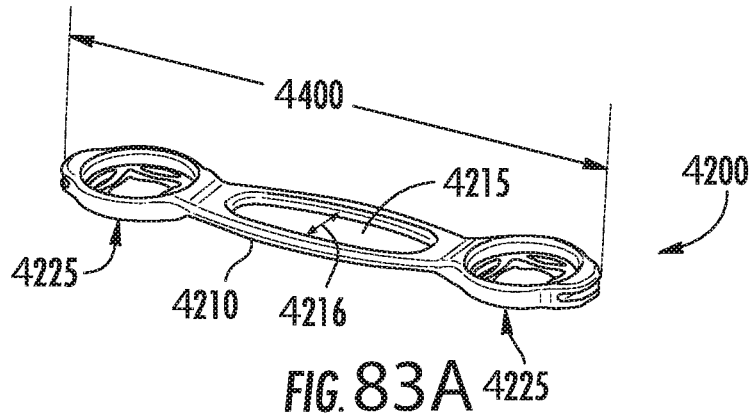
FIG. 83A is a perspective view of a first embodiment of the current technology depicting an implant without the bone screws inserted in a first configuration showing no compressive force generated.
Figure 83B:
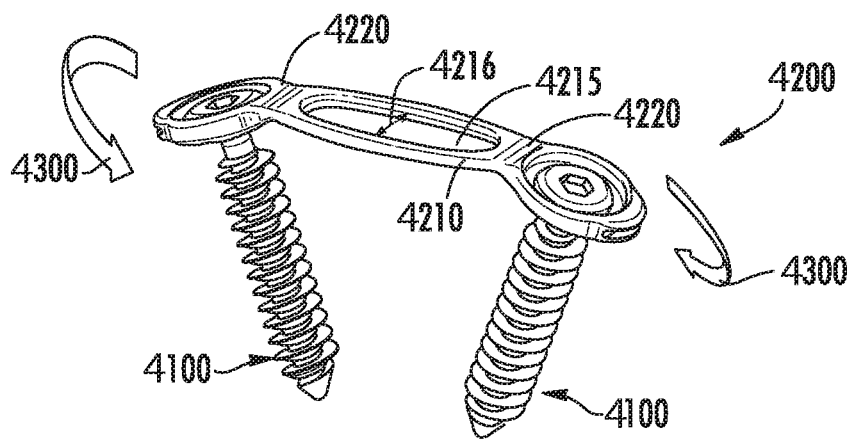
FIG. 83B is a perspective view of a first embodiment of the current technology depicting an implant with bone screws inserted in a second configuration showing a first compressive force being generated by convergence of the bone screws.

FIG. 83A depicts a perspective view of the implant 4200 for this particular embodiment. The implant 4200 is shown as it would be held prior to releasing and or activating any of the superelastic and or shape memory mechanisms, i.e. in this case shown with no generated forces for example as it may be held in or by an inserter for implantation, for clarity the inserter is not shown in this particular view. For clarity, the fixation means bone screws 4100 are not included in FIG. 83A. FIG. 83B is a perspective view of implant 4200 shown with the bone fixation means, bone screws 4100. The implant 4200 and bone screws 4100 are shown with force 4300 that results in the bone screws 4100 converging relative to each other to generate a compressive force. One fixation means may converge more or less than another, or one or more may not converge at all. The force 4300 generates a net convergence that may or may not be equally distributed between the fixation means. In some embodiments, three or more fixation means may be utilized. This could be bone screws, staple legs, pegs, blades, or some combination thereof. It may be desirable to have some or all of the fixation means converge. It's possible to have certain fixation members move in a particular direction, while others may or may not move in an alternate direction.

FIG. 83B is a perspective view of implant 4200 in a second configuration showing the first compressive force 4300. Compressive force 4300 may be in a direction that causes convergence of the flexing region(s) 4220 and or the fixation means, such as bone screws 4100 or other such fixation means.

Figure 83C:
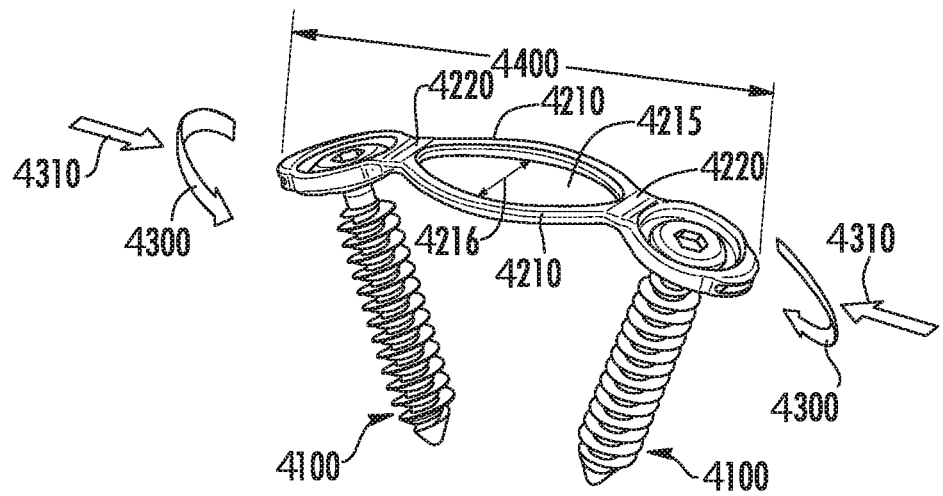
FIG. 83C is a perspective view of a first embodiment of the current technology depicting an implant with bone screws inserted in a third configuration showing a second compressive force being generated by displacement of the bridge member while maintaining the first compressive force.

FIG. 83C is a perspective view of implant 4200 in a third configuration showing the second compressive force 4310 and the first compressive force 4300. The distance 4216 between bridge members 4210 has increased while the overall width 4400 of implant 4200 has decreased. In alternate embodiments, the distance 4216 may increase or decrease as needed to generate a particular force. As previously described, force 4310 may be in a direction that shortens the distance between the flexing region(s) 4220 and or the fixation means, such as bone screws 4100 or other such means. The order in which the implant generates the various forces may be irrelevant. In this exemplary embodiment, force 4300 is generated before force 4310. The opposite is also possible. Likewise the relative magnitudes of the forces generated is not limiting in nature. One force may be more or less than the other forces generated. In this embodiment the first force 4300 and the second force 4310 both remain present in the final state or configuration of the implant.

Figure 84A:
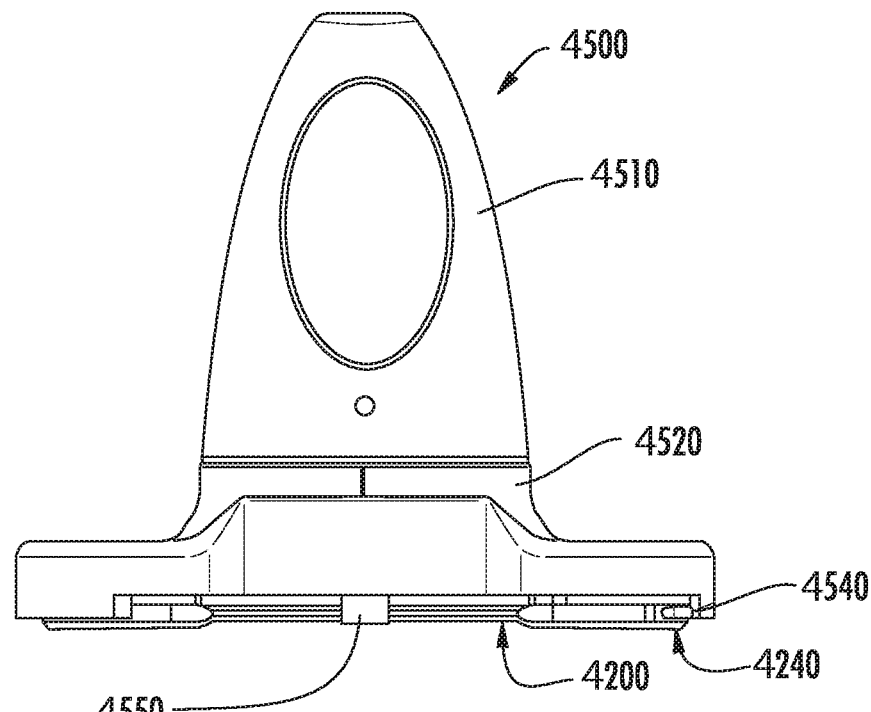
FIG. 84A is a front view of a first embodiment of the implant of the current technology showing attachment to an apparatus for insertion and maintaining a first configuration of the implant.

FIG. 84A is a front view of implant 4200 assembled to an inserter 4500. FIG. 84A shows implant 4200 assembled to inserter 4500. The inserter 4500 may have a top 4510 and a base 4520. The inserter 4500 is releasably engaged to the implant 4200. The inserter 4500 has a means 4540 that attaches to the implant tab 4240 in slot 4250 for maintaining the implant 4200 in a flat configuration. Inserter 4500 has a means 4550 for engaging implant 4200 to maintain the distance 4216 in closed state.

Figure 84B:
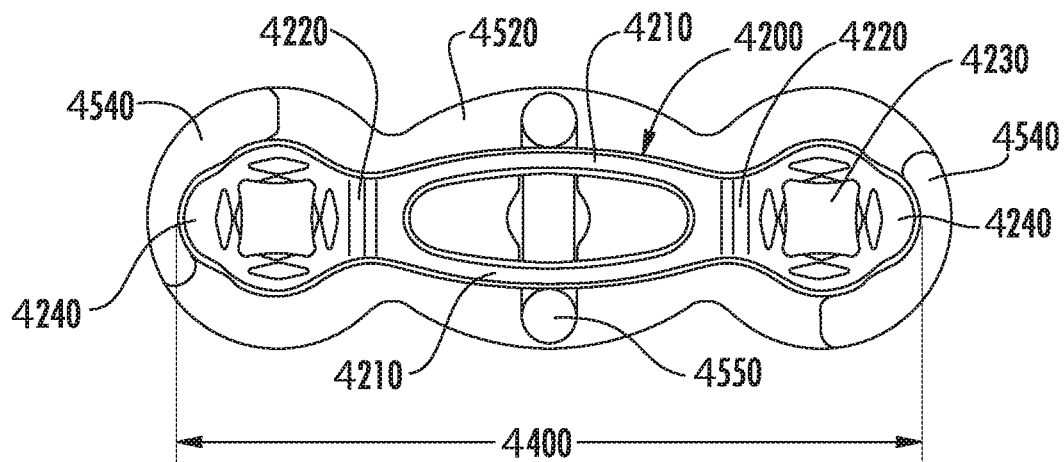
FIG. 84B is a bottom view of a first embodiment of the implant of the current technology showing attachment to an apparatus for insertion and maintaining a first configuration of the implant.

FIG. 84B is a bottom view illustrating the implant 4200 releasably attached to inserter 4500. The inserter base 4520 has an attachment means 4540 that engages slot 4250 in the implant attachment means 4240. In this embodiment, in the perspective shown, when the inserter 4500 is rotated, the inserter engagement means 4540 may be withdrawn from the slot 4250 (not shown) in the implant attachment means 4240. When released, the superelastic properties of the implant 4200 will allow the flexing regions 4220 of the implant 4200 to move towards their zero stress condition or in other words, will allow regions 4220 of the implant 4200 to flex which may cause the bone screw holes 4230 and attached bone screws 4100 (not shown) to converge. This action may generate a compressive force 4300. As further shown, inserter base 4520 has a retractable means 4550 that may maintain the implant bridges 4210 in their closed or loaded configuration. When the attachment means 4550 is retracted or disengaged from the implant bridge members 4210, in this embodiment, the superelastic properties allow the bridge members 4210 to open or move to their outward configuration. This action may cause the screw holes 4230 to move relatively closer to each other thereby generating the compressive force 4310. The order in which the implant may be released from the inserter instrument is not limiting. Attachment means 4550 may be released first which may cause the implant bridge members 4210 to open or move to their outward configuration. This action may cause the screw holes 4230 to move relatively closer to each other thereby generating a displacement. This displacement may shorten the overall width 4400 of implant 4200. This shortening may be of sufficient magnitude to withdraw the inserter attachment means 4540 from the slots 4250 of the implant attachment means 4240 which may obviate the need to rotate the inserter 4500 in a way that would release inserter attachment means 4540 from the slots 4250 of the implant attachment means 4240.

Figure 85A:
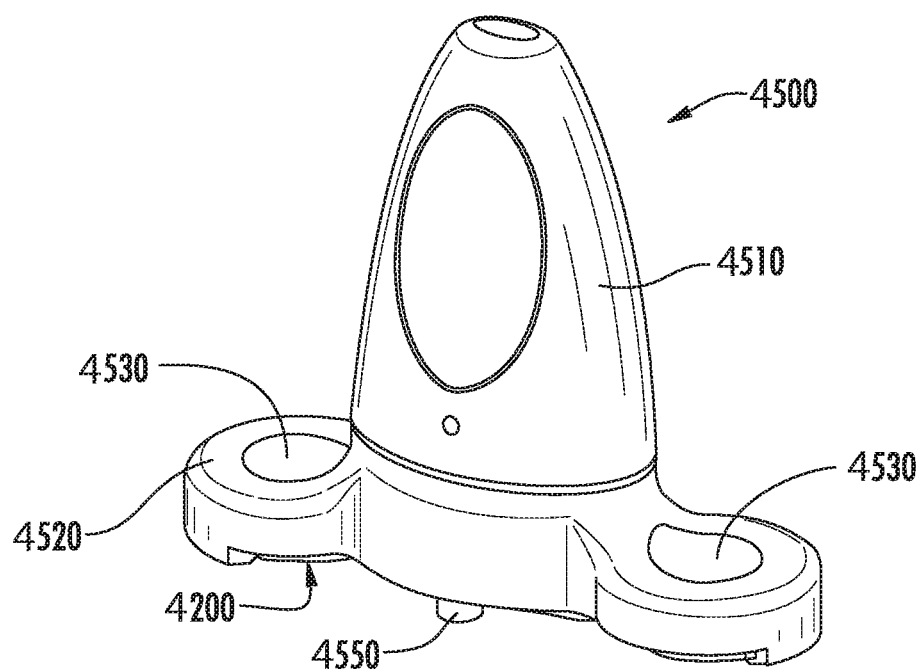
FIG. 85A is a top perspective view of FIG. 84A.
Figure 85B:
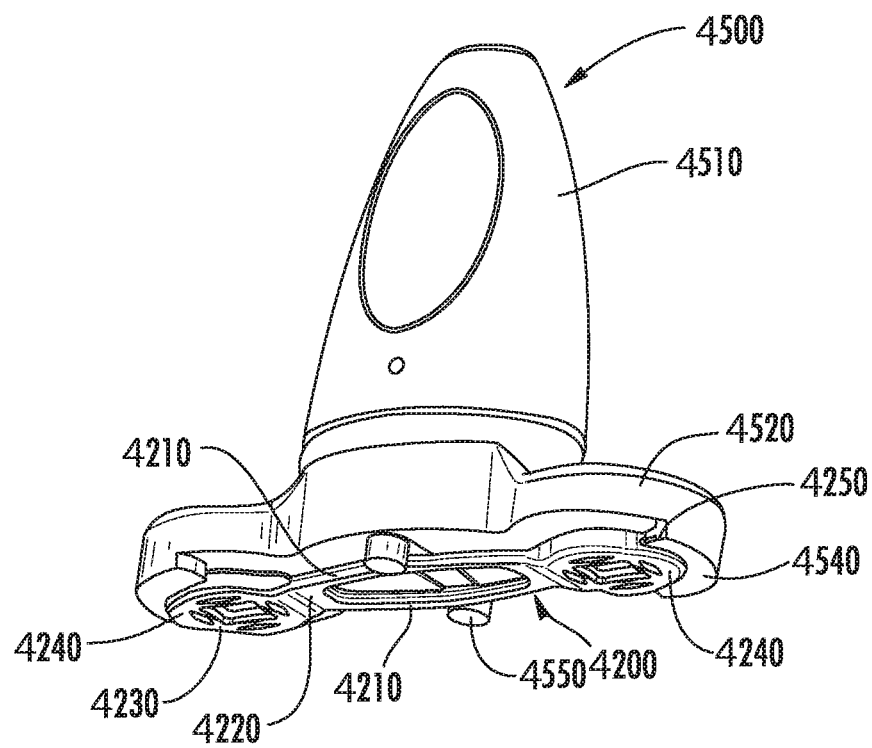
FIG. 85B is a bottom perspective view of a first embodiment of FIG. 84A.

FIG. 85A is a top perspective view of implant 4200 assembled to inserter 4500. The inserter 4500 may have a top 4510 and a base 4520. The inserter 4500 is releasably engaged to the implant 4200. The inserter 4500 has a means 4540 that attaches to the implant tab 4240 in slot 4250 for maintaining the implant 4200 in a flat configuration. Inserter 4500 has a means 4550 for engaging implant 4200 to maintain the distance 4216 in closed state. FIG. 85B is a bottom perspective view further describing one possible embodiment of the inserter 4500 attached to implant 4200. This view shows inserter attachment means 4550 engaged with the implant bridges 4210 and maintaining them in a first configuration or closed state. Also described in FIG. 85B is the inserter attachment means 4540 which may be slidably engaged in slot 4250 of implant attachment means 4240 maintaining regions 4220 and bone screw holes 4230 in a flat orientation or configuration. To those skilled in the art, it will be obvious based on the description of the technology herein that there are numerous mechanisms and embodiments for releasably attaching to the implant to maintain the implant in a loaded and or stressed state prior to releasing the implant and or allowing the implant to achieve a force generating state. FIG. 85A shows holes 4530 that permit insertion of the bone screws 4100 or other fixation means.

Figure 86A:
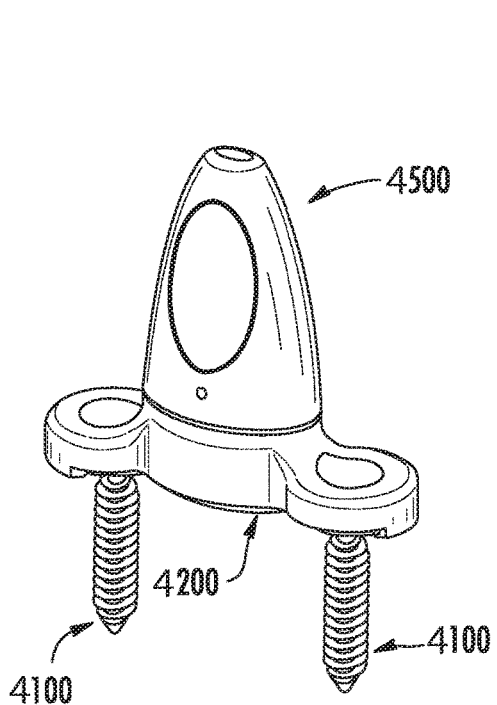
FIG. 86A is a perspective view of the first embodiment of the implant attached to the insertion/holding device, shown with bone screws inserted and prior to generation of the first compressive force.
Figure 86B:
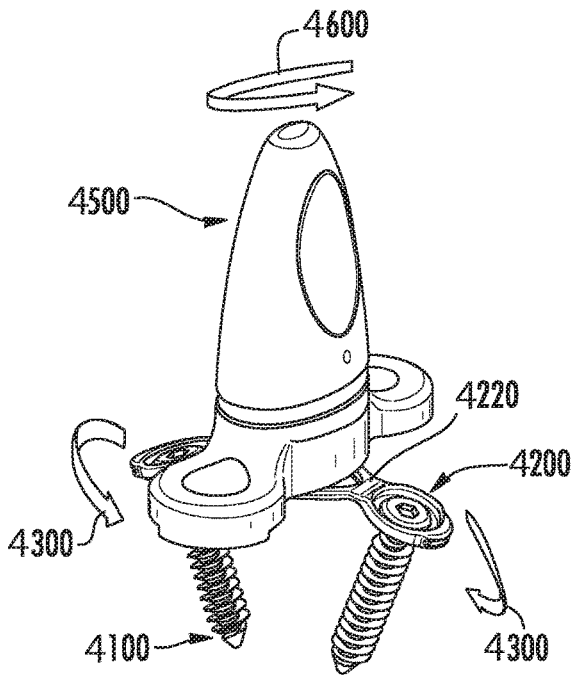
FIG. 86B is a perspective view of the first embodiment of the implant attached to the insertion/holding device shown with bone screws inserted and after generation of the first compressive force as a result of allowing the bone screws to converge but prior to generation of the second compressive force.
Figure 86C:
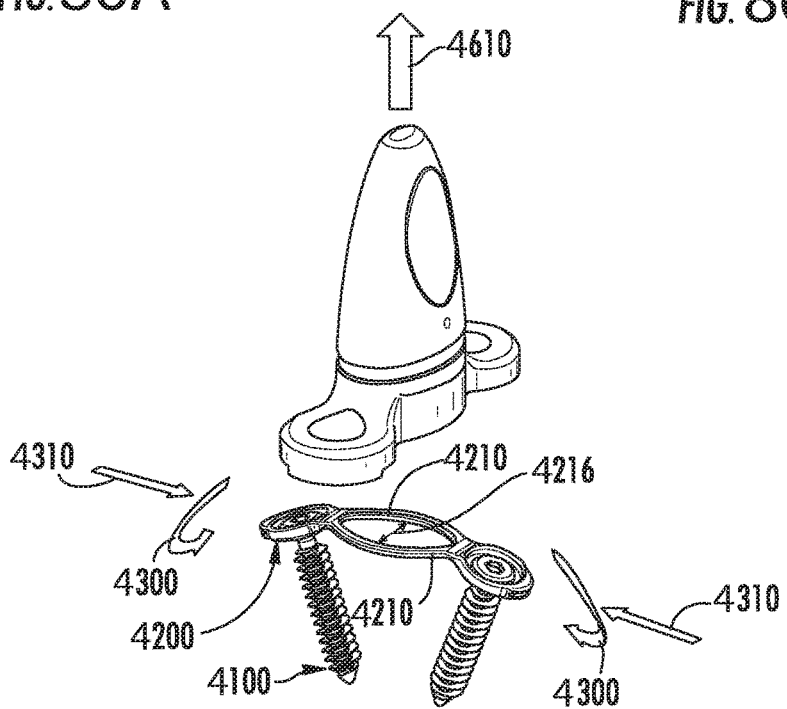
FIG. 86C is a perspective view of the first embodiment of the implant attached to the insertion/holding device, shown with bone screws inserted and after generation of the first compressive force as a result of allowing the bone screws to converge and after generation of a second compressive force as a result of allowing the ends of the implant to displace closer together generating a second compressive force at the bridge of the implant.

FIG. 86A is a perspective view of the inserter 4500 shown releasably attached to implant 4200 with bone screws 4100 in place. As shown, the inserter 4500 maintains the implant in a neutral state with the fixation means, bone screws 4100, in a parallel, non-force generating configuration. FIG. 86B shows inserter 4500 being released from implant 4200 by a twisting motion 4600. This motion 4600 releases the engagement means 4540 from the implant attachment tabs 4240 while maintaining attachment means 4550 with the implant. Once the engagement means 4540 releases the implant, the flexing region 4220 is permitted to flex thereby generating force 4300. In this particular exemplary embodiment, the force 4300 causes the bone screws 4100 to converge thereby generating a compressive force across the bone segments. FIG. 86B illustrates the implant 4200 and inserter 4500 prior to fully releasing the implant 4200 from inserter 4500. FIG. 86C is a perspective view of the first embodiment of the implant 4200 detached from the insertion/holding device 4500. The first releasing action 4600 has already been completed and as shown a second releasing action 4610 is used to fully disengage the inserter 4500 from the implant 4200 thereby allowing the bridge members 4210 to move, increasing the distance 4216 and drawing the bone fixation means 4100 closer together which decreases the overall width 4400 of the implant resulting in a force 4310. The releasing action 4610 may allow the inserter attachment means 4550 to be retracted within the inserter base 4520. In this particular exemplary embodiment, force 4310 is an additional compressive force further compressing the bone segments.

The previous description is for a particular embodiment that is considered to be manufactured from a material with elastic properties, such as super elastic nitinol. However this description is not intended to be limiting in nature. Those skilled in the art will understand based on the description of the technology herein that the same may be accomplished using a material for example with shape memory aspects, such as shape memory nitinol. Other materials currently exist or may exist that have desirable material properties that will achieve the intended function of the current technology.

Still other embodiments of the current technology may provide more than one force that is generated simultaneously as opposed to the stepwise manner as described herein. The order in which the forces are generated is also not intended to be limiting in nature. The use of an inserter/holding device may or may not be optional. The specific details of the inserter may vary greatly depending of the chosen embodiment. The exemplary embodiment described herein, expands on a two force configuration. Those skilled in the art will find it obvious based on the description of the technology herein that multiple forces may or may not be beneficial depending on the intended application. They will also find it obvious that the magnitude and direction of the resulting force vectors may or may not be equivalent or may or may not be additive. It may be beneficial to have multiple forces generated to create more uniform and predictable forces than those currently available in the state of the art devices. Still further, the exemplary embodiment described herein considers a design with two fixation means or bone screws. Other embodiments may include two or more fixation means that may be of the same style (such as bone screws, bone pegs, blades, staple legs, etc.) or of varying styles or some combination thereof. For fixation means that are modular in nature, they may or may not be made of the same material as the implant described herein.

Figure 87:
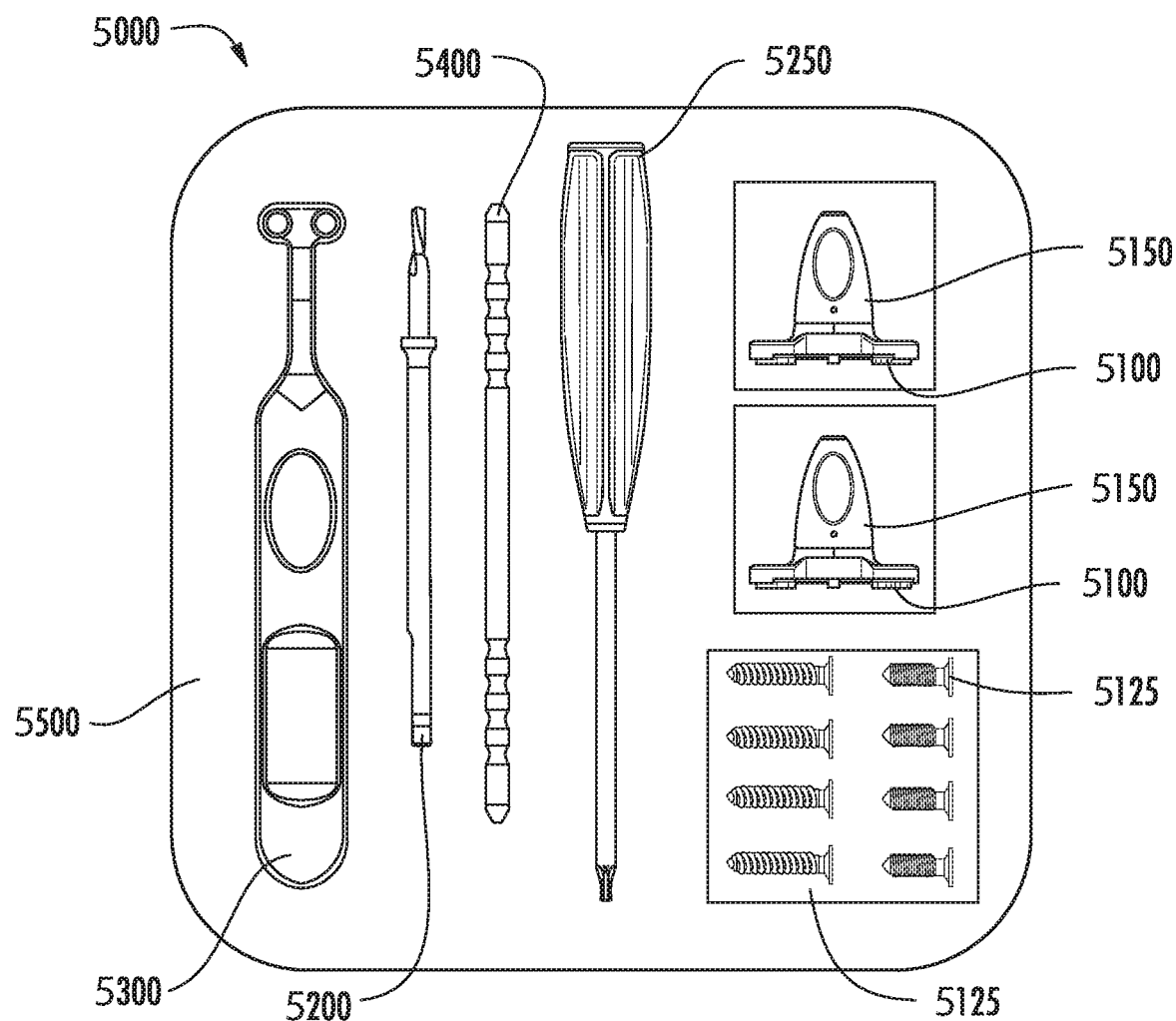
FIG. 87 is a top view of an implant kit that may be provided for inserting the implant of the current technology into bone segments.

Referring to FIG. 87, the implant of the current technology may be packaged as an implant kit with the associated instruments needed for a successful implantation. A kit of this sort may be provided as a sterile single use kit for efficiency and cost effectiveness. Such a kit may include the implant or implants, bone screws or other means for fixing the plate to the bone, the necessary drills or reamers for preparing the bone for receiving the implant and bone screws, any necessary drill guides and drivers and an inserter for facilitating implantation of the implant into the bone. FIG. 87 shows one embodiment of an implant kit 5000 that may be used to provide the end user with the implants and necessary associated instruments for successfully implanting an implant of the current technology. Such a kit may include one or more implants 5100 similar to the embodiments described herein preassembled to an inserter 5150. The kit may also include bone screws 5125 of various lengths and or diameters, a drill 5200, a drill guide 5300, a driver 5250 and a provisional fixation pin 5400. The kit may also include an insertion tool or inserter 5150 for facilitating insertion of the implant 5100 into a bone segment(s). One embodiment of the kit may have the implant 5100 preassembled to the insertion tool 5150. The kit may be assembled in a tray 5500. Once the end user opens the kit, the surgical technique may include the following steps. After exposure of the operative site, the osteotomy or fracture may be reduced and held in place. The drill guide or reamer guide may be placed across the fusion site with both guide tubes against the bone. The first hole is drilled to final depth by advancing the drill or reamer to a predetermined depth or until a depth stop hits the top of the guide. A provisional fixation pin may be placed in the prepared hole to help maintain reduction while the additional holes are prepared. Another option may allow the holes to be prepared directly through the inserter 5150 obviating the need for an ancillary drill guide. This step of preparing the bone may include the need or use of a depth gage to select the appropriate sized bone screw. Once the holes have been prepared, the implant 5100 may be fixed to the bone, with bone screws 5125. The bone screws 5125 may be inserted through the implant and into the bone segments. The implant 5100 may be preassembled or loaded onto the inserter tool 5150. The implant 5100 and bone screws 5125 should be fully inserted until flush against the surface of the bone. The implant may then be released from the inserter tool thereby generating the prescribed forces and generating compression across the bone segments. Once implantation is complete the inserter and remaining instruments may be discarded or recycled.

Figure 88A:
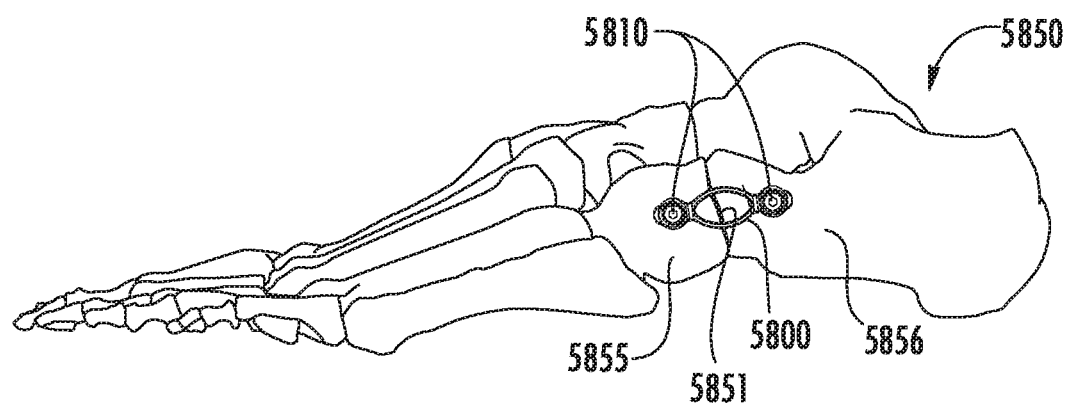
FIG. 88A is a side view of one embodiment of the current technology in one possible location on the bones of the foot.
Figure 88B:
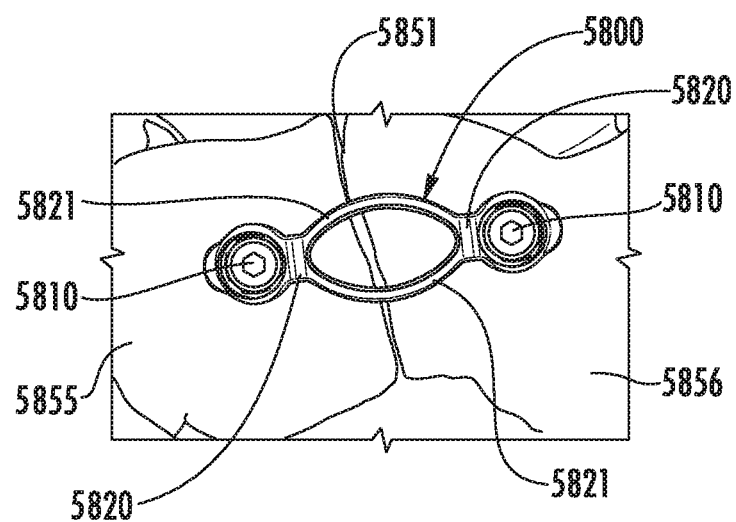
FIG. 88B is a close-up of FIG. 88A showing one embodiment of the current technology in one possible location on the bones of the foot.
Figure 89:
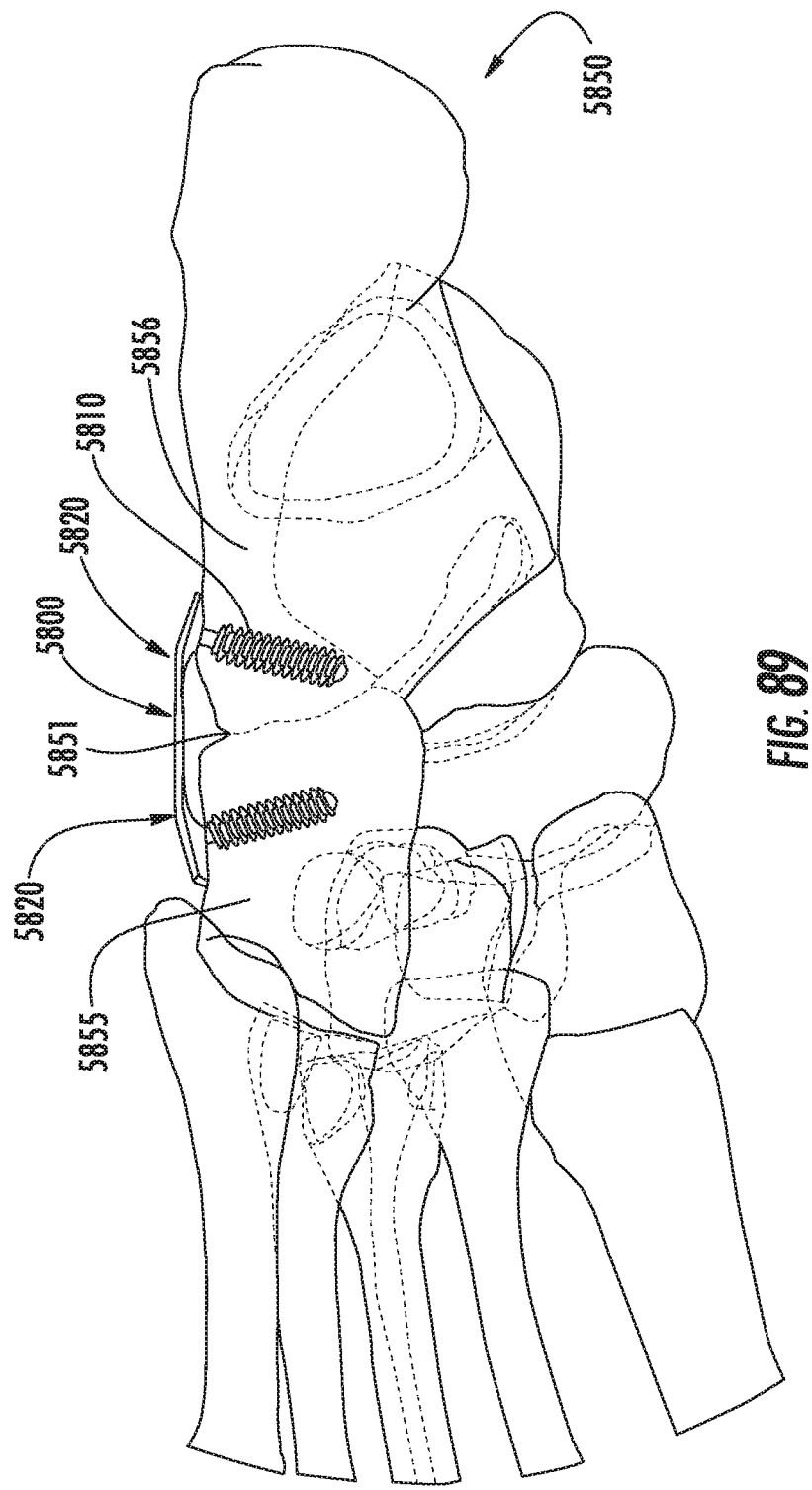
FIG. 89 is a top view of the foot shown in FIGS. 88A and 88B showing in section one embodiment of the current technology in one possible location on the bones of the foot.

FIGS. 88A and 88B illustrate one embodiment of the current technology 5800 in one possible location on the bones of the foot 5850 that may have been positioned according to the technique described herein. FIG. 88A illustrates a side view of foot 5850 with the implant 5800 spanning the joint line or fracture line 5851. The implant 5800 may be fastened to the bones 5855 and 5856 with bone screws 5810. FIG. 88B is a close up view of bones 5855 and 5856 illustrating the implant 5800 spanning joint line or fracture line 5851. The implant 5800 may be fastened to the bones 5855 and 5856 with bone screws 5810. Is this exemplary embodiment, the implant 5800 may have bridge members 5821 in an open configuration that may cause a shortening or displacement between the relative positions of bone screws 5810 which may bring the two bones 5855 and 5856 in apposition for possible fusion of joint line or fracture line 5851. The figure further shows flex region 5820 of implant 5800 in a flexed position that may bring the bone screws 5810 in a converging position relative to one another thereby possibly bringing bones 5855 and 5856 even further into apposition for possible fusion of joint line or fracture line 5851. FIG. 89 is a top view of foot 5850 and bones 5855 and 5856. This figure shows flex regions 5820 of implant 5800 in a flexed position that may bring the bone screws 5810 in a converging position relative to one another thereby possibly bringing bones 5855 and 5856 into apposition for possible fusion of joint line or fracture line 5851.

Figure 90:
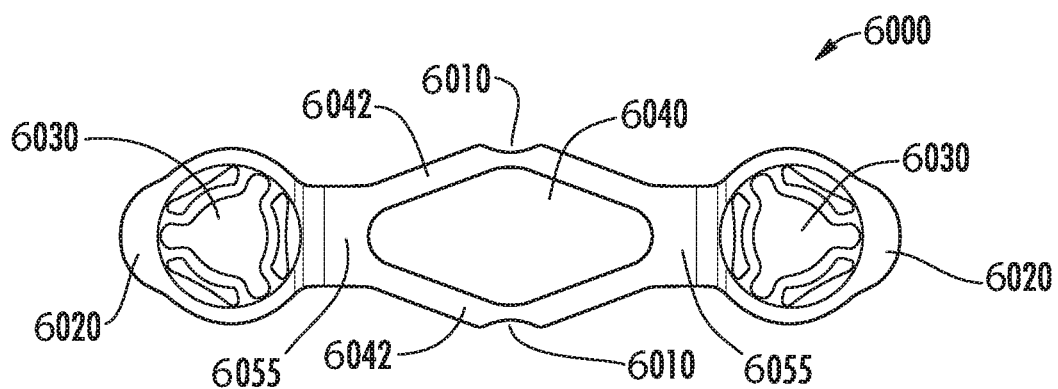
FIG. 90 is a top view of a second embodiment of the current technology depicting an implant with means for attaching to instrumentation and a means for attaching to one or more bone engaging means.
Figure 91:
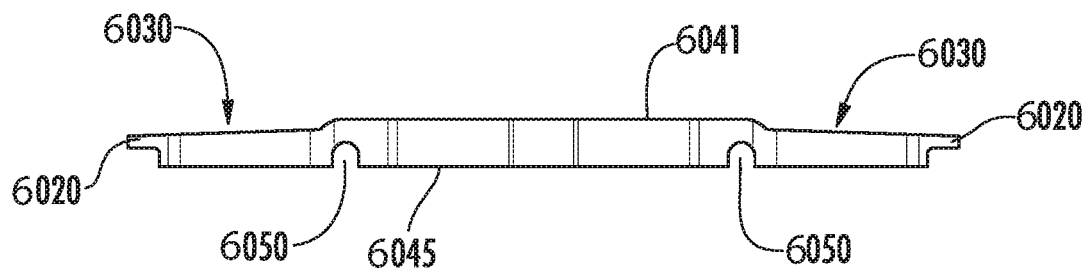
FIG. 91 is a side view of the second embodiment of FIG. 90 depicting regions and or features for controlling at least one direction of force.
Figure 92:
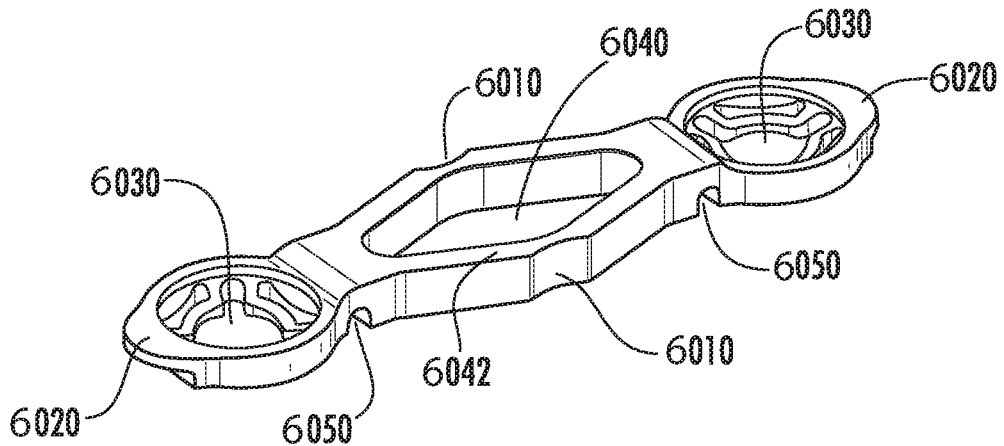
FIG. 92 is a perspective view of the second embodiment shown in FIGS. 90 and 91.

FIG. 90 shows a top view of a second embodiment of the current technology, implant 6000, having a top surface 6041 and a space 6040. FIGS. 90, 91 and 92 show the implant 6000 in a flat configuration. Space 6040 is defined by bridge members 6042 and flexing regions 6055. As previously described herein, the shape of space 6040 may vary by either contracting or expanding to create a movement or force in a predetermined direction. Implant 6000 has means 6030 for engaging bone fixation means of varying sorts. For example, means 6030 may be non-locking holes, threaded locking holes, interference holes, tapered holes or other mechanical means for connecting bone engagement means such as pegs, screws, blades, etc. Implant 6000 may have one or more means 6020 for engaging a means of insertion as previously described herein. Implant 6000 may have means 6010 for engaging or indexing the implant with an inserter, driver or other means of insertion or holding. Means 6010 may also be used to change the shape of space 6040. In this embodiment, means 6010 may be used to compress the space 6040 thereby creating a force that will maintain means 6030 apart relative to one another. This configuration may be maintained while the bone fixation means are inserted into bone. Once the implant 6000 is affixed to the bone with the bone fixation means, the means by which the means 6010 are maintained apart may be released thereby allowing the distance between means 6030 to shorten creating a compressive force. FIGS. 91 and 92 show implant 6000 having a top surface 6041 and a bottom surface 6045. Bottom surface 6045 may be interrupted by means 6050. Means 6050 is positioned to provide a predetermined bend region for predictably controlling a motion and or direction of an alternate action or configuration of implant 6000. In this particular embodiment, means 6050 is shown positioned between the space 6040 and bone fixation means 6030 but may be positioned at any place on the implant where it is desirable to control the direction and motion of a first or second configuration.

Figure 93:
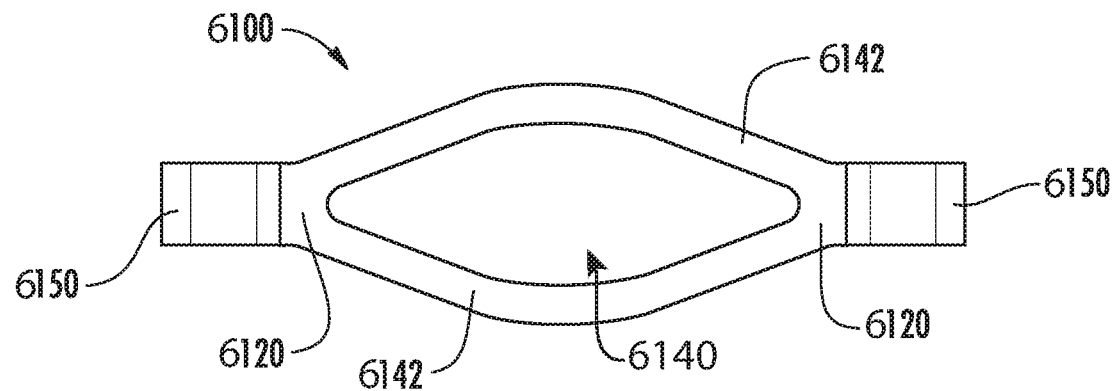
FIG. 93 is a top view of a third embodiment of the current technology depicting an implant with integral bone engaging means.
Figure 94:
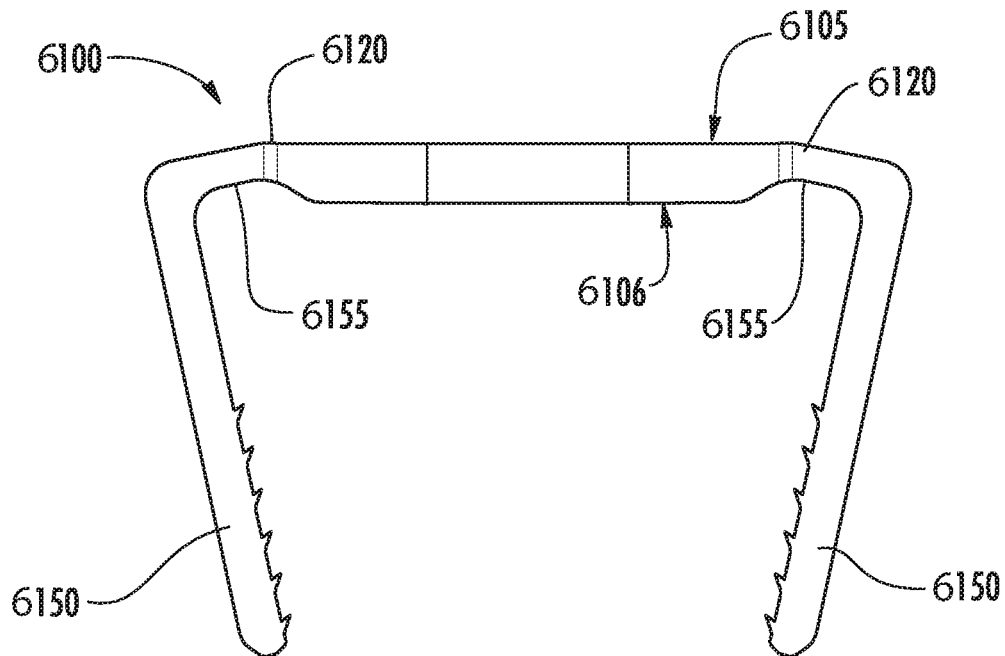
FIG. 94 is a side view of the third embodiment of FIG. 93 depicting regions and or features for controlling at least one direction of force.

FIGS. 93 and 94 show a third embodiment of the current technology, implant 6100, having a top surface 6105 and a bottom surface 6106. FIG. 94 shows implant 6100 in a closed or compressed state. Implant 6100 has a space 6140 that may be defined by bridge members 6142 and flexing regions 6120. As previously described herein, the shape of space 6140 may vary by either contracting or expanding to create a movement or force in a predetermined direction. Implant 6100 has means 6150 for engaging bone or other tissue. Means 6150 is integral with the implant 6100. The fixation means 6150 may be varying geometries. For example means 6150 may be circular, rectangular, square, or other cross-sectional geometries. Means 6150 may be uniform in shape across the entire feature or may taper or may possess grooves, ridges, teeth, etc. Implant 6100 may have one or more means 6155 for engaging a means of insertion and or for creating bending regions positioned to provide a predetermined region for predictably controlling a motion and or direction of a second action or configuration of implant 6100. In this particular embodiment, means 6155 is shown positioned between the space 6140 and bone fixation means 6150 but may be positioned at any place on the implant where it is desirable to control the direction and or motion of a first and or second configuration and or other alternate configurations. In this particular embodiment, means 6155 may perform a combination of functions which may include acting as a connection point for an inserter, holder, driver or other instrument and or acting as a predetermined region to control the direction and or motion of a first and or second implant configuration and or other alternate configurations. Implant 6100 may or may not have a means similar to the previously described means 6010 for engaging or indexing the implant with an inserter, driver or other means of insertion or holding. As previously described herein space 6140 may compress or expand thereby creating a force that will maintain means 6150 apart. This configuration may be maintained while the implant is also held in a second configuration for insertion into bone. For example, means 6150 may be held parallel relative to one another while space 6140 is compressed. Maintaining implant 6100 in these multiple configurations prior to insertion would maintain the means 6150 parallel and at a fixed separation distance. Once implanted, the space 6140 may be allowed to change or expand thereby shortening the distance between the fixation means 6150 creating a compressing force and or action. Once implanted, the engaging means 6150 may no longer be maintained parallel and may be allowed to resume a compressed or closed configuration. Bending region 6120 and 6155 may be allowed to revert to a closed and or converging state thereby creating an alternate configuration that will create compression.

Figure 95:
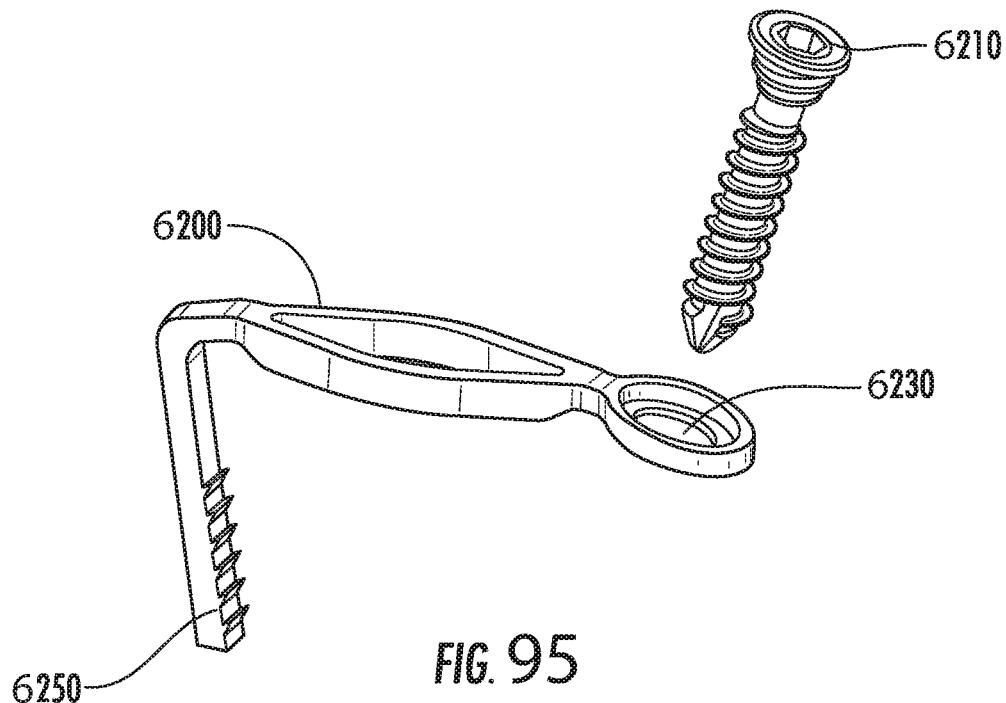
FIG. 95 is a perspective exploded view of a fourth embodiment of the current technology depicting an implant with at least one means for attaching a bone engaging means and a least one integral bone engaging means.
Figure 96:
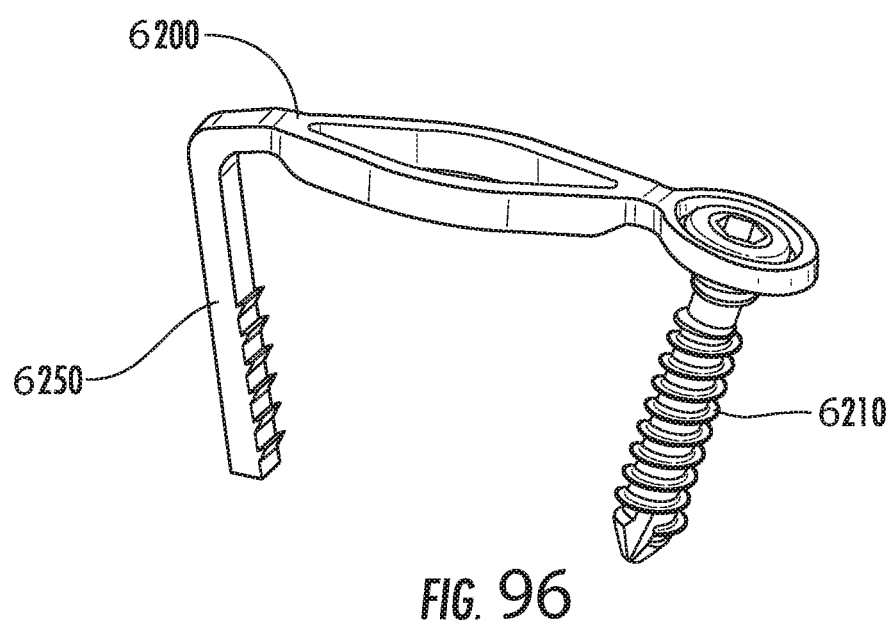
FIG. 96 is a perspective assembled view of a fourth embodiment of the current technology depicting an implant with at least one means for attaching a bone engaging means and a least one integral bone engaging means.

FIGS. 95 and 96 show a fourth embodiment of implant 6200 that combines a means 6230 for connecting to a bone engaging means 6210 and an integral bone engaging means 6250. FIG. 95 is an exploded view of the construct where bone engaging means 6210 is a typical bone screw, but may be a peg, blade, nonlocking screw, locking screw, etc. Integral bone fixation means 6250 is shown as a square cross-section similar to a typical staple leg but could be any shape or configuration as previously described herein. FIG. 96 shows the assembled construct in a closed or compressed configuration.

Figure 97:
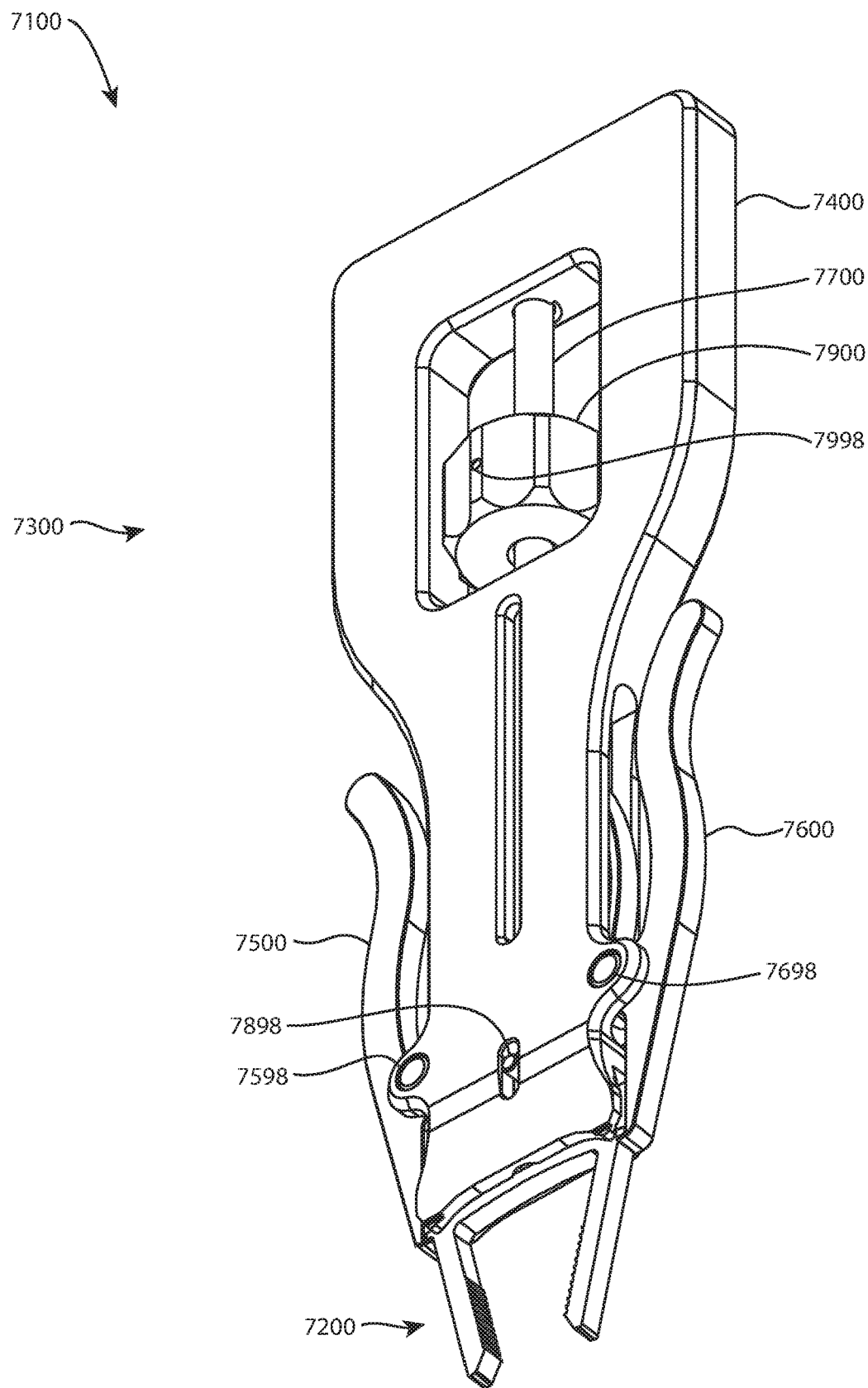
FIG. 97 is an isometric view of an implant coupled to an inserter.
Figure 98:
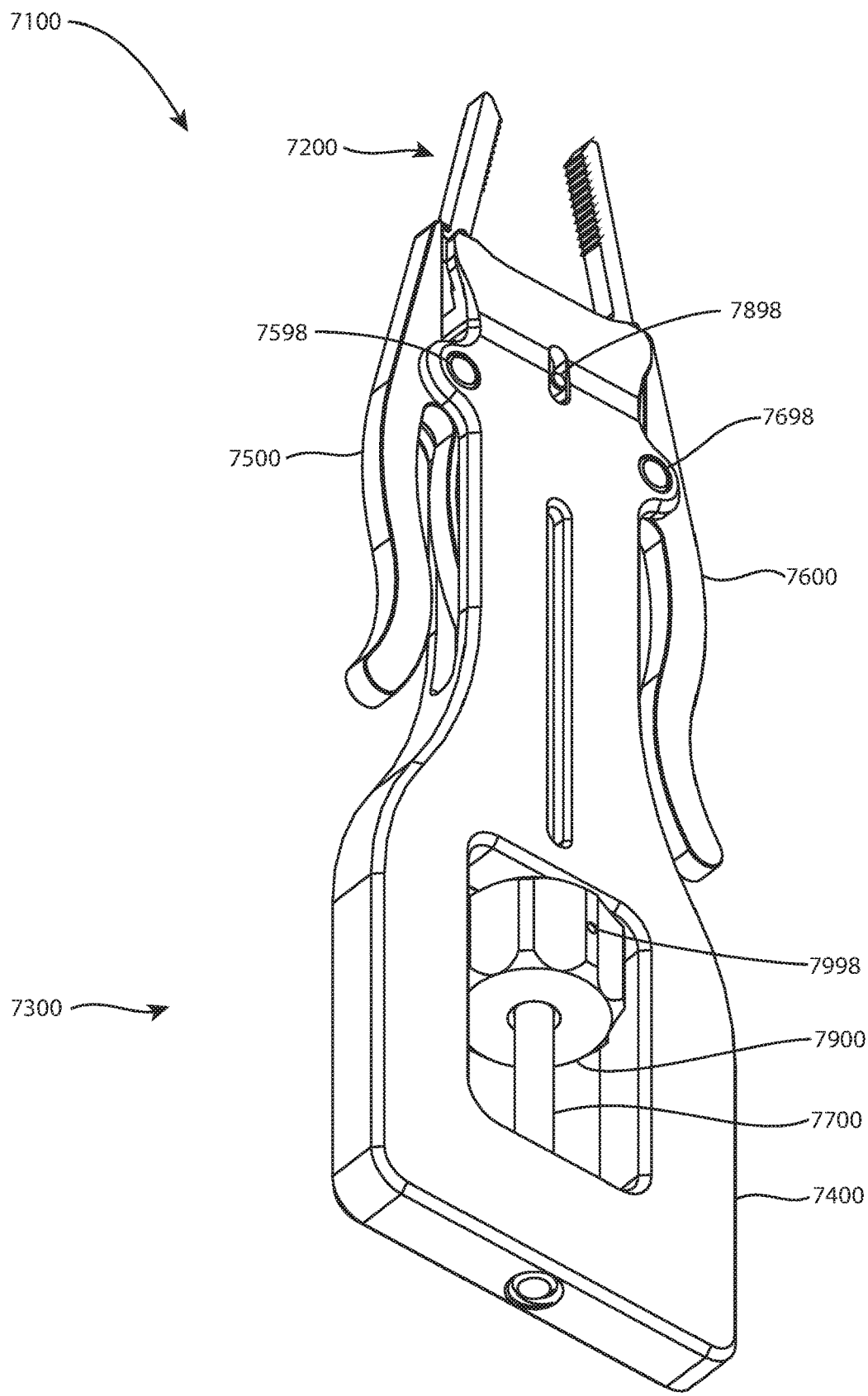
FIG. 98 is another isometric view of the implant and inserter of FIG. 97 from a different direction.

Referring to FIGS. 97 and 98, a system 7100 includes an implant 7200 and an inserter 7300. The implant 7200 is shown coupled to the inserter 7300, the implant in its free state. The illustrated implant 7200 is a compression bone staple, although the system 7100 may be adapted for implants 120, 200, 300, 600, 800, 1200, 1300, 1400, 1500, 1600, 1700, 1800, 1900, 2100, 2200, 4200, 5100, 5800, 6000, 6100, 6200.

The implant 7200 may be identical to the implant embodiment 2200 illustrated in FIGS. 78 and 79 herein, and in International Patent Application Serial No. PCT/US2015/039551.

Figures 99, 100:
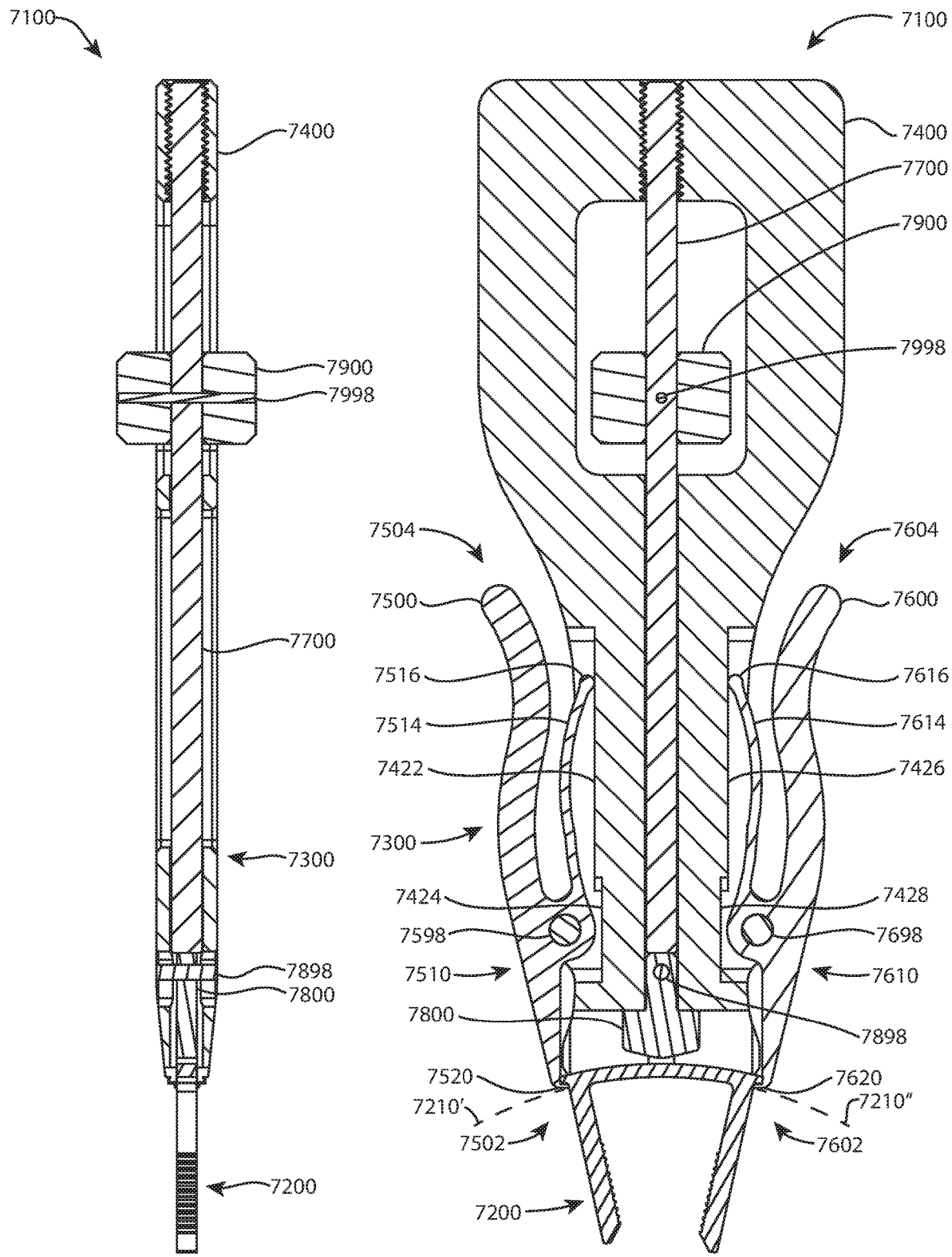
FIG. 99 is a cross sectional view of the implant and inserter of FIG. 97, taken along section line 99-99 of FIG. 112.
FIG. 100 is a cross sectional view of the implant and inserter of FIG. 97, taken along section line 100-100 of FIG. 113.
Figure 101:
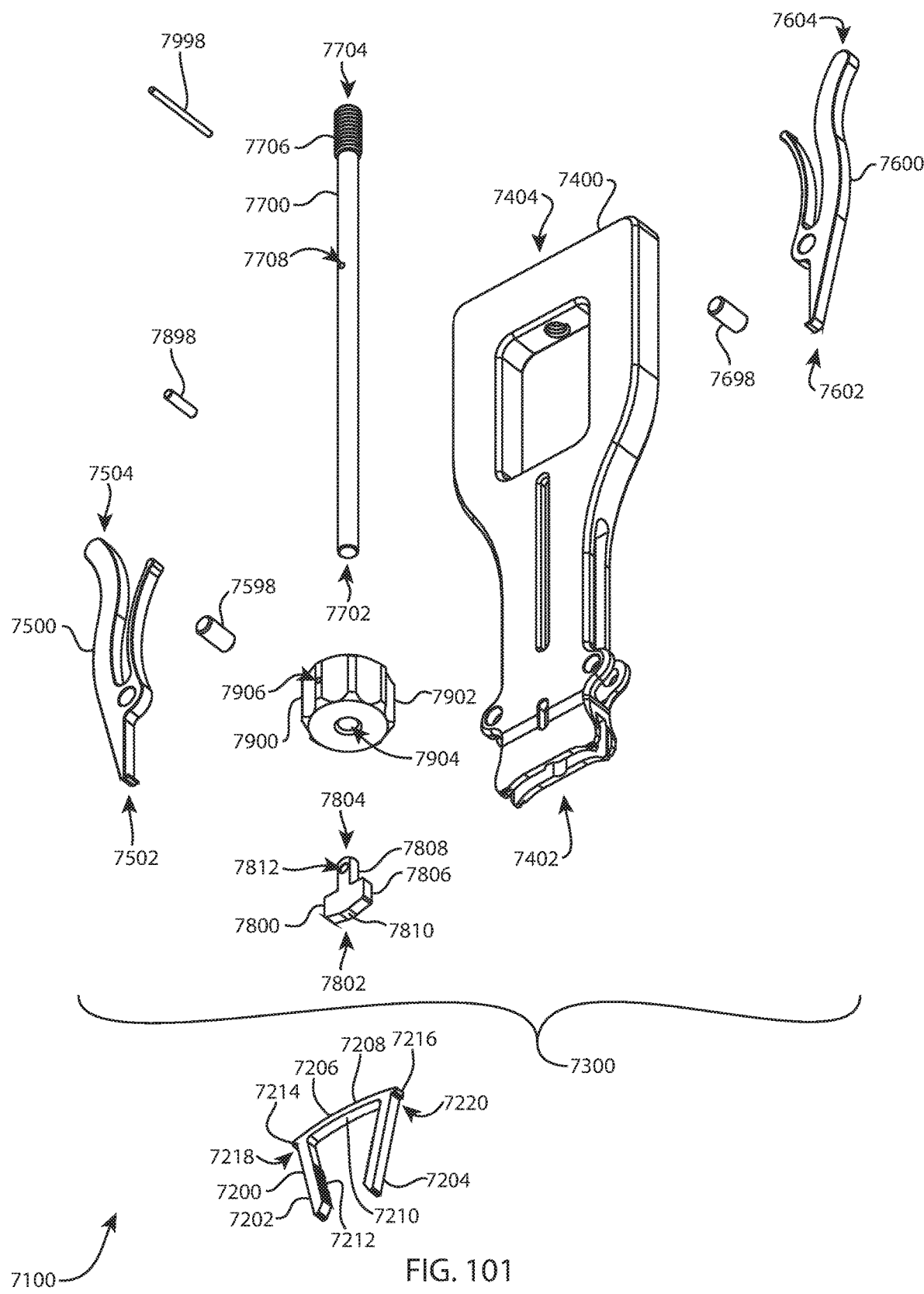
FIG. 101 is an exploded isometric view of the implant and inserter of FIG. 97.
Figure 111:
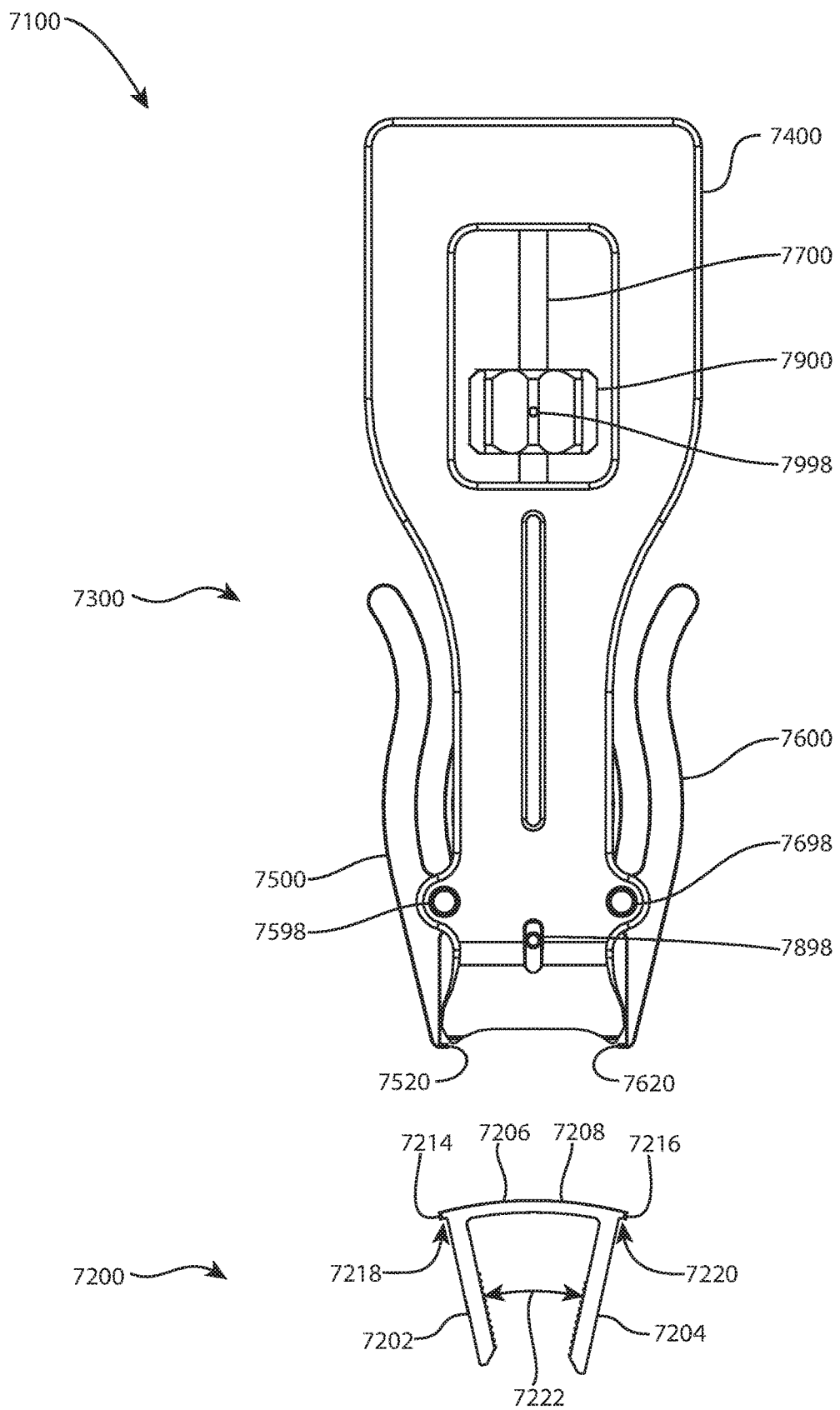
FIG. 111 is a front view of the implant and inserter of FIG. 97, the implant uncoupled from the inserter, the implant in its free state.

FIGS. 97-102 depict an implant 7200 that may have bone engaging members 7202 and 7204 integral to the implant bridge 7206. The bone engaging members 7202 and 7204 may be referred to as legs. The bone engaging member 7202 extends from a left end of the implant bridge 7206 and the bone engaging member 7204 extends from an opposite right end of the implant bridge 7206. Bone engaging member 7204 extends beside bone engaging member 7202. Implant bridge 7206 has an upper surface 7208 and a lower surface 7210. The lower surface 7210 may be referred to as a bone facing surface. The bone engaging members 7202 and 7204 may have features 7212 that may improve bone purchase or improve pull out strength of the implant 7200 from bone or soft tissue. The features 7212 may be referred to as teeth or serrations. The implant 7200 may have projections or other connecting means 7214 and 7216 for connection with a means of insertion, such as inserter 7300. The connecting means 7214 and 7216 are shown extending outwardly from the left and right ends of the bridge 7206, respectively. The connecting means 7214 and 7216 may have a lower surface 7218 and 7220 respectively that may releasably engage with a means of insertion that may allow the inserter or other means of insertion to be side loading, top loading or pivotably loaded. For example, the inserter 7300 may be described as top loading. Referring to FIGS. 100, 101, and 111, the lower surfaces 7218, 7220 are spaced apart from, or offset from, from the lower surface 7210. Referring to FIG. 100, the dashed extension lines 7210' and 7210" show the level of the lower surface 7210 versus the lower surfaces 7218, 7220. The means of insertion may maintain an implant, such as the illustrated one piece implant, in a first configuration thereby allowing a second implant configuration once the implant is disassembled from the implant. The first configuration may be an elastically deformed state, for example an insertion state. The second configuration may be a free state or an implanted state. The means of insertion may utilize features similar to connecting means 7214 and 7216 in combination with other surfaces such as top surface 7208. This combination of means of insertion may be used to maintain one or more features or arms or projections in a particular configuration. This combination of means of insertion may create a bending modality, such as a three point or four point bend, to maintain a specific implant configuration or combination of configurations. A combination of surfaces and means of insertion, such as connecting means 7214, may be used on the entire implant or portions of an implant to create or maintain a particular configuration of an implant. For example, a tab such as 7214 and top surface, such as 7208 may be used to maintain one side of an implant or one arm of an implant in a particular configuration. When disassembled, that arm may have a configuration that is different from or the same as the configuration of the rest of the implant.

Figure 102:
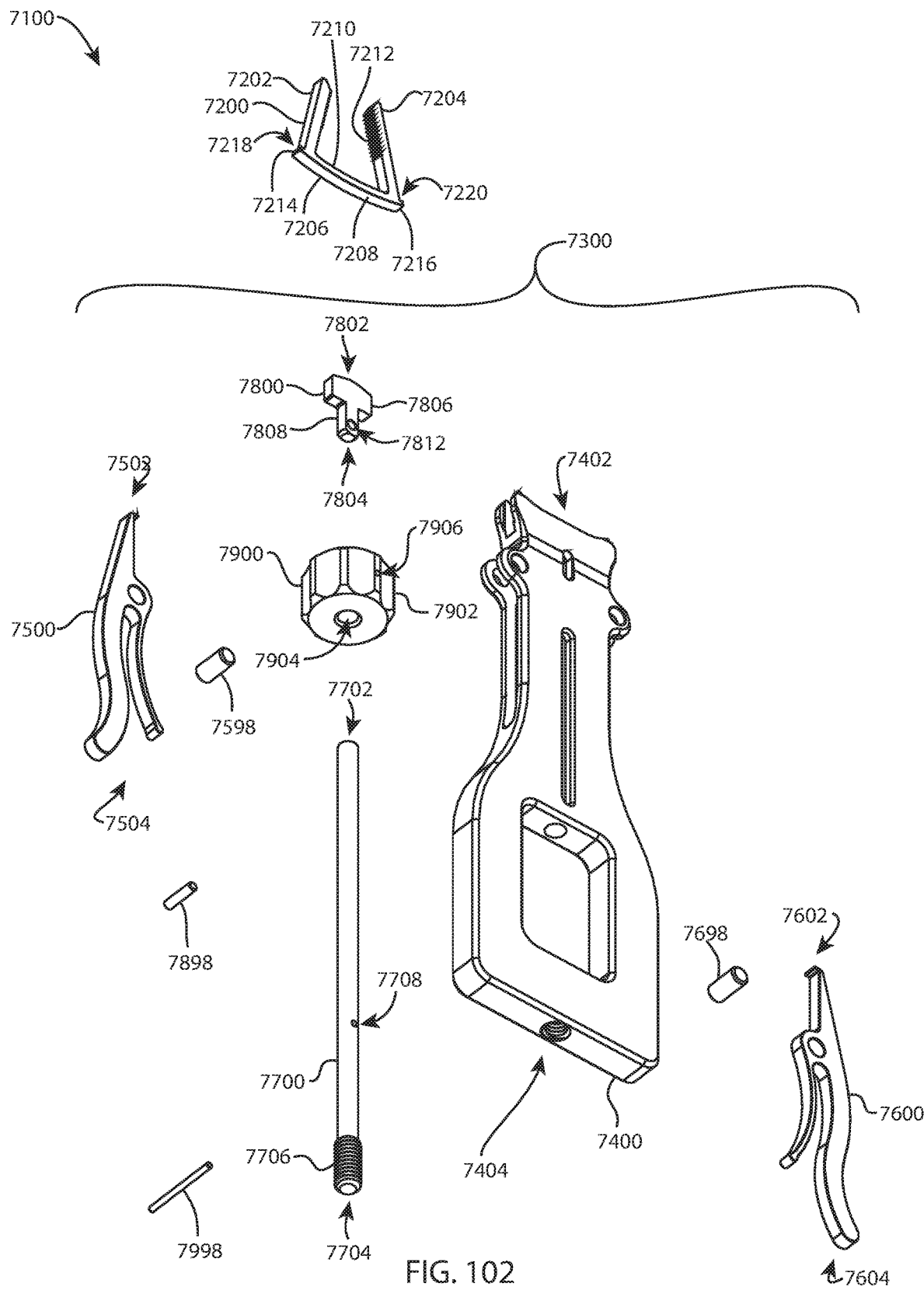
FIG. 102 is another exploded isometric view of the implant and inserter of FIG. 101 from a different direction.
Figure 103:
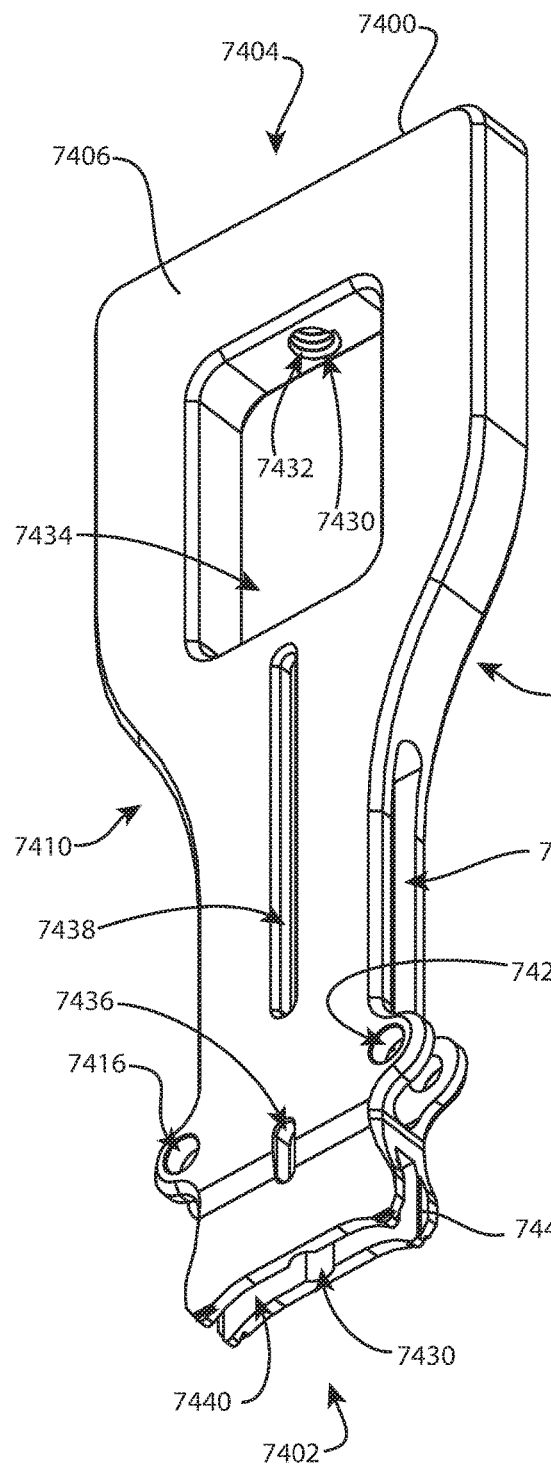
FIG. 103 is an isometric view of a body of the inserter of FIG. 97.
Figure 104:
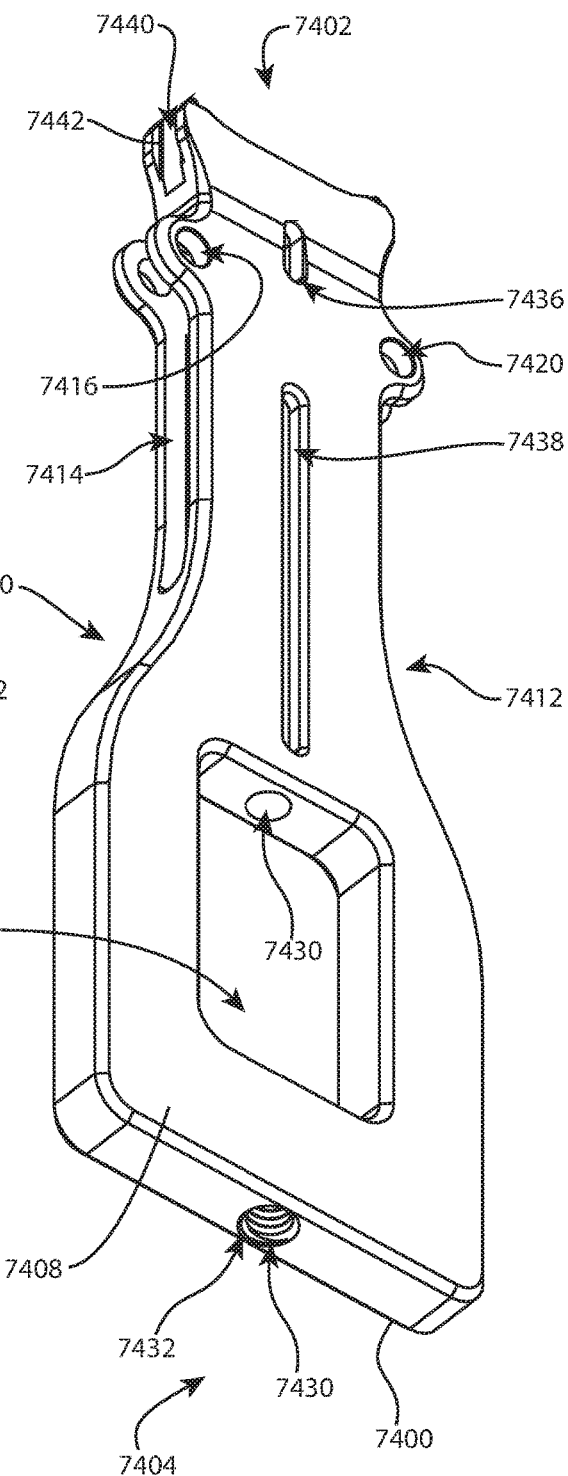
FIG. 104 is another isometric view of the body of FIG. 103 from a different direction.
Figure 107:
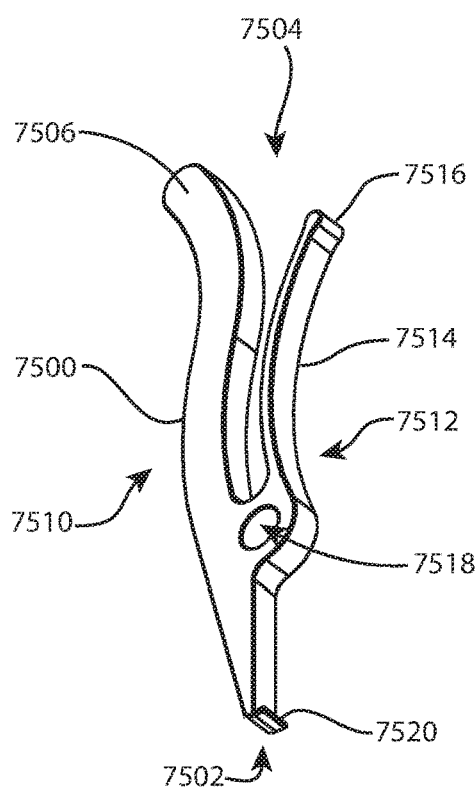
FIG. 107 is an isometric view of a first arm of the inserter of FIG. 97.
Figure 108:
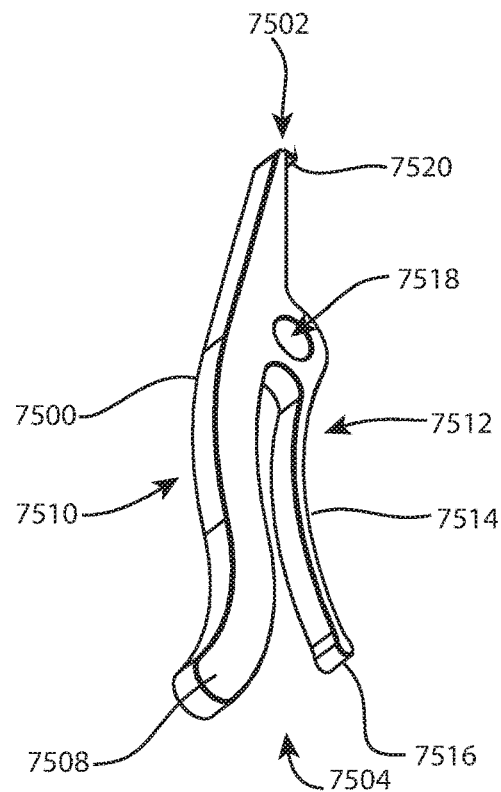
FIG. 108 is another isometric view of the first arm of FIG. 107 from a different direction.
Figure 109:
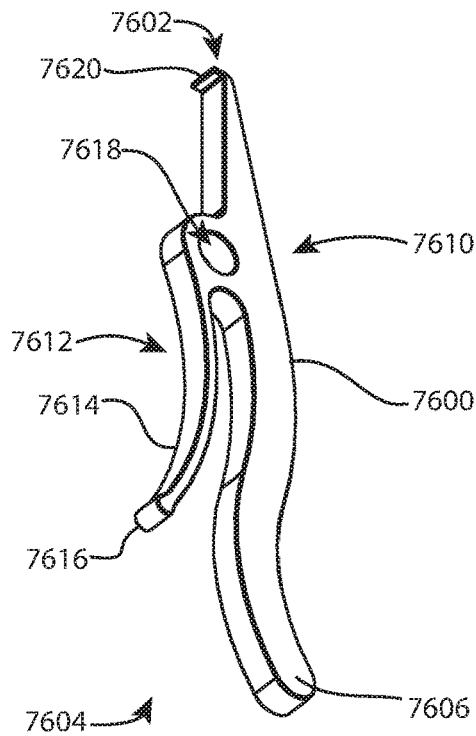
FIG. 109 is an isometric view of a second arm of the inserter of FIG. 97.
Figure 110:
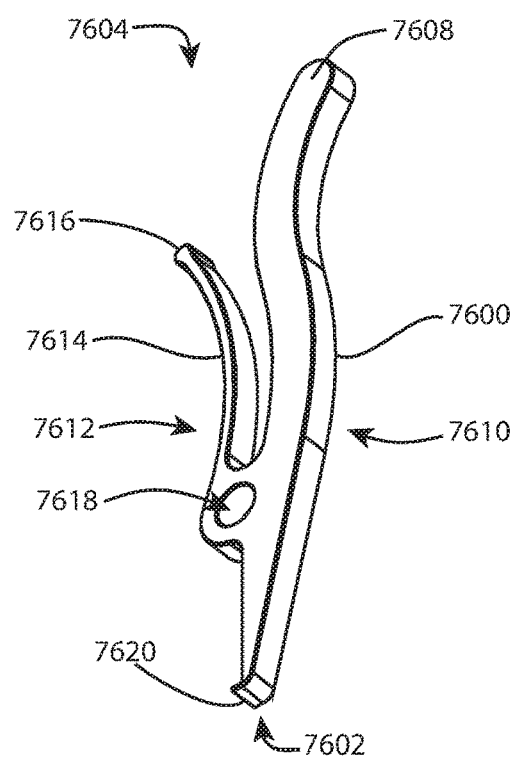
FIG. 110 is another isometric view of the second arm of FIG. 109 from a different direction.

Referring to FIGS. 101 and 102, the inserter 7300 may include a body 7400, a first arm 7500, a first arm pin 7598, a second arm 7600, a second arm pin 7698, a rod 7700, a slider 7800, a slider pin 7898, a knob 7900, and a knob pin 7998.

Figure 112:
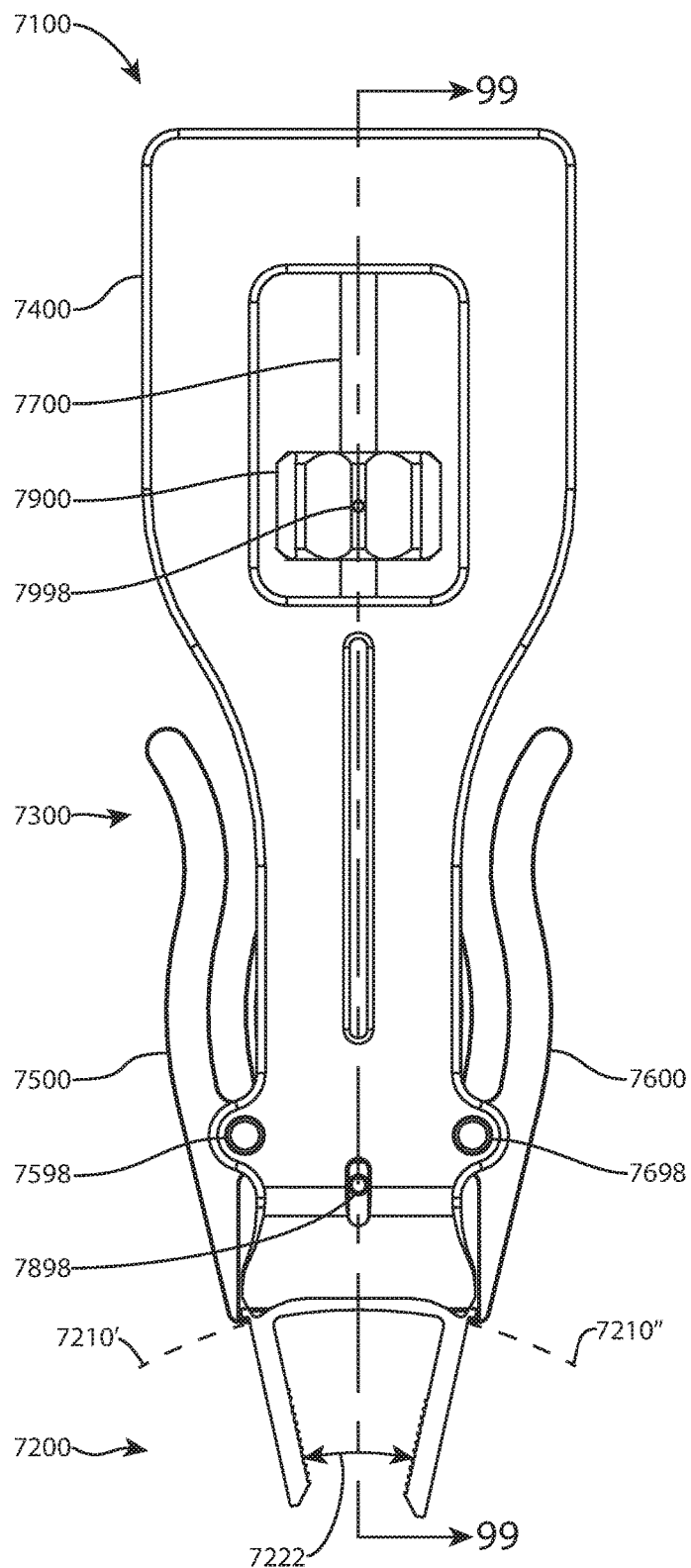
FIG. 112 is a front view of the implant and inserter of FIG. 97, the implant coupled to the inserter, the implant in its free state.
Figure 113:
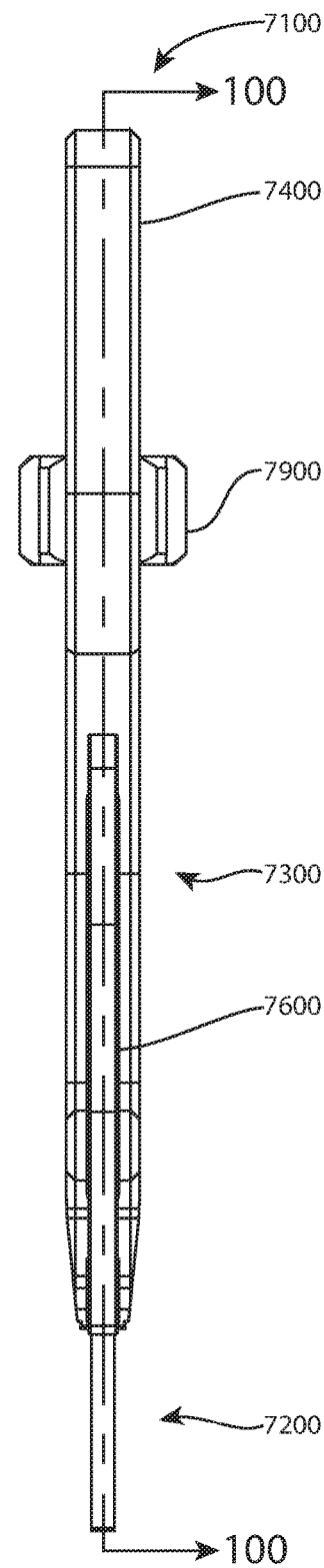
FIG. 113 is a side view of the implant and inserter of FIG. 112.

The illustrated inserter 7300 may have a first plane of symmetry along section line 99-99 of FIG. 112 and may have a second plane of symmetry along section line 100-100 of FIG. 113. The first plane of symmetry divides the inserter 7300 into substantially identical left and right halves. The second plane of symmetry divides the inserter 7300 into substantially identical front and back halves. The first and second planes of symmetry may be perpendicular to each other. The first and second planes of symmetry may also apply to the implant 7200, the body 7400, and the slider 7800.

The body 7400 is an elongated part that extends between a distal end 7402 and an opposite proximal end 7404. The distal end 7402 may be referred to as a working portion and the proximal end 7404 may be referred to as a handle. The body 7400 has a front side 7406, an opposite back side 7408, a left side 7410, and an opposite right side 7412. The body 7400 may include a left arm recess 7414, a left arm hole 7416, a right arm recess 7418, and a right arm hole 7420. The left arm recess 7414 may include a proximal portion 7422 which extends into the left side 7410 to a first depth, and a distal portion 7424 which extends into the left side 7410 to a second depth which is greater than the first depth. The right arm recess 7418 is a mirror image of the left arm recess 7414 in this example. The right arm recess 7418 may include a proximal portion 7426 which extends into the right side 7412 to a first depth, and a distal portion 7428 which extends into the right side 7412 to a second depth which is greater than the first depth. The left arm hole 7416 and the right arm hole 7420 may extend through the front side 7406 and the back side 7408. The body 7400 may include a central longitudinal passageway 7430 with an internally threaded proximal portion 7432. The central longitudinal passageway 7430 may extend through the distal end 7402 and the proximal end 7404. The body 7400 may include a proximal window 7434 and a distal window 7436, both of which may extend through the front side 7406 and the back side 7408. An optional middle window 7438 is also shown. The body 7400 may include a distal slot 7440 which extends into the distal end 7402 and may intersect the left side 7410 and the right side 7412. The distal slot 7440 may become wider where it intersects the left side 7410 and the right side 7412, thus forming ledges 7442.

The first arm 7500 is an elongated part that extends between a distal end 7502 and an opposite proximal end 7504. The distal end 7502 may be referred to as a jaw and the proximal end 7504 may be referred to as a lever. The first arm 7500 has a front side 7506, an opposite back side 7508, an outer side 7510, and an opposite inner side 7512. The first arm 7500 may include a spring element 7514, which is a cantilever beam in this example. The spring element 7514 may protrude from the inner side 7512, extend beside the proximal end 7504, and terminate in a free end 7516. The spring element 7514 may be replaced by a separate spring. The first arm 7500 may include a hole 7518 that may extend through the front side 7506 and the back side 7508. The distal end 7502 may terminate in a small hook 7520 that may protrude from the inner side 7512.

The first arm pin 7598 may extend through the left arm hole 7416 of the body 7400 and the hole 7518 of the first arm 7500 to couple the first arm to the body so that the distal end 7402 and the distal end 7502 face the same direction, the front side 7406 and the front side 7506 face the same direction, the inner side 7512 faces into the left arm recess 7414, and the free end 7516 rests against the proximal portion 7422 of the left arm recess 7414. The spring element 7514 may bias the first arm 7500 so that the distal end 7502 is close to the first plane of symmetry. In other words, the first arm 7500 may be biased so that the jaw is normally closed.

The second arm 7600 in this example is identical to the first arm 7500. However, to differentiate the two parts, the second arm is given reference number series 7600.

The second arm 7600 is an elongated part that extends between a distal end 7602 and an opposite proximal end 7604. The distal end 7602 may be referred to as a jaw and the proximal end 7604 may be referred to as a lever. The second arm 7600 has a front side 7606, an opposite back side 7608, an outer side 7610, and an opposite inner side 7612. The second arm 7600 may include a spring element 7614, which is a cantilever beam in this example. The spring element 7614 may protrude from the inner side 7612, extend beside the proximal end 7604, and terminate in a free end 7616. The spring element 7614 may be replaced by a separate spring. The second arm 7600 may include a hole 7618 that may extend through the front side 7606 and the back side 7608. The distal end 7602 may terminate in a small hook 7620 that protrudes from the inner side 7612.

The second arm pin 7698 may extend through the right arm hole 7420 of the body 7400 and the hole 7618 of the second arm 7600 to couple the second arm to the body so that the distal end 7402 and the distal end 7602 face the same direction, the front side 7406 and the back side 7608 face the same direction, the inner side 7612 faces into the right arm recess 7418, and the free end 7616 rests against the proximal portion 7426 of the right arm recess 7418. The spring element 7614 may bias the second arm 7600 so that the distal end 7602 is close to the first plane of symmetry. In other words, the second arm 7600 may be biased so that the jaw is normally closed.

The rod 7700 is an elongated shaft that extends between a distal end 7702 and an opposite proximal end 7704. The proximal end 7704 may include an externally threaded portion 7706. A hole 7708 may extend transversely through the rod 7700. The hole 7708 may be located between the externally threaded portion 7706 and the distal end 7702. The rod 7700 may fit into the passageway 7430 of the body 7400 so that the distal end 7402 and the distal end 7702 face the same direction, the externally threaded portion 7706 threads into the internally threaded proximal portion 7432, and the hole 7708 is exposed in the proximal window 7434.

The slider 7800 extends between a distal end 7802 and an opposite proximal end 7804. The slider 7800 may include a distal body 7806 and a proximal shaft 7808 that extends from the body 7806. The body 7806 may include a distal surface 7810 which is convex, although the distal surface 7810 may be flat or concave in other examples. A hole 7812 may extend transversely through the shaft. The slider may fit into the distal slot 7440 of the body 7400 so that the distal end 7402 and the distal end 7802 face the same direction, the body 7806 is in the slot 7440, the shaft 7808 extends into the passageway 7430, and the hole 7812 is exposed in the distal window 7436.

The slider pin 7898 may extend through the distal window 7436 and the hole 7812 to couple the slider 7800 to the body 7400 so that the slider is free to translate between a distal position and a proximal position. The limits of distal and proximal travel may be established by the distal-to-proximal size, or length, of the distal window 7436 and the size, or diameter, of the slider pin 7898. The slider pin 7898 may be used as an indicator of implant deformation, in which case indicia may be marked on the body 7400 in the vicinity of the distal window 7436. The indicia may be lines, tick marks, dots, icons, or the like. The indicia may correspond to the bone engaging members 7202, 7204 being convergent, parallel, and divergent. The slider pin 7898 may align with each mark in turn as the slider pin translates between the distal and proximal positions.

The knob 7900 is a cylindrical part. The knob 7900 may include an exterior grip texture 7902, which in this example is an array of longitudinal grooves or flutes. The knob may include a central longitudinal hole 7904 and a transverse hole 7906. The rod 7700 may fit into the hole 7904.

The knob pin 7998 may extend through the hole 7906 and the hole 7708 to couple the knob 7900 to the rod 7700.

The body 7400, rod 7700, and knob 7900 may be assembled by positioning the knob 7900 in the proximal window 7434; advancing the distal end 7702 of the rod sequentially into the internally threaded proximal portion 7432 of the body, the central longitudinal hole 7904, and the distal portion of the central longitudinal passageway 7430; and inserting the knob pin 7998 through the holes 7906 and 7708. When the body 7400, rod 7700, and knob 7900 are fully assembled, the rod 7700 may be moved distally and proximally within the passageway 7430 by turning the knob 7900 clockwise or counterclockwise. The limits of distal and proximal travel may be established by the distal-to-proximal size of the proximal window 7434 and the distal-to-proximal size of the knob 7900.

When the inserter 7300 is fully assembled, if the rod 7700 is moved distally, the distal end 7702 of the rod may eventually contact the proximal end 7804 of the shaft 7808 of the slider 7800. If the rod 7700 continues to move distally, it may push the slider distally until the slider pin 7898 contacts the distal side of the distal window 7436. If the rod 7700 is moved proximally, the distal end 7702 may separate from the proximal end 7804 so that there is a gap between the distal end 7702 and the proximal end 7804. The slider 7800 may then be free to slide distally and proximally between its distal and proximal positions. Advantageously, the separation of the distal end 7702 from the proximal end 7804 may make cleaning the inserter 7300 easier and more reliable.

Referring to FIG. 111, the implant 7200 is shown uncoupled from the inserter 7300. The implant 7200 is in a free state, or relaxed state, which is the shape of the implant when no external forces are acting upon the implant, other than gravity; in the free state shown, the bridge 7206 is curved so that the lower surface 7210 is concave, and the bone engaging members 7202 and 7204 converge as they extend away from the bridge 7206. An angle 7222 is formed between the bone engaging members 7202 and 7204 in the free state. The angle 7222 opens toward the bridge 7206. The angle 7222 may be referred to as a free state angle. The angle 7222 may be as large as 35 degrees. In other examples, in the free state, the bridge 7206 may be straight or curved in another orientation, for example so that the upper surface 7208, the front surface, or the back surface is concave. In other examples, in the free state, the bone engaging members 7202 and 7204 may be substantially parallel or they may diverge as they extend away from the bridge 7206.

Referring to FIG. 112, the implant 7200 is shown coupled to the inserter 7300. The implant is in the free state. In other words, the rod 7700 is not pushing the slider 7800 distally against the bridge 7206. The implant 7200 may be coupled to the inserter 7300 by inserting the bridge 7206 of the implant 7200 into the distal slot 7440 of the body 7400 and engaging the hooks 7520, 7620 of the first and second arms 7500, 7600 under the connecting means 7214, 7216 of the implant 7200. Squeezing the proximal end 7504 of the first arm 7500 and the proximal end 7604 of the second arm 7600 together, i.e., towards the first plane of symmetry, may spread apart the hooks 7520, 7620 so that the bridge 7206 can be inserted into the distal slot 7440. Since the first and second arms 7500, 7600 may be biased so that the jaws (hooks 7520, 7620) are normally closed, releasing the inward force on the proximal ends 7504, 7604 may allow the hooks to close under the connecting means 7214, 7216. The implant 7200 may be pre-loaded on the inserter 7300 in a package, such as a sterile package, with the implant in the free state.

Referring to FIGS. 100, 112, and 114-116, when the implant 7200 is coupled to the inserter 7300, the hooks 7520, 7620 preferably do not extend below, or distal to, the lower surface 7210. Preferably, the hooks 7520, 7620 may be even with, or flush with, the lower surface 7210; or spaced apart from, or offset from, the lower surface 7210. More specifically, the distal-most aspect of each hook 7520, 7620 may preferably be at the same level as, or proximal to, the lower surface 7210. This is significant because the lower surface 7210 may rest against a bone surface, or the surface of another type of tissue, when the implant 7200 is implanted. The implant 7200 may be fully seated against the tissue surface without the hooks 7520, 7620 interfering with the tissue surface. Referring to FIGS. 100, 112, and 114-116, the dashed extension lines 7210' and 7210" show the level of the lower surface 7210 when the implant 7200 is in the free state and various elastically deformed states. The distal-most aspect of the hooks 7520, 7620 are proximal to the lower surface 7210 in the illustrated example.

Figure 114:
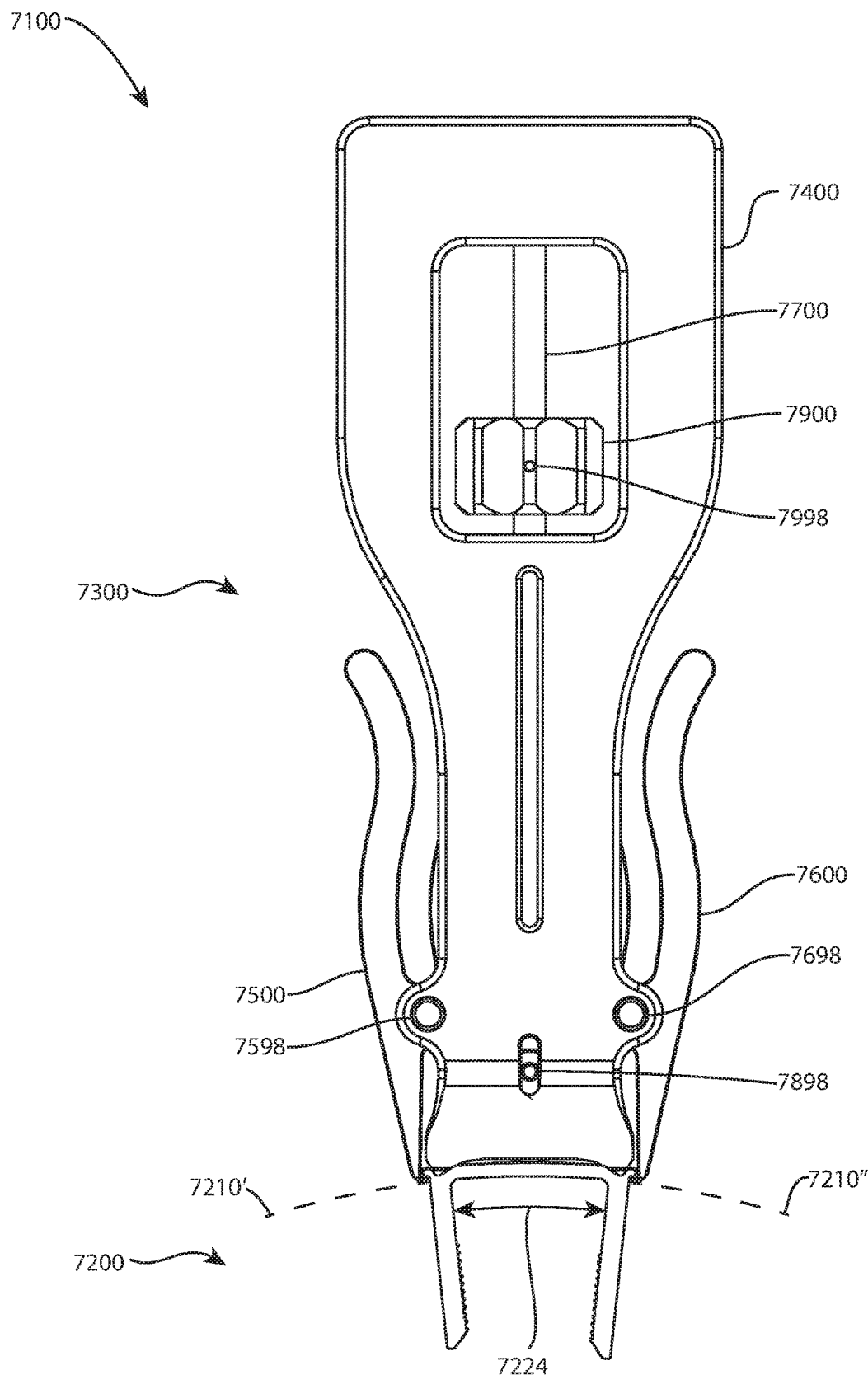
FIG. 114 is a front view of the implant and inserter of FIG. 97, the implant coupled to the inserter, the implant in an elastically deformed state in which the legs converge.
Figure 115:
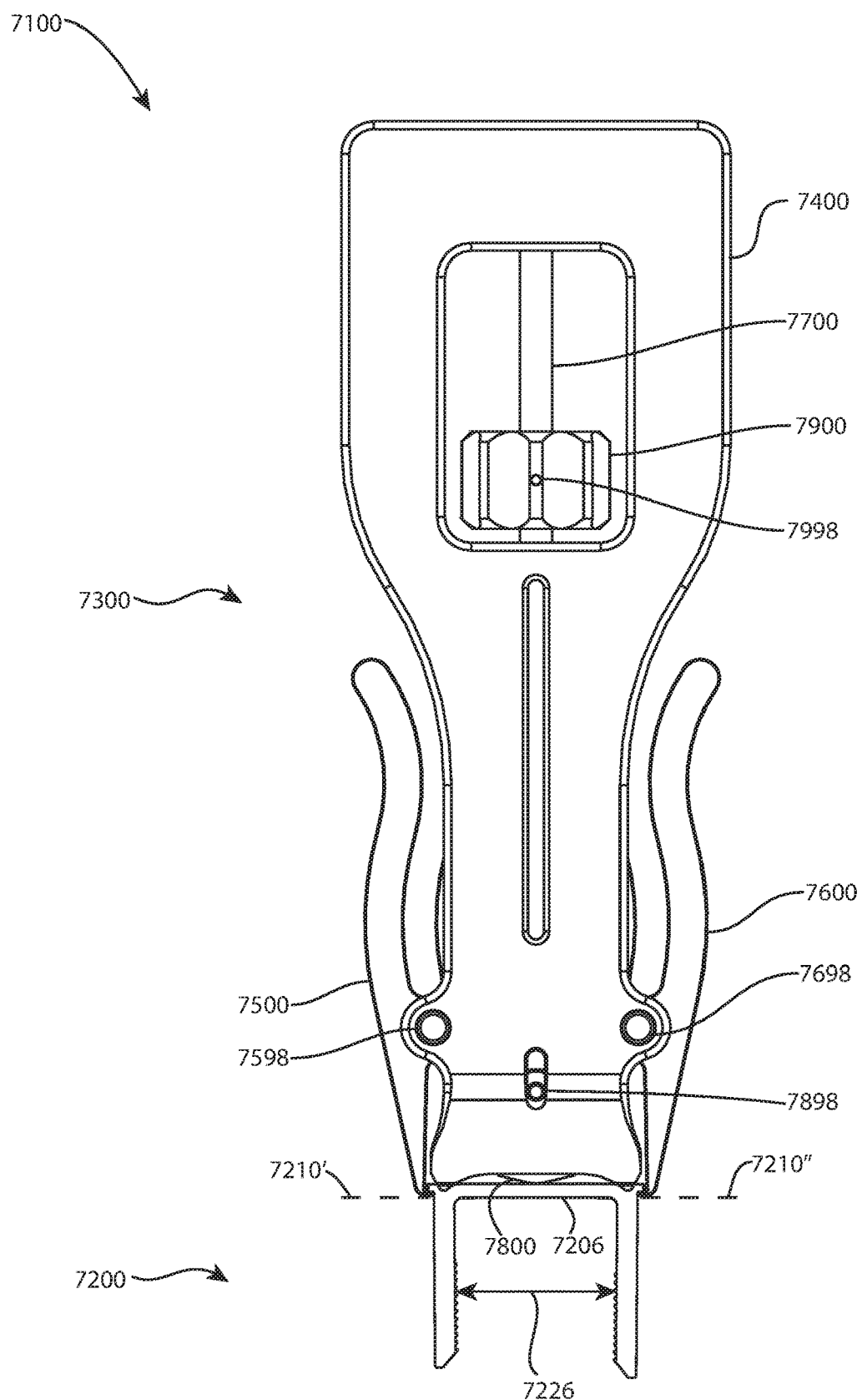
FIG. 115 is a front view of the implant and inserter of FIG. 97, the implant coupled to the inserter, the implant in an elastically deformed state in which the legs are parallel.
Figure 116:
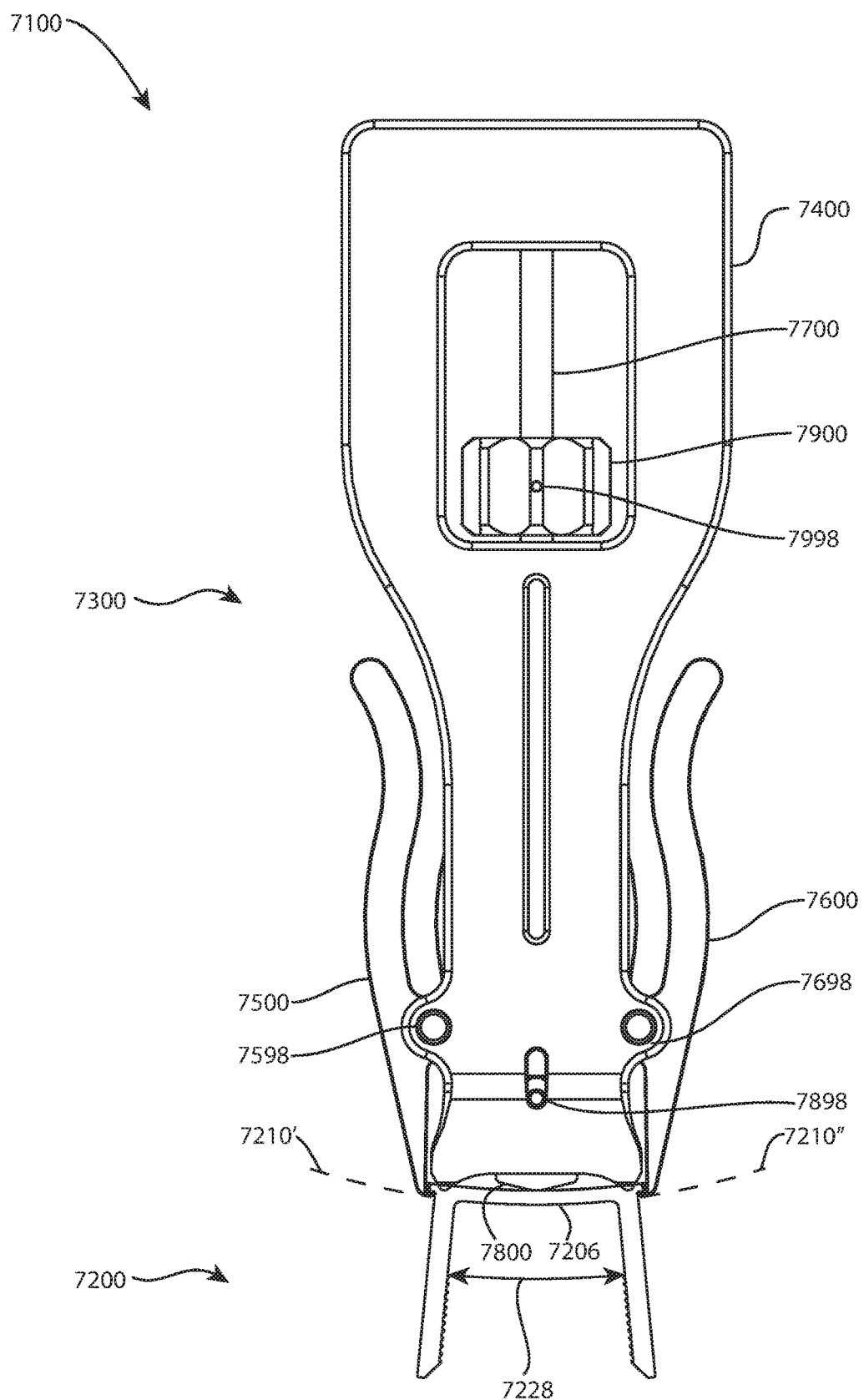
FIG. 116 is a front view of the implant and inserter of FIG. 97, the implant coupled to the inserter, the implant in an elastically deformed state in which the legs diverge.
Figure 117:
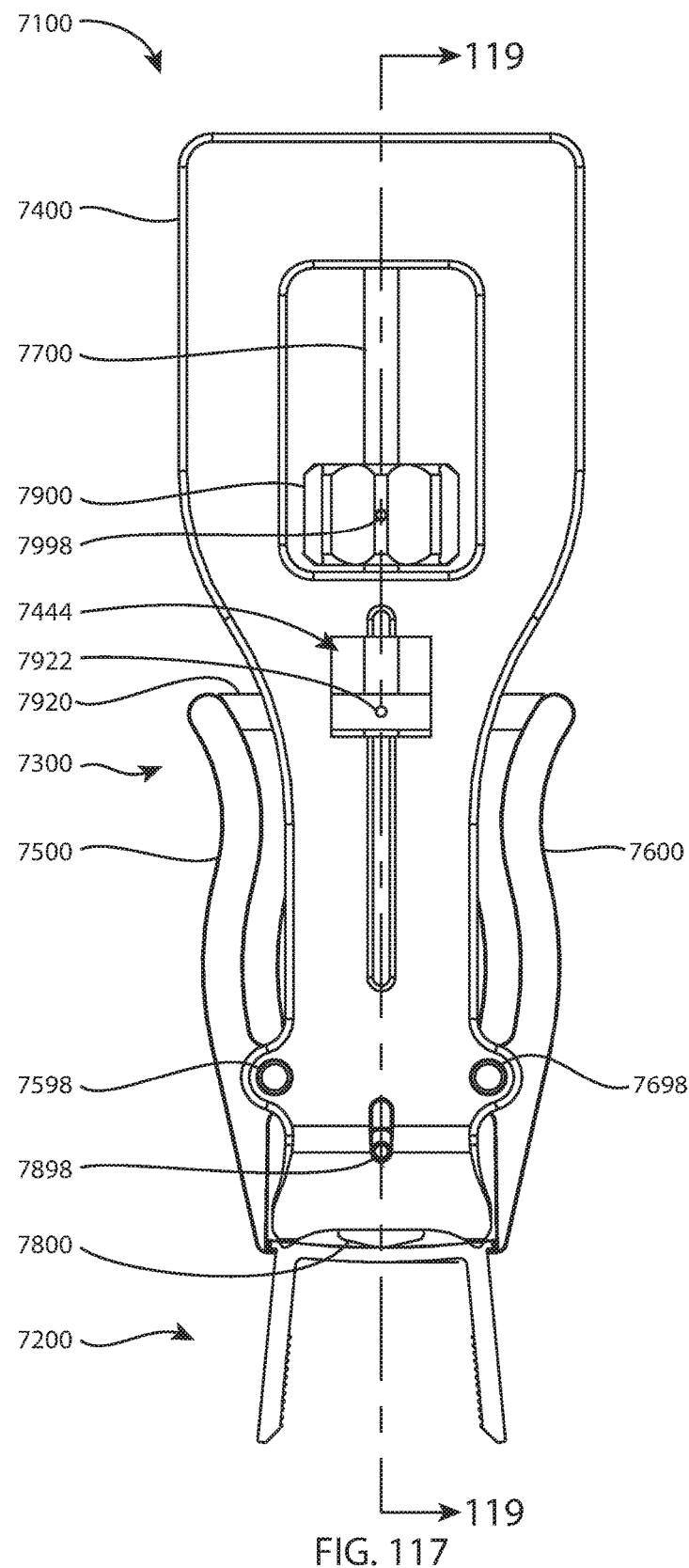
FIG. 117 is a front view of the implant and inserter of FIG. 116, the implant coupled to the inserter, the implant in the elastically deformed state in which the legs diverge, the inserter modified to include an interlock component.
Figure 118:
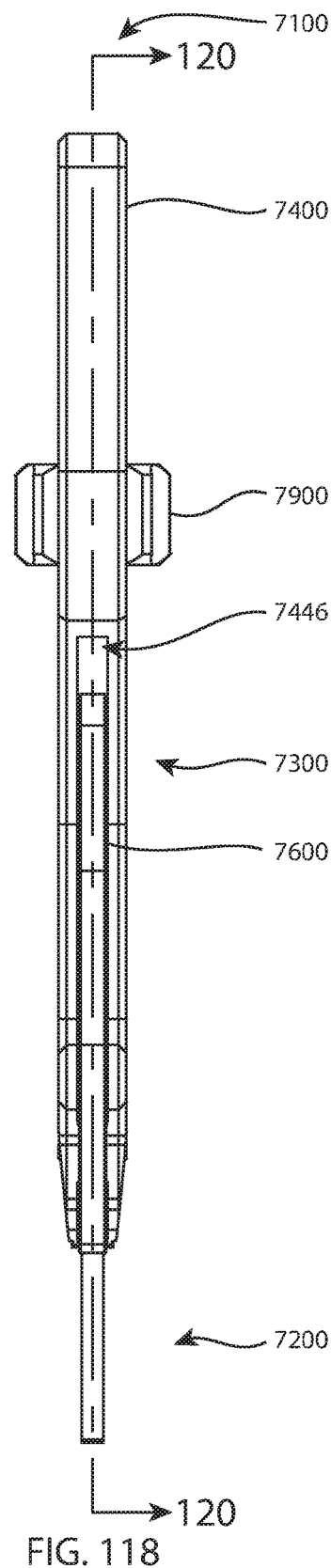
FIG. 118 is a side view of the implant and inserter of FIG. 117.
Figures 119, 120:
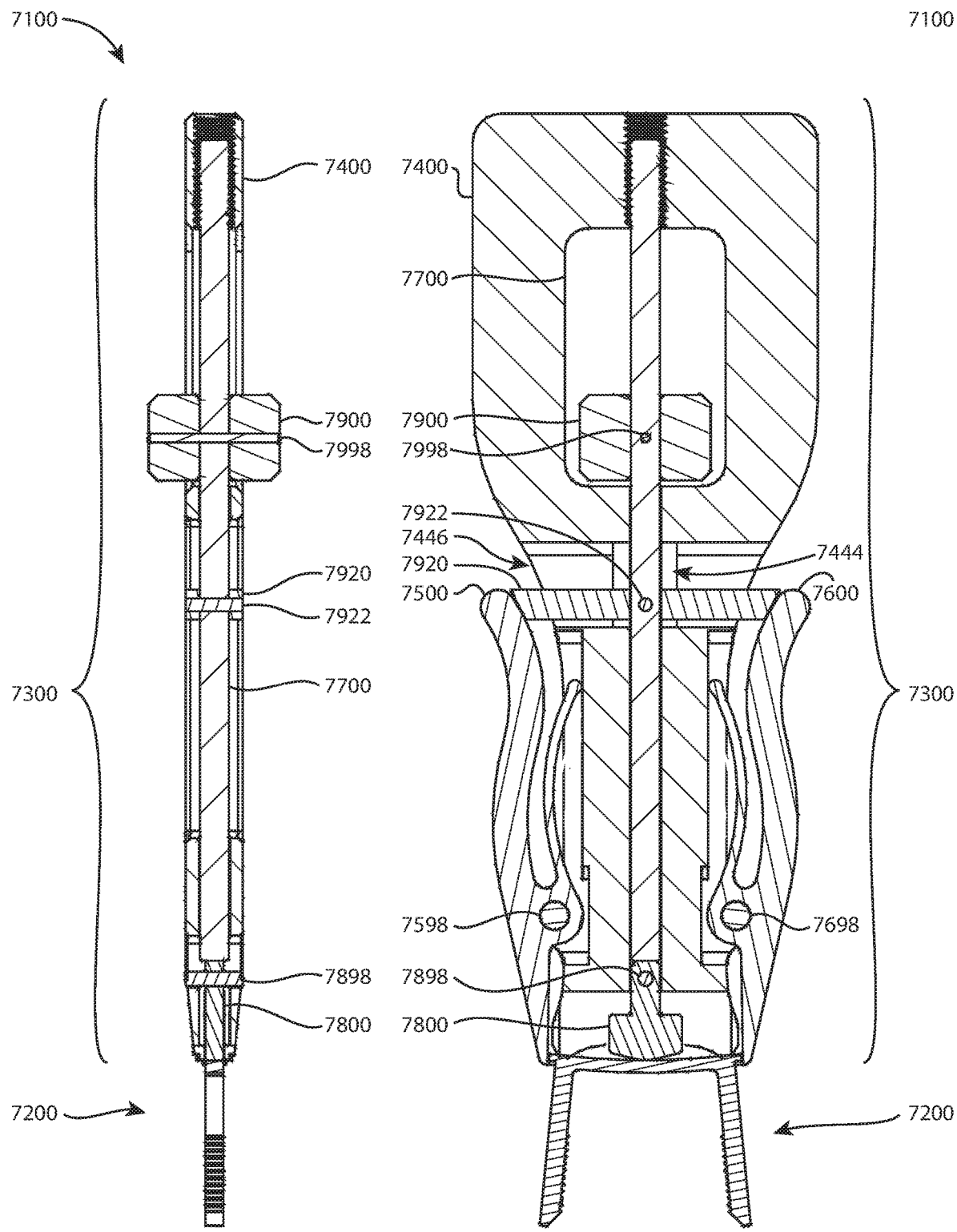

Referring to FIGS. 114-116, when the implant 7200 is coupled to the inserter 7300, the knob 7900 may be actuated to urge the implant 7200 into an elastically deformed state. This action may occur independent of coupling or decoupling the implant and the inserter. Turning the knob 7900 clockwise or counterclockwise may cause the rod 7700 to move distally or proximally, respectively, within the passageway 7430. As the rod 7700 moves distally, the distal end 7702 of the rod may contact the proximal end 7804 of the shaft 7808 of the slider 7800 and may push the slider distally. As the slider 7800 moves distally, the distal surface 7810 may contact the upper surface 7208 of the bridge 7206 and may push the bridge distally against the resistance provided by the hooks 7520, 7620 under the connecting means 7214, 7216. The example slider 7800 contacts and pushes against the center of the upper surface 7208 to put the bridge into three point bending. However, the distal end 7802 of the slider may be designed to contact and push against a different location along the upper surface 7208, or multiple locations. A two-prong slider that contacts and pushes against two separate locations along the upper surface 7208 would put the bridge into four point bending, for example. The distal and proximal travel of the slider 7800 may be limited by impingement of the slider pin 7898 against the distal and proximal sides of the distal window 7436. The distal travel limit of the slider 7800 may be selected so that the stress in the bridge 7206 remains in the elastic zone. Mechanical advantage may be achieved via the internally threaded proximal portion 7432 and the externally threaded portion 7706, an over-center cam, a scotch yoke, or other mechanism that provides mechanical advantage to push the slider 7800 or equivalent structure against the bridge 7206.

FIG. 114 illustrates one example of a first elastically deformed state in which the bone engaging members 7202 and 7204 converge as they extend away from the bridge 7206. An angle 7224 is formed between the bone engaging members 7202 and 7204 in the first elastically deformed state. The angle 7224 opens toward the bridge 7206. The angle 7224 is less than the free state angle 7222.

FIG. 115 illustrates one example of a second elastically deformed state in which the bone engaging members 7202 and 7204 are parallel, or substantially parallel. The slider 7800 is visible contacting the bridge 7206. An angle 7226 is formed between the bone engaging members 7202 and 7204 in the second elastically deformed state. When the bone engaging members 7202 and 7204 are parallel, the angle 7226 is zero. The bone engaging members 7202 and 7204 may converge slightly or diverge slightly as they extend away from the bridge 7206. Thus the magnitude of angle 7226 may be 0 degrees±10 degrees, 0 degrees±7 degrees, 0 degrees±5 degrees, 0 degrees±3 degrees, or 0 degrees±1 degrees. In this specification, "substantially parallel" refers to any of these magnitudes and tolerances. When the bone engaging members 7202 and 7204 converge, the angle 7226 opens toward the bridge 7206. When the bone engaging members 7202 and 7204 diverge, the angle 7226 opens away from the bridge 7206. The angle 7226 is less than the free state angle 7222 and the angle 7224.

FIG. 116 illustrates one example of a third elastically deformed state in which the bone engaging members 7202 and 7204 diverge as they extend away from the bridge 7206. The slider 7800 is visible contacting the bridge 7206. An angle 7228 is formed between the bone engaging members 7202 and 7204 in the third elastically deformed state. The angle 7228 opens away from the bridge 7206. The angle 7228 is greater than the angle 7226. The angle 7228 may be as large as 20 degrees. Thus, the full range of motion of the bone engaging members 7202, 7204 may go from 35 degrees convergent to 20 degrees divergent, including the zero degree parallel state.

Referring to FIGS. 117-120, the inserter 7300 may include an optional interlock component 7920 and interlock pin 7922 to prevent the implant 7200 from being decoupled from the inserter 7300 when the implant is in an elastically deformed state, particularly a state with significant potential energy. In this specification, "significant potential energy" is potential energy sufficient to cause harm or injury to a person if suddenly released as kinetic energy. The interlock component 7920 may be pinned to the rod 7700 like slider 7800 or knob 7900. The interlock component 7920 may be positioned longitudinally along the rod 7700 so that as the shaft moves distally, the interlock component engages the first and second arms 7500, 7600 to prevent the proximal ends 7504, 7604 from squeezing together and to prevent the hooks 7520, 7620 from spreading apart inadvertently. Furthermore, the interlock component 7920 may be positioned along the rod 7700 so that when the shaft is proximally positioned, the interlock component is disengaged from the first and second arms 7500, 7600 so that they are free to move. For example, referring to FIGS. 100 and 120, the interlock component 7920 may be positioned next to the proximal ends 7504, 7506 or next to the first and second arm pins 7598, 7698. When the interlock component 7920 is included, the body 7400 may include one or more additional windows 7444, 7446 to provide access for the interlock component to engage the first and second arms 7500, 7600 and the rod 7700. The body 7400 may include indicia to indicate when the interlock component 7920 is engaged (locked) and/or disengaged (unlocked). The indicia may reference the interlock component 7920 or the interlock pin 7922, for example.

A surgical method for stabilizing first and second bone fragments may include any or all of the following steps in any order: preparing a first hole in the first bone fragment; inserting a temporary fixation pin in the first hole; preparing a second hole in the second bone fragment; removing the temporary fixation pin from the first hole; determining an implant size corresponding to the first and second holes; selecting the proper size implant 7200 from a group of implants of various sizes; coupling the selected implant 7200 to the inserter 7300, the implant 7200 in the free state; urging the implant 7200 into an elastically deformed state; inserting the bone engaging member 7202 into the first hole; inserting the bone engaging member 7204 into the second hole; allowing the implant 7200 to relax toward the free state; and decoupling the inserter 7300 from the implant 7200. Coupling the implant 7200 to the inserter 7300 may comprise squeezing the proximal ends 7504, 7604 of the first and second arms 7500, 7600 together, inserting the bridge 7206 of the implant 7200 into the distal slot 7440 of the body 7400, and releasing the proximal ends 7504, 7604 to engage the hooks 7520, 7620 of the first and second arms 7500, 7600 under the connecting means 7214, 7216 of the implant 7200. Urging the implant 7200 into an elastically deformed state may comprise actuating the knob 7900 clockwise to move the rod 7700 distally to apply pressure to the slider 7800 to deflect the bridge 7206 of the implant. Urging the implant 7200 into an elastically deformed state may comprise moving the interlock component 7920 distally to engage the arms 7500, 7600 to prevent the proximal ends 7504, 7604 from inadvertently moving toward each other and/or to prevent the hooks 7520, 7620 from inadvertently spreading apart. Allowing the implant 7200 to relax toward the free state may comprise actuating the knob 7900 counterclockwise to move the rod 7700 proximally to relieve pressure against the slider 7800. Decoupling the inserter 7300 from the implant 7200 may comprise squeezing the proximal ends 7504, 7604 of the first and second arms 7500, 7600 together. Optionally, allowing the implant 7200 to relax toward the free state and decoupling the inserter 7300 from the implant 7200 may occur in a single step, and may comprise squeezing the proximal ends 7504, 7604 of the first and second arms 7500, 7600 together, particularly if the interlock component 7920 is absent or is inactive due to the implant 7200 being in an elastically deformed state with low potential energy.

Any methods disclosed herein includes one or more steps or actions for performing the described method. The method steps and/or actions may be interchanged with one another. In other words, unless a specific order of steps or actions is required for proper operation of the embodiment, the order and/or use of specific steps and/or actions may be modified.

Based on the description contained herein, it will be apparent to those skilled in the art that the current technology is not limited by the exemplary applications. The current technology may have various embodiments of varying size and various combinations, shapes and configurations are possible for varying applications. For example, an implant may have one or more integral bone engaging means in combination with one or more means for connecting to a bone engaging feature. In addition, the embodiments described herein are shown with two means for connecting to bone engaging devices but based on the description contained herein, it will be apparent to those skilled in the art that various combinations and or numbers of connection means to bone engaging features are within the scope of the current technology. Furthermore, the implant may be made of a material that may have elastic or spring properties that allow the implant to have more than one configuration. The current technology may or may not be achieved through the inherent material properties of the implant material. The implant may achieve this alternate configuration by transitioning from, for example, a first configuration to a second configuration to a third configuration. Where the first configuration may be that as attached to the inserter or delivery device and the second configuration may be a configuration that generates a first force and where the third configuration may be a configuration that generates a second force that may or may not be of the same magnitude and or direction as the first force. The embodiments described herein are not intended to be limiting. The transition from one configuration to another configuration or configurations may be one distinct transition or more than one distinct transition and there may be multiple forces of the same or different magnitudes and directions as will be apparent to those having skill in the art based on the disclosures herein. The transition may be due to the inherent material properties or achieved by a manipulation of the material or a combination thereof.

The embodiments described herein can be manufactured from a number of different materials or combinations of materials. Nitinol, for example, possesses material properties, such as shape memory and or super elasticity that may provide the inherent properties to allow an embodiment to have multiple configurations with or without an external mechanical manipulation. Still other materials such as PEEK or other polymers may also possess material properties beneficial for the embodiment described herein. A combination of materials may also be preferred. For example, a nitinol plate with titanium or PEEK screws may be the materials of choice for some embodiments. Based on the description of the technology herein, those skilled in the art will be aware of the typical materials and combinations of materials applicable to the current technology as well as the mechanism of action of the current technology as it may related to superelastic nitinol, shape memory nitinol, or the like.

The exemplary embodiments described herein are not intended to be limiting. To those skilled in the art the benefits of the technology are apparent. Furthermore those skilled in the art will appreciate that the intent of this technology may be realized in other embodiments not necessarily described herein. Any methods disclosed herein includes one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the technology.

While specific embodiments and applications of the present technology have been illustrated and described, it is to be understood that the technology is not limited to the precise configuration and components disclosed herein. Various modifications, changes, and variations which will be apparent to those skilled in the art may be made in the arrangement, operation, and details of the methods and systems of the present technology disclosed herein without departing from the spirit and scope of the technology.

The invention claimed is:

1. A fixation system for applying a force across first and second tissue segments, wherein the first tissue segment is a first bone segment or a first soft tissue segment, wherein the second tissue segment is a second bone segment or a second soft tissue segment, the tissue fixation system comprising:
   an implant comprising a bridge member, a first tissue-engaging member, and a second tissue-engaging member, wherein the first tissue-engaging member extends from a first end of the bridge member, wherein the second tissue-engaging member extends from a second end of the bridge member opposite the first end of the bridge member, wherein the first tissue-engaging member comprises a first inserter-engaging feature lateral to the first end of the bridge member, wherein the second tissue-engaging member comprises a second inserter-engaging feature lateral to the second end of the bridge member, wherein the implant is transformable between a free-state configuration and an insertion configuration, wherein transforming the implant between the free-state configuration and the insertion configuration causes a change in a relative position of the first tissue-engaging member to the bridge member; and
   an inserter connectable to the implant, comprising a first implant-engaging feature oriented to connect to the implant by engaging the first inserter-engaging feature lateral to the first end of the bridge member, a second implant-engaging feature spaced and oriented relative to the first implant-engaging feature to connect to the implant by engaging the second inserter-engaging feature lateral to the second end of the bridge member such that the bridge member extends between the first implant-engaging feature and the second implant-engaging feature when the implant is connected to the inserter, and a third implant-engaging feature spaced and oriented relative to the first implant-engaging feature and the second implant-engaging feature to engage the implant by contacting the bridge member, wherein the first implant-engaging feature and the second implant-engaging feature are configured to aid in transformation of the implant between the free-state configuration and the insertion configuration, wherein the inserter is configured to maintain the implant in the insertion configuration after transformation between the free-state configuration and the insertion configuration, such that a user is not required to exert a force on the first and second implant-engaging features to maintain the implant in the insertion configuration, wherein the first and second implant-engaging features are configured to not contact an exterior surface of the bone below a bottom surface of the bridge member so as to not interfere with final seating of the implant in its final implanted position, and wherein the first implant-engaging feature and the second implant-engaging feature are configured to disengage from the first inserter-engaging feature and the second inserter-engaging feature while the first tissue-engaging member is positioned within the first tissue segment and the second tissue-engaging member is positioned within the second tissue segment so that the first tissue-engaging member and the second tissue-engaging member apply a converging force across the first and second tissue segments.

2. The fixation system of claim 1, wherein the first inserter-engaging feature is an internal feature of the first tissue-engaging member.

3. The fixation system of claim 2, wherein the first inserter-engaging feature is positioned on the exterior of the first tissue-engaging member.

4. The fixation system of claim 1, wherein the first inserter-engaging feature is an external feature of the first tissue-engaging member.

5. The fixation system of claim 4, wherein the first inserter-engaging feature is positioned on the exterior of the first tissue-engaging member.

6. The fixation system of claim 1, wherein the first tissue-engaging member comprises a first plurality of teeth extending along an exterior surface of the first tissue-engagement member and the second tissue-engaging member comprises a second plurality of teeth extending along an exterior surface of the second tissue-engaging member.

7. A fixation system for applying a force across first and second bone segments, the bone fixation system comprising:
a staple comprising a bridge, a first leg, and a second leg, wherein the first leg extends from a first end of the bridge, wherein the second leg extends from a second end of the bridge opposite the first end of the bridge, wherein the first leg comprises a first inserter-engaging feature lateral to the first end of the bridge, wherein the second leg comprises a second inserter-engaging feature lateral to the second end of the bridge, wherein the staple is transformable between a free-state configuration and an insertion configuration, wherein transforming the staple between the free-state configuration and the insertion configuration causes a change in a relative position of the first leg to the bridge; and
an inserter connectable to the staple, comprising a first staple-engaging feature oriented to connect to the staple by engaging the first inserter-engaging feature lateral to the first end of the bridge, a second staple-engaging feature spaced and oriented relative to the first staple-engaging feature to connect to the staple by engaging the second inserter-engaging feature lateral to the second end of the bridge such that the bridge extends between the first staple-engaging feature and the second staple-engaging feature when the staple is connected to the inserter, and a third staple-engaging feature spaced and oriented relative to the first staple-engaging feature and the second staple-engaging feature to engage the staple by contacting the bridge member, wherein the first staple-engaging feature and the second staple-engaging feature are configured to aid in transformation of the staple between the free-state configuration and the insertion configuration, wherein the inserter is configured to maintain the staple in the insertion configuration after transformation between the free-state configuration and the insertion configuration, such that a user is not required to exert a force on the first and second staple-engaging features to maintain the staple in the insertion configuration, wherein the first and second staple-engaging features are configured to not contact an exterior surface of the bone below a bottom surface of the bridge so as to not interfere with final seating of the staple in its final implanted position, and wherein the first staple-engaging feature and the second staple-engaging feature are configured to disengage from the first inserter-engaging feature and the second inserter-engaging feature while the first leg is positioned within the first bone segment and the second leg is positioned within the second bone segment so that the first leg and the second leg apply a converging force across the first and second bone segments.

8. The fixation system of claim 7, wherein the first inserter-engaging feature is an internal feature of the first leg.

9. The fixation system of claim 8, wherein the first inserter-engaging feature is positioned on the exterior of the first leg.

10. The fixation system of claim 7, wherein the first inserter-engaging feature is an external feature of the first leg.

11. The fixation system of claim 10, wherein the first inserter-engaging feature is positioned on the exterior of the first leg.

12. The fixation system of claim 7, wherein the first leg comprises a first plurality of teeth extending along an exterior surface of the first leg and the second leg comprises a second plurality of teeth extending along an exterior surface of the second leg.

\* \* \* \* \*